(12) United States Patent
Mao et al.

(10) Patent No.: US 8,436,170 B2
(45) Date of Patent: May 7, 2013

(54) XANTHENE DYES COMPRISING A SULFONAMIDE GROUP

(75) Inventors: Fei Mao, Fremont, CA (US); Wai-Yee Leung, San Ramon, CA (US); Ching-Ying Cheung, San Ramon, CA (US)

(73) Assignee: Biotium, Inc., Hayward, CA (US)

( * ) Notice: Subject to any disclaimer, the term of this patent is extended or adjusted under 35 U.S.C. 154(b) by 218 days.

(21) Appl. No.: 12/699,778

(22) Filed: Feb. 3, 2010

(65) Prior Publication Data

US 2010/0197030 A1  Aug. 5, 2010

Related U.S. Application Data

(60) Provisional application No. 61/149,603, filed on Feb. 3, 2009.

(51) Int. Cl.
| C07D 405/14 | (2006.01) |
| C07D 405/12 | (2006.01) |
| C07D 491/22 | (2006.01) |
| C07D 491/147 | (2006.01) |
| C07D 311/88 | (2006.01) |

(52) U.S. Cl.
USPC ............... 544/405; 546/37; 546/48; 546/256; 548/418; 548/525; 549/227

(58) Field of Classification Search ............ 436/73; 549/227; 548/525, 418; 546/48, 256, 37; 544/405; 536/23.1, 54; 530/408, 350, 391.3
See application file for complete search history.

(56) References Cited

U.S. PATENT DOCUMENTS

| 4,731,433 | A | 3/1988 | Yatsu et al. |
| 5,623,080 | A | 4/1997 | Neckers et al. |
| 6,008,379 | A | 12/1999 | Benson et al. |
| 6,130,101 | A | 10/2000 | Mao et al. |
| 6,162,931 | A | 12/2000 | Gee et al. |
| 7,367,994 | B2 | 5/2008 | Lagrange |
| 2004/0242902 | A1 | 12/2004 | Lam et al. |
| 2006/0179585 | A1 | 8/2006 | Zilles et al. |
| 2008/0177086 | A1 | 7/2008 | Frank et al. |
| 2009/0305410 | A1* | 12/2009 | Mao et al. ........... 435/375 |

FOREIGN PATENT DOCUMENTS

| WO | WO 2004/065548 A2 | 8/2004 |
| WO | WO 2005/003086 A2 | 1/2005 |
| WO | WO 2004/065548 A3 | 4/2005 |
| WO | WO 2005/003086 A3 | 2/2006 |

OTHER PUBLICATIONS

International search report dated Mar. 29, 2010 for PCT Application No. US2010/23111.
Matscheke, et al. 4H-Imidazoles as functional dyes: synthesis of bichromophores and extension of the merocyanine system. Tetrahedron. 2008;64:7815-7821.
Shandura, et al. New heterocyclic analogues of rhodamines. Dyes and Pigments. 2007;73:25-30.
Boyarski, et al. Photostable, amino reactive and water-soluble fluorescent labels based on sulfonated rhodamine with a rigidized xanthene fragment. Chemistry. 2008;14(6):1784-92.
Cha, et al. Rhodamine-labeled 2beta-carbomethoxy-3beta-(3,4-dichlorophenyl)tropane analogues as high-affinity fluorescent probes for the dopamine transporter. J Med Chem. Dec. 1, 2005;48(24):7513-6.
Gunzenhauser, et al. Halochromic molecules. Synthesis and acidobasic behavior of substituted 3', 6'-bis(dimethylamino)-spiro[5H-imidazo[2,1-a]isoindolin-5,9'-xanthenes]. Helvetica Chimica Acta. 1979; 62(1):171-84. English abstract only.
Lefevre, et al. Texas Res-X and rhodamine Red-X, new derivatives of sulforhodamine 101 and lissamine rhodamine B with improved labeling and fluorescence properties. Bioconjug Chem. Jul.-Aug. 1996;7(4):482-9.
Yang, et al. Scalable synthesis of lissamine rhoadmine B sulfonyl chloride and incorporation of xanthene derivatives onto polymer supports. Synthesis. 2008; 6:957-961.

* cited by examiner

Primary Examiner — Kristin Bianchi
(74) Attorney, Agent, or Firm — Wilson Sonsini Goodrich & Rosati

(57) ABSTRACT

The present invention relates to fluorescent dyes in general. The present invention provides a wide range of fluorescent dyes and kits containing the same, which are applicable for labeling a variety of biomolecules, cells and microorganisms. The present invention also provides various methods of using the fluorescent dyes for research and development, forensic identification, environmental studies, diagnosis, prognosis, and/or treatment of disease conditions.

12 Claims, 6 Drawing Sheets

Cell Staining with Antibody Labeled with compound No. 4c

XANTHENE DYES COMPRISING A SULFONAMIDE GROUP

CROSS REFERENCE

This application claims the benefit of U.S. Provisional Application No. 61/149,603, filed Feb. 3, 2009, which is incorporated herein in its entirety by reference.

BACKGROUND OF THE INVENTION

Fluorescent dyes are widely used in biological research and medical diagnostics. Fluorescent dyes are superior to conventional radioactive materials because fluorescent dyes are typically sufficiently sensitive to be detected, less expensive and less toxic. In particular, a diversity of fluorophores with a distinguishable color range has made it more practical to perform multiplexed assays capable of detecting multiple biological targets in parallel. The ability to visualize multiple targets in parallel is often required for delineating the spatial and temporal relationships amongst different biological targets in vitro and in vivo. In addition, the generation of a wide range of fluorescent dyes has opened a new avenue for conducting high-throughput and automated assays, thus dramatically reducing the unit cost per assay. Moreover, the low toxicity of fluorescent dyes provides ease of handling in vitro, and also renders it safer for imaging biological activities in vivo.

Despite the various advantages of fluorescent dyes, conventional dyes have a number of profound limitations. For example, conventional fluorescent dyes are typically prone to inter-dye quenching, a phenomenon known to diminish the effective brightness of the dyes. It is a common practice to conjugate a given target with multiple dye molecules in order to maximize the brightness of the labeled target, e.g., a biomolecule such as protein or DNA. For many conventional fluorescent dyes, the fluorescence intensity of the labeled target is often not directly proportional to the number of attached dye molecules, but rather less than the predicted intensity due to, e.g., quenching amongst the multiple dyes attached to the target. Such quenching effect can be attributed to, in part, the physical interaction amongst the attached dye molecules, which may lead to formation of nonfluorescent dye dimers. Dimer formation may be driven by hydrophobic interaction. Because many traditional fluorescent dyes, such as various rhodamine dyes and cyanine dyes, are highly hydrophobic aromatic compounds, these commonly used dyes are particularly prone to forming dimers on labeled biomolecules. Adding sulfonate groups to a dye has been shown to reduce dimer formation. See, e.g., U.S. Pat. Nos. 5,268,486 and 6,977,305, 6,130,101 and Panchuk-Voloshina, et al. J. Histochem. Cytochem. 47(9), 1179 (1999). However, while sulfonation may reduce dimer formation, it also introduces negative charges into a biomolecule, and thus may increase the risk of disrupting the biological activity of the labeled biomolecule.

Sulfonated dyes (e.g., AF488, Alexa Fluor 532, Alexa Fluor 546 and Alexa Fluor 568) are useful for antibody labeling or labeling of other macromolecules where multiple dye molecules are typically in close proximity. In some instances, where reduction of background fluorescence signal relies on dye to dye interaction, the activity of the labeled biomolecule may be affected by the charge of the dye. In some instances, labeled antibodies may produce high background in certain cellular staining. To lower the background, it may be necessary to use a negatively charged polymer to act as a blocking agent (US patent application 2008/0038772).

In order to maximize fluorescence signals, fluorescent dyes need to be excited at or near their absorption maxima. The wavelengths of the existing excitation light sources are limited. For example, a 488 nm argon laser is commonly used in fluorescence microscopy, flow cytometry, PCR instruments, DNA sequencing instruments and other fluorescence-based biomedical instruments. Many conventional dyes are prone to poor photostability and undergo rapid photobleaching under intense laser light, a phenomenon known to diminish the effective brightness of dyes when a fluorescence signal is to be followed over time. For many conventional dyes, the fluorescence is also sensitive to pH changes.

In some instances, sulfonation of dyes overcomes the drawbacks of low photostability and pH sensitivity. Sulfonation also increases the water solubility and blue-shifts the absorption wavelength of a dye to a wavelength close to the 488 nm argon laser line. However, the multiple sulfonate groups make a dye relatively insoluble in nonpolar organic solvents. In certain instances, solubility in nonpolar organic solvents is desirable for labeling reactions involving a relatively nonpolar substrate.

SUMMARY OF THE INVENTION

Thus there remains a considerable need for improved compositions and methods that would allow convenient and effective labeling of a wide range of molecules in various applications. The present invention addresses this need and provides additional advantages.

Accordingly, the present invention provides fluorescent compounds which may have any or all of the following characteristics. In one aspect, labeled biomolecules prepared using fluorescent compounds of the invention show significantly reduced dimer formation. In other aspects, compounds and labeled biomolecules of the invention show other desirable properties such as higher water solubility, improved fluorescence quantum yield, improved photostability, relatively simple synthesis, improved specificity of the labeled conjugates.

Provided herein, in some embodiments, are compounds of Formula I:

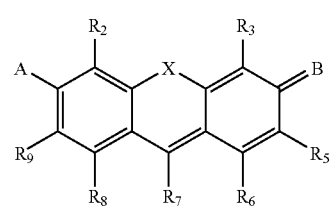

Formula Ia

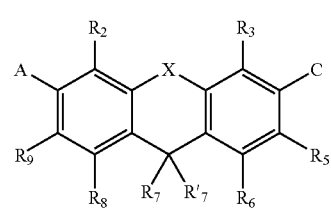

Formula Ib wherein:

X is O, S, or —C(CH$_3$)$_2$—;

A is —OR$_1$ or —NR$_1$R$_{1a}$;

B is =O or =N$^+$R$_4$R$_{4a}$;

C is —OR$_4$ or —NR$_4$R$_{4a}$;

R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^-$ and L-R$_x$; or at least one of R$_1$, R$_{1a}$, R$_4$, or R$_{4a}$ is an enzyme substrate or a protecting group;

R$_2$, R$_3$, R$_5$, R$_6$, R$_7$, R$_8$, and R$_9$ are each independently H, halogen, CN, alkyl, alkenyl, alkoxy, alkylthio, alkylamino, dialkylamino, alkylaminocarbonyl, dialkylaminocarbonyl, aryl, heteroaryl, -L-R$_x$, or a reactive sulfonamide; or one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, heteroalkyl, alkenyl, alkoxy, alkylthio, alkylamino, dialkylamino, alkylaminocarbonyl, dialkylaminocarbonyl, aryl, heteroaryl, -L-PO$_3^{2-}$, L-SO$_3-$, -L-R$_x$, or a reactive sulfonamide;

R$_7$' is H, OH, CN, or C$_1$-C$_6$ alkoxy; or R$_7$' in combination with R$_7$ forms a 5- or 6-membered spirolactone or spirosultone ring;

R$_x$ is a reactive group;

L is a bond or (Q)$_n$;

each Q is independently NR$_d$, S(O)$_t$, O, C(=X'), (C=X'), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two 0 are adjacent;

each X' is independently NR$_d$, S or O;

n is 1-20;

each R$_d$ is H, substituted or unsubstituted alkyl;

provided that the compound comprises at least one reactive sulfonamide.

In some embodiments, X is O. In other embodiments, A is —NR$_1$R$_{1a}$ and B is =N$^+$R$_4$R$_{4a}$. In still other embodiments, one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, heteroalkyl, alkenyl, alkoxy, alkylthio, alkylamino, dialkylamino, alkylaminocarbonyl, dialkylaminocarbonyl, aryl, heteroaryl, -L-PO$_3^{2-}$, -L-SO$_3^-$, -L-R$^x$, or a reactive sulfonamide.

In some embodiments of Formula I, the reactive sulfonamide moiety has a structure of Formula IIa:

Formula IIa

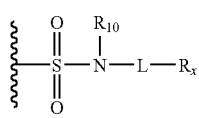

wherein:

R$_{10}$ is H or a substituted or unsubstituted C$_1$-C$_{12}$ alkyl; or

R$_{10}$ and L together with the nitrogen to which they are attached form a saturated or unsaturated ring.

In some embodiments, R$_{10}$ is H, sulfopropyl or sulfobutyl. In other embodiments, R$_x$ is an isothiocyanate, an isocyanate, a monochlorotriazine, a dichlorotriazine, a halogen-substituted pyridine, a halogen-substituted diazine, a phosphoramidite, a maleimide, an aziridine, a sulfonyl halide, an acid halide, a hydroxysuccinimidyl ester, a hydroxysulfosuccinimidyl ester, a pyrrole-2,5-dione, a tetrafluorophenol ester, an imido ester, a hydrazine, an azidonitrophenyl, an azide, an alkyne, a 3-(2-pyridyl dithio)-propionamide, a glyoxal or an aldehyde. For example, R$_x$ forms a covalent bond with an amino, a sulfhydryl or a hydroxy nucleophile. In some embodiments, R$_x$ is an activated carboxylic acid ester group. In other embodiments, the activated carboxylic acid ester group is an N-hydroxysuccinimide ester group.

In other embodiments, R$_2$, R$_3$, R$_5$ and R$_9$ is independently selected from the group consisting of H, halogen, —PO$_3^{2-}$, —SO$_3^-$ or unreactive sulfonamide, or

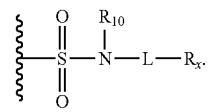

In some embodiments, R$_7$ is H, substituted or unsubstituted alkyl, or substituted or unsubstituted aryl. In some embodiments, R$_7$ is a phenyl substituted with —CO$_2^-$, carboxamide, —SO$_3^-$, chloro, fluoro or R$_x$.

In some embodiments, the compound of the invention has the structure of Formula IIIa Formula IIIa

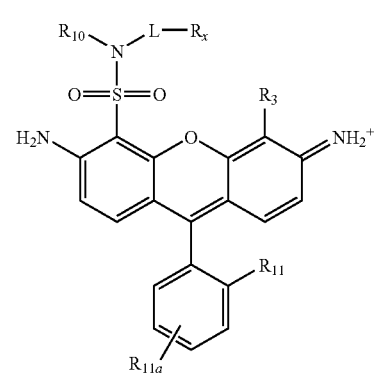

wherein:

R$_3$ is H, —SO$_3^-$, or an unreactive sulfonamide;

R$_{11}$ is —CO$_2^-$ or —SO$_3^-$; and

R$_{11a}$ is H, —SO$_3^-$, or an unreactive sulfonamide.

In some embodiments, R$_3$ is H or —SO$_3^-$; and L is Q$_n$, wherein at least four Q are —(CH$_2$CH$_2$O)—.

In some embodiments, a maximal fluorescence excitation wavelength of the compound of the invention is about 488 nm.

In some embodiments a compound of the invention has the structure of Formula IV:

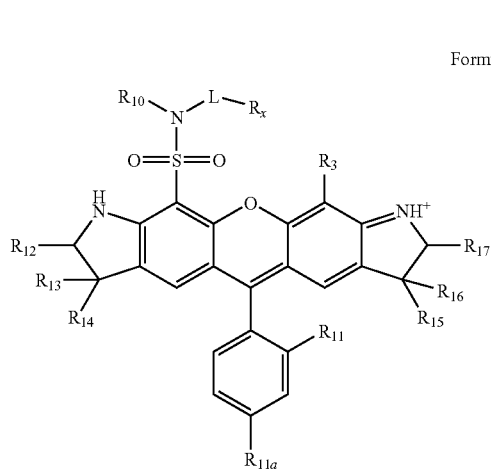

Formula IV wherein:
$R_3$ is H, —$SO_3^-$, or unreactive sulfonamide;
$R_{10}$ is H, sulfopropyl or sulfobutyl;
$R_{11}$ is —$CO_2^-$ or —$SO_3^-$;
$R_{11a}$ is H, —$SO_3^-$, or an unreactive sulfonamide; and
$R_{12}$, $R_{13}$, $R_{14}$, $R_{15}$, $R_{16}$ and $R_{17}$ are each independently H or methyl.

In some embodiments of the compound of the invention, a maximal fluorescence excitation wavelength of the compound is about 514 nm.

In other embodiments, a compound of the invention has a structure of Formula V:

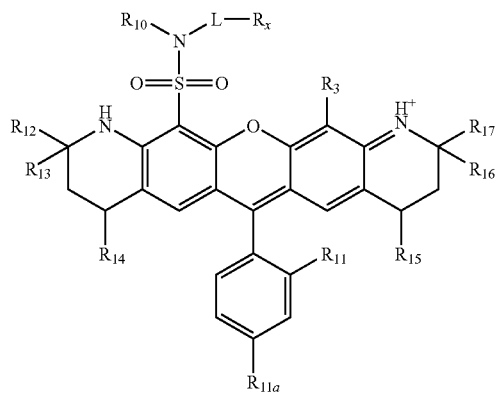

Formula V wherein:
$R_3$ is H, —$SO_3^-$, or unreactive sulfonamide;
$R_{10}$ is H, sulfopropyl or sulfobutyl;
$R_{11}$ is —$CO_2^-$ or —$SO_3^-$;
$R_{11a}$ is H, —$SO_3^-$, or an unreactive sulfonamide;
$R_{12}$, $R_{13}$, $R_{14}$, $R_{15}$, $R_{15}$ and $R_{17}$ are each independently H or methyl, and In some embodiments of the compound of the invention, a maximal fluorescence excitation wavelength of the compound is about 532 nm.

In other embodiments a compound of the invention has the structure of Formula VI:

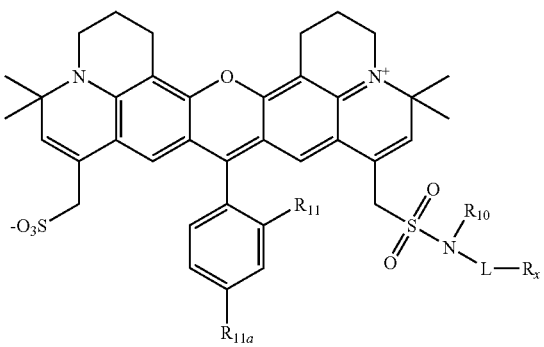

Formula VI wherein:
$R_{11}$ and $R_{11a}$ are each independently H, —$SO_3^-$, or unreactive sulfonamide;
$R_{10}$ is H, sulfopropyl or sulfobutyl;
L is a bond, or $Q_n$; wherein at least one Q is —$(CH_2CH_2O)$—; and
$R_x$ is a reactive group.

In some embodiments, a maximal fluorescence excitation wavelength of the compound is about 633 nm.

The invention also provides a compound of Formula VII:

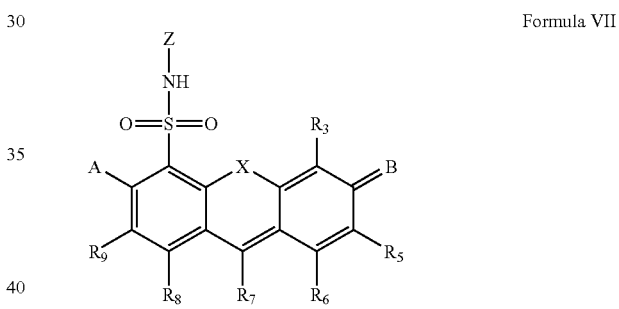

Formula VII wherein:
Z is a metal chelator;
X is O, S, or —$C(CH_3)_2$—;
A is —$OR_1$ or —$NR_1R_{1a}$;
B is =O or =$N^+R_4R_{4a}$;
C is ±—$OR_4$ or —$NR_4R_{4a}$;
$R_1$, $R_{1a}$, $R_4$, and $R_{4a}$ are each independently H or alkyl, unsubstituted or substituted with -L-$SO_3^-$, -L-$PO_3^{2-}$, a water-soluble polymer, or with -L-$R_x$; or one or more pair of $R_1$ and $R_{1a}$ or $R_4$ and $R_{4a}$ together with the nitrogen to which they are attached form a saturated or unsaturated ring optionally substituted by any of -L-$SO_3^-$, -L-$PO_3^{2-}$ and -L-$R_x$; or at least one of $R_1$, $R_{1a}$, $R_4$, or $R_{4a}$ is an enzyme substrate or a protecting group;
$R_3$, $R_5$, $R_6/R_7$, $R_8$, and $R_9$ are each independently H, halogen, CN, alkyl, alkenyl, alkoxy, alkylthio, alkylamino, dialkylamino, alkylaminocarbonyl, dialkylaminocarbonyl, aryl, heteroaryl, -L-$PO_3^{2-}$, -L-$SO_3^-$, -L-$R_x$, a reactive sulfonamide or a neutral or positively charged unreactive sulfonamide; or one or more pair of $R_3$ and $R_{4a}$, $R_4$ and $R_5$, $R_5$ and $R_6$, $R_8$ and $R_9$, or $R_9$ and $R_1$, together with the atoms to which they are attached form one or more fused saturated or unsaturated rings that are optionally substituted by at least one halogen, CN, alkyl, heteroalkyl, alkenyl, alkoxy, alkylthio, alkylamino, dialkylamino, alkylaminocarbonyl, dialkylaminocarbonyl, aryl, heteroaryl, -L-$PO_3^{2-}$, L-$SO_3^-$, -L-$R_x$, a reactive sulfonamide or a neutral or positively charged unreactive sulfonamide;

$R_x$ is a reactive group;

L is a bond or $(Q)_n$;

each Q is independently $NR_d$, $S(O)_t$, O, C(=X'), (C=X'), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two $NR_d$ are adjacent and no two 0 are adjacent;

each X' is independently $NR_d$, S or O;

n is 1-20; and each $R_d$ is H, substituted or unsubstituted alkyl.

In some embodiments, Z is a chelator for a target ion selected from $Ca^{2+}$, $Mg^{2+}$, $Zn^{2+}$, $Cu^{2+}$, $Ni^{2+}$, $Fe^{3+}$, $Na^+$, $K^+$, $Hg^{2+}$, $Pb^{2+}$, $Cd^{2+}$ and $As^{3+}$. In one embodiment, Z is a BAPTA-based $Ca^{2+}$ chelator.

Also provided is a method of detecting or quantitating the presence of a metal ion comprising:

a. incubating a sample with the compound of Formula VII:

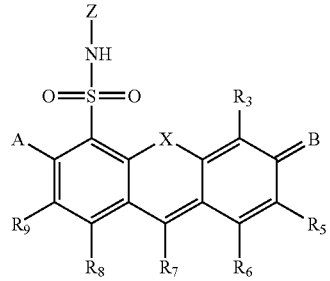

Formula VII wherein:

Z is a metal chelator;

X is O, S, or —C($CH_3$)$_2$—;

A is —$OR_1$, or —$NR_1R_{1a}$;

B is =O or =$N^+R_4R_{4a}$;

C is —$OR_4$ or —$NR_4R_{4a}$;

$R_1$, $R_{1a}$, $R_4$, and $R_{4a}$ are each independently H or alkyl, unsubstituted or substituted with -L-$SO_3^-$, -L-$PO_3^{2-}$, a water-soluble polymer, or with -L-$R_x$; or one or more pair of $R_1$ and $R_{1a}$ or $R_4$ and $R_{4a}$ together with the nitrogen to which they are attached form a saturated or unsaturated ring optionally substituted by any of -L-$SO_3^-$, -L-$PO_3^{2-}$ and -L-$R_x$; or at least one of $R_1$, $R_{1a}$, $R_4$, or $R_{4a}$ is an enzyme substrate or a protecting group;

$R_3$, $R_5$, $R_6$, $R_7$, $R_8$, and $R_9$ are each independently H, halogen, CN, alkyl, alkenyl, alkoxy, alkylthio, alkylamino, dialkylamino, alkylaminocarbonyl, dialkylaminocarbonyl, aryl, heteroaryl, -L-$PO_3^{2-}$, L-$SO_3^-$, -L-$R_x$, a reactive sulfonamide or a neutral or positively charged unreactive sulfonamide; or one or more pair of $R_3$ and $R_{4a}$, $R_4$ and $R_5$, $R_5$ and $R_6$, $R_8$ and $R_9$, or $R_9$ and $R_1$, together with the atoms to which they are attached form one or more fused saturated or unsaturated rings that are optionally substituted by at least one halogen, CN, alkyl, heteroalkyl, alkenyl, alkoxy, alkylthio, alkylamino, dialkylamino, alkylaminocarbonyl, dialkylaminocarbonyl, aryl, heteroaryl, -L-$PO_3^{2-}$, L-$SO_3^-$, -L-$R_x$, a reactive sulfonamide or a neutral or positively charged unreactive sulfonamide;

$R_x$ is a reactive group;

L is a bond or $(Q)_n$;

each Q is independently $NR_d$, $S(O)_t$, O, C(=X'), (C=X'), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two $NR_d$ are adjacent and no two 0 are adjacent;

each X' is independently $NR_d$, S or O;

n is 1-20; and each $R_d$ is H, substituted or unsubstituted alkyl; and b. determining a change in the fluorescence or optical properties of said compound, thereby ascertaining the presence or quantity of said metal ion.

In some embodiments, the change is an increase or decrease in absorbance or emission of said compound.

Alternatively, the change is a shift in the maximum absorbance or maximum emission wavelength of the compound.

The invention further provides a compound of Formula Ia or Ib:

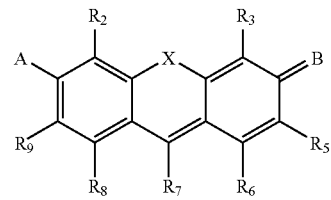

Formula Ia

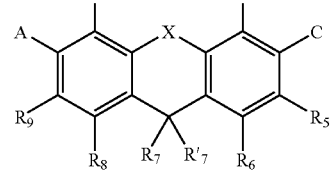

Formula Ib wherein:

X is O, S, or —C($CH_3$)$_2$—;

A is —$OR_1$, or —$NR_1R_{1a}$;

B is =O or =$N^+R_4R_{4a}$;

C is —$OR_4$ or —$NR_4R_{4a}$;

$R_1$, $R_{1a}$, $R_4$, and $R_{4a}$ are each independently H or alkyl, unsubstituted or substituted with -L-$SO_3^-$, -L-$PO_3^{2-}$, a water-soluble polymer, or with -L-$R_x$; or one or more pair of $R_{1z}$ and $R_{1a}$ or $R_4$ and $R_{4a}$ together with the nitrogen to which they are attached form a saturated or unsaturated ring optionally substituted by any of -L-$SO_3^-$, -L-$PO_3^2$ and -L-$R_x$; or at least one of $R_1$, $R_{1a}$, $R_4$, or $R_{4a}$ is an enzyme substrate or a protecting group;

$R_2$, $R_3$, $R_5$, $R_6$, $R_7$, $R_8$, and $R_9$ are each independently H, halogen, CN, alkyl, alkenyl, alkoxy, alkylthio, alkylamino, dialkylamino, alkylaminocarbonyl, dialkylaminocarbonyl, aryl, heteroaryl, -L-$SO_3^-$, -L-$PO_3^{2-}$, -L-$R_x$, a reactive sulfonamide, or a neutral or positively charged unreactive sulfonamide; or one or more pair of $R_2$ and $R_{1a}$, $R_3$ and $R_{4a}$, $R_4$ and $R_5$, $R_5$ and $R_6$, $R_8$ and $R_9$, or $R_9$ and $R_1$, together with the atoms to which they are attached form one or more fused saturated or unsaturated rings that are optionally substituted by at least one halogen, CN, alkyl, heteroalkyl, alkenyl, alkoxy, alkylthio, alkylamino, dialkylamino, alkylaminocarbonyl, dialkylaminocarbonyl, aryl, heteroaryl, -L-$PO_3^{2-}$, L-SO$_3^-$, -L-R$_x$, a reactive sulfonamide, or a neutral or positively charged unreactive sulfonamide;

R$_7$' is H, OH, CN, or C$_1$-C$_6$ alkoxy; or R$_7$' in combination with R$_7$ forms a 5- or 6-membered spirolactone or spirosultone ring;

R$_x$ is a reactive group;

L is a bond or (Q)$_n$;

each Q is independently NR$_4$, S(O)$_t$, O, C(=X'), (C=X'), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;

each X' is independently NR$_d$, S or O;

n is 1-20;

each R$_d$ is H, substituted or unsubstituted alkyl;

provided that the compound comprises at least one neutral or positively charged unreactive sulfonamide.

In one embodiment, the unreactive sulfonamide has a molecular weight of less than about 350. In another embodiment, the unreactive sulfonamide moiety has a structure of Formula IIb:

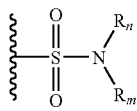

Formula IIb wherein R$_m$ and R$_n$ are each independently H, alkyl, or heteroalkyl; wherein the unreactive sulfonamide moiety carries a zero or positive charge.

In some embodiments, R$_m$ and R$_n$ are each independently H or a C$_1$-C$_{12}$ alkyl. In other embodiments, the compound of the invention has a structure of Formula IIIb:

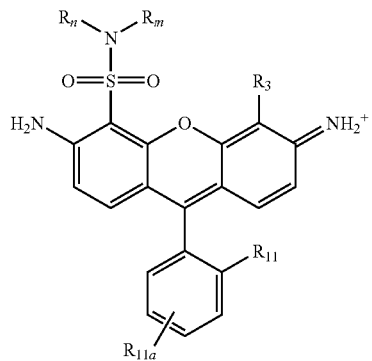

Formula IIIb wherein:

R$_3$ is —SO$_3$;

R$_m$ and R$_n$ are each independently H, alkyl, or heteroalkyl;

R$_{11}$ is —CO$_2^-$ or —SO$_3^-$; and

R$_{11a}$ is H, —CO2-, —SO$_3^-$, or -L-R$_x$,

Also provided herein is a method of preparing a labeled biomolecule comprising reacting a biomolecule with a compound having a structure of Formula VIIIa or VIIIb:

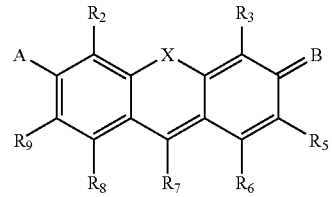

Formula VIIIa or VIIIba

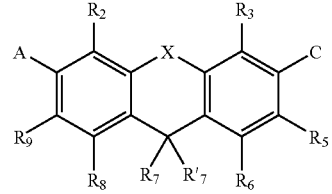

Formula VIIIa or VIIIbb wherein:

X is O, S, or —C(CH$_3$)$_2$—;

A is —OR$_1$ or —NR$_1$R$_{1a}$;

B is =O or =N$^+$R$_4$R$_{4a}$;

C is —OR$_4$ or —NR$_4$R$_{4a}$;

R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$, or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;

R$_2$, R$_3$, R$_5$, R$_6$, R$_7$, R$_8$, and R$_9$ are each independently H, halogen, CN, alkyl, alkenyl, alkoxy, alkylthio, alkylamino, dialkylamino, alkylaminocarbonyl, dialkylaminocarbonyl, aryl, heteroaryl, -L-PO$_3^{2-}$, L-SO$_3^-$, -L-R$_x$, a reactive sulfonamide or an unreactive sulfonamide; or one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, heteroalkyl, alkenyl, alkoxy, alkylthio, alkylamino, dialkylamino, alkylaminocarbonyl, dialkylaminocarbonyl, aryl, heteroaryl, -L-R$_x$, a reactive sulfonamide or an unreactive sulfonamide;

R$_7$' is H, OH, CN, or C$_1$-C$_6$ alkoxy; or R$_7$' in combination with R$_7$ forms a 5- or 6-membered spirolactone or spirosultone ring;

R$_x$ is a reactive group;

L is a bond or (Q)$_n$;

each Q is independently NR$_d$, S(O)$_t$, O, C(=X'), (C=X'), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;

each X' is independently NR$_d$, S or O;

n is 1-20;

each R$_d$ is H, substituted or unsubstituted alkyl;

provided that the compound comprises at least one reactive group.

Also provided herein is a kit comprising:

i) a compound of any one of the formulae provided herein; ii) a buffer; iii) materials or devices for purifying conjugation products; and iv) instructions instructing the use of the compound.

Provided herein is a biomolecule comprising a label having a structure of a compound of the invention wherein the at least one reactive moiety of the compounds has undergone a reaction which attaches the label to the biomolecule.

In some embodiments, the biomolecule comprises a polynucleotide. In some embodiments, the biomolecule comprises a polypeptide. In some embodiments, the polypeptide further comprises an antigen binding site. In some embodiments, the polypeptide is a whole immunoglobulin. In some embodiments, the polypeptide is a Fab fragment.

An immunoglobin comprising a label having a structure of the invention wherein at least one reactive moiety of the compound has undergone a reaction which attaches the label to the immunoglobin, wherein the immunoglobin is an antibody that binds specifically to an antigen on a cancer cell.

In some embodiments, the immunoglobin is an antibody that binds to erb2.

In some embodiments, the method of labeling a biomolecule comprises reacting a compound of the invention comprising a reactive group and a substrate biomolecule under conditions sufficient to effect crosslinking between the compound and the substrate biomolecule. In some embodiments, the substrate biomolecule is a protein, polypeptide, a polynucleotide, a carbohydrate, a lipid, a metal chelator or a combination thereof. In some embodiments, the substrate biomolecule is a polynucleotide.

Provided herein a method for labeling a cell within a population of cells whereby the cell is differentially labeled relative to neighboring cells within the population, the method comprising contacting the cell with a labeled biomolecule, wherein the biomolecule comprises a targeting moiety that binds to a binding partner that is indicative of the cell, and thereby differentially labeling the cell relative to neighboring cells within the population.

In some embodiments, the method further comprises the step of imaging the cell, the imaging step comprising:
 i) directing exciting wavelength to the cell; and
 ii) detecting emitted fluorescence from the cell.

In some embodiments, the labeling takes place in vitro. In some embodiments, the labeling takes place in vivo.

Provided herein is an immunoglobulin labeled with a fluorescent compound of the invention comprising a fluorophore that has an absorption maximal wavelength of about 488 nm.

Provided herein is an immunoglobulin labeled with a fluorescent compound of the invention comprising a fluorophore that has an absorption maximal wavelength of about 514 nm.

Provided herein is an immunoglobulin labeled with a fluorescent compound of the invention comprising a fluorophore that has an absorption maximal wavelength of about 532 nm.

Provided herein is an immunoglobulin labeled with a fluorescent compound of the invention comprising a fluorophore that has an absorption maximal wavelength of about 633 nm.

In some embodiments, the immunoglobulin retains binding specificity to a target upon conjugation to the fluorescent compound. In some embodiments, the immunoglobin is an antibody that binds specifically to an antigen on a cancer cell. In some embodiments, the antibody binds to erb2. In some embodiments, the immunoglobulin comprises a fluorescent compound of Formula I.

Provided herein is a method of labeling a polypeptide comprising: forming a complex that comprises the polypeptide and a binding agent, wherein the binding agent comprises a fluorescent label of the invention comprising a reactive moiety, wherein the at least one reactive moiety of the fluorescent label has undergone a reaction which attaches the label to the binding agent.

In some embodiments the binding agent is an antibody.

In some embodiments of the method the complex comprises (a) a primary antibody that binds to the polypeptide, and (b) the binding agent which functions as a secondary antibody exhibiting binding capability to the primary antibody.

In some embodiments, the labeling occurs on a solid substrate.

In some embodiments, the complex yields a signal to noise ratio greater than about 100, wherein the signal to noise ratio is calculated by the formula:

(fluorescent signal from a complex comprising the polypeptide bound by a primary antibody which in turn is bound to the binding agent)/(fluorescent signal from a mixture of the polypeptide, an isotype control primary antibody and the binding agent).

In some embodiments, the complex yields a signal to noise ratio greater than about 250, wherein the signal to noise ratio is calculated by the formula:

(fluorescent signal from a complex comprising the polypeptide bound by a primary antibody which in turn is bound to the binding agent)/(fluorescent signal from a mixture of the polypeptide, an isotype control primary antibody and the binding agent).

In some embodiments, the complex yields a signal to noise ratio greater than about 270, wherein the signal to noise ratio is calculated by the formula:

(fluorescent signal from a complex comprising the polypeptide bound by a primary antibody which in turn is bound to the binding agent)/(fluorescent signal from a mixture of the polypeptide, an isotype control primary antibody and the binding agent).

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
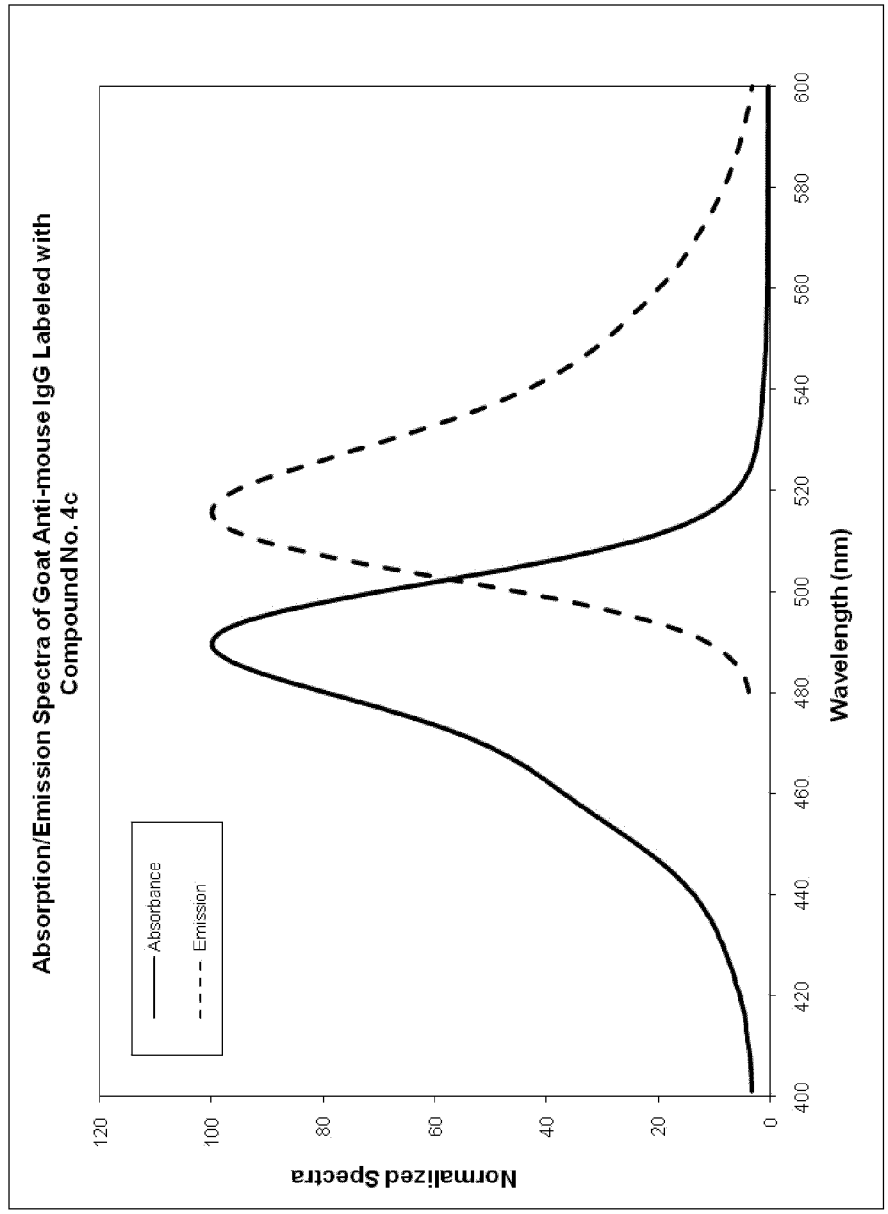
FIG. 1 is a graphical representation showing the absorption and emission spectra of compound No. 4c conjugated to goat anti-mouse IgG (5.3 DOL) in PBS (Example 26). The absorption spectrum shows only a single peak, indicating a lack of dye aggregation. Furthermore, the absorption peak wavelength is very close to the 488 nm argon ion laser line.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The present invention discloses fluorescent compounds comprising at least one reactive sulfonamide group. Such compounds may have desirable properties such as restricted intramolecular mobility, increased fluorescence quantum yield, decreased aggregation, increased solubility in e.g., non-polar organic solvents, decreased quenching and increased in vivo and in vitro stability. The compounds may be used for labeling molecules and biomolecules such as polypeptides, polynucleotides and/or metal chelators and are suitable for use in a wide range of applications, including diagnostic and imaging systems.

Fluorescent compounds and labeled molecules of the invention may exhibit reduced aggregation. Dye aggregation is often seen as a major contributing factor to fluorescence quenching. Prevention of aggregation in the present invention may be achieved without the use of an excessive number of negatively charged sulfonate groups. This in turn may aid in the labeling of biomolecules such as proteins because the labeled protein may have an isoelectric point comparable to that of the substrate protein, and may thereby better maintain its biological specificity. The use of sulfonamide groups aids in decreasing the negative charge on the dyes. Accordingly, labeled proteins, such as labeled antibodies, of the invention may have a better signal-to-noise ratio in cellular staining.

In some aspects, the presence of sulfonamide moieties on the fluorophores of the compounds disclosed herein also aids in increasing the solubility of the dyes in non-polar organic solvents. The enhanced solubility in non-polar solvents allows for the labeling of relatively non-polar substrates. The dyes disclosed herein may also increase the fluorescence quantum yield of the fluorescent group. In some aspects, the presence of a sulfonamide moiety shifts the excitation or absorption wavelength of a fluorescent dye to a wavelength at or near the wavelength of a common laser line (e.g, 488 nm, 514 nm, 532 nm and 633 nm), resulting in more efficient fluorescence excitation. Furthermore, the compounds and labeled molecules of the invention may exhibit higher photostability and resistance to bleaching of the fluorescent group.

DEFINITIONS

The compounds of the present invention may have asymmetric centers, chiral axes, and chiral planes (as described in: E. L. Eliel and S. H. Wilen, Stereo-chemistry of Carbon Compounds, John Wiley & Sons, New York, 1994, pages 1119 1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted.

When any variable (e.g. $R_x$, L, Q) occurs more than one time in any constituent, its definition on each occurrence is independent at every other occurrence. Combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only. Substitution of a ring by a substituent generally allows the substituent to be a cyclic structure fused to the ring.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent", and can include two, three, four, five or more substituents.

As used herein, "alkyl" is intended to include both branched, straight-chain, and cyclic saturated aliphatic hydrocarbon groups. Alkyl groups specifically include methyl, ethyl, propyl, butyl, pentyl, hexyl, heptyl, octyl, nonyl, decyl, and so on, as well as cycloalkyls such as cyclopropyl, cyclobutyl, cyclopentyl, cyclohexyl, tetrahydronaphthalene, methylenecylohexyl, and so on. For example, an alkyl chain designated as $C_1$-$C_{20}$ may have from 1 to 20 carbon atoms. "Alkoxy" represents an alkyl group attached through an oxygen bridge.

The term "alkenyl" refers to a non-aromatic hydrocarbon group, straight, branched or cyclic, containing at least one carbon to carbon double bond. Alkenyl groups include, but are not limited to, ethenyl, propenyl, butenyl and cyclohexenyl. For example, an alkenyl chain designated as $C_2$-$C_{20}$ may have from 1 to 20 carbon atoms. The straight, branched or cyclic portion of the alkenyl group may contain double bonds and may be substituted if a substituted alkenyl group is indicated.

The term "alkynyl" refers to a hydrocarbon group, straight, branched or cyclic, containing at least one carbon to carbon triple bond. Alkynyl groups include, but are not limited to, ethynyl, propynyl and butynyl. For example, an alkynyl chain designated as $C_2$-$C_{20}$ may have from 2 to 20 carbon atoms.

The straight, branched or cyclic portion of the alkynyl group may contain triple bonds and may be substituted if a substituted alkynyl group is indicated.

As used herein, "aryl" is intended to mean any stable monocyclic or polycyclic carbon ring of up to 7 atoms in each ring, wherein at least one ring is aromatic. Examples of such aryl elements include phenyl, naphthyl, tetrahydronaphthyl, indanyl, biphenyl, phenanthryl, anthryl or acenaphthyl. For example, an aryl group may be a 6-carbon monocyclic or 10-carbon bicyclic aromatic ring system wherein 0, 1, 2, 3, or 4 atoms of each ring may be substituted by a substituent. In cases where the aryl substituent is bicyclic and one ring is non-aromatic, it is understood that attachment is via the aromatic ring.

The term "heteroaryl", as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to imidazolyl, benzimidazolyl, acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, tetrahydroquinoline, xanthenyl, and coumarinyl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing at least one heteroatom which is O, N or S. This definition includes bicyclic groups. "Heterocyclyl" therefore includes the above mentioned heteroaryls, as well as dihydro and tetrahydro analogs thereof. Further examples of "heterocyclyl" include, but are not limited to the following: benzimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

The alkyl, alkenyl, alkynyl, cycloalkyl, aryl, heteroaryl and heterocyclyl substituents may be unsubstituted or unsubstituted, unless specifically defined otherwise. For example, an alkyl group may be substituted with one or more substituents selected from OH, oxo, halo, alkoxy, dialkylamino, —$PO_3^-$, —$SO_3^{2-}$, —$CO_2$, a reactive group, or heterocyclyl, such as morpholinyl or piperidinyl.

The terms "halo" or "halogen" are intended to include chloro, fluoro, bromo and iodo groups.

The term "aromatic" is used in its usual sense, including unsaturation that is essentially delocalized across multiple bonds, such as around a ring.

The term "substituent" refers to an atom, radical or chemical group which replaces a hydrogen in a substituted chemical group, radical, molecule, moiety or compound. In some cases, "substituent" may refer to an atom, radical or chemical group which replaces a lone-pair electron on a nitrogen. In such cases, the substituent may alternatively be referred to as a quarternizing group or quarternizing substituent.

Unless otherwise stated, the term "radical", as applied to any molecule or compound, is used to refer to a part, fragment or group of the molecule or compound rather than to a "free radical". A radical may be linked to another moiety through a covalent bond.

The term "reactive group" refers to a chemical moiety capable of reacting with a reaction partner on a substrate or substrate molecule to form a covalent bond. A compound of the invention can be used to label a wide variety of molecules or substrates that contain a suitable reaction partner or are derivatized to contain a suitable reaction partner. "Reactive group" and "reaction partner" may refer to groups on a compound of the present invention, or to groups on a molecule to be labeled. Here, by way of convenience, but not limitation, a bond-forming group on a compound will generally be referred to as a reactive group and a bond-forming group on the substrate molecule will generally be referred to as a reaction partner. "Reaction substrate", "substrate" and "reaction partner" are used interchangeably throughout this document.

The term "reactive sulfonamide group" refers to any sulfonamide group that is attached by a bond or via a linking moiety to a reactive group.

The term "unreactive sulfonamide group" refers to any sulfonamide group that is not attached to a reactive group.

In general, linking moieties (e.g. Q) may be any group connecting two moieties, such as fluorophores, sulfonamide groups and/or reactive groups to each other or to any other group included in the compound of the invention. Synthetic accessibility and convenience may generally dictate the nature of each linking moiety. In some embodiments, a linking moiety is a group containing about 1-100 atoms and formed of one or more chemical bonds selected such that the group is a stable moiety. In other embodiments, a linking moiety is formed of one or more carbon-hydrogen, carbon-nitrogen, carbon-oxygen, carbon-sulfur, carbon-phosphorus, nitrogen-hydrogen, sulfur-hydrogen, phosphorus-hydrogen, sulfur-oxygen, sulfur-nitrogen, sulfur-phosphorus, phosphorus-oxygen, phosphorus-nitrogen and oxygen-nitrogen bonds, wherein such bonds may be single, double, triple, aromatic and heteroaromatic bonds selected such that the linking moiety is stable. A linking moiety can be, for example, a divalent alkyl radical. Alternatively, a linking moiety may be an alkyl group comprising additional ether, amine, amide, ester, sulfonyl, thioether, carboxamide, sulfonamide, hydrazide or morpholino, aryl and heteroaryl groups.

Linking moieties are generally formed of about 1-100 atoms. In some embodiments, linking moieties are formed of 1-50 non-hydrogen atoms as well as additional hydrogen atoms. Such atoms may be, for example, C, N, O, P or S. In other embodiments, a linker moiety connecting two groups comprises 1 to 50 consecutive bonds between the groups. Some linker moieties may have 1 to 40, 1 to 30, 1 to 20, 1 to 10, 1 to 5, 5 to 25, or 5 to 20 such consecutive bonds.

Non-limiting exemplary linking moieties are illustrated below:

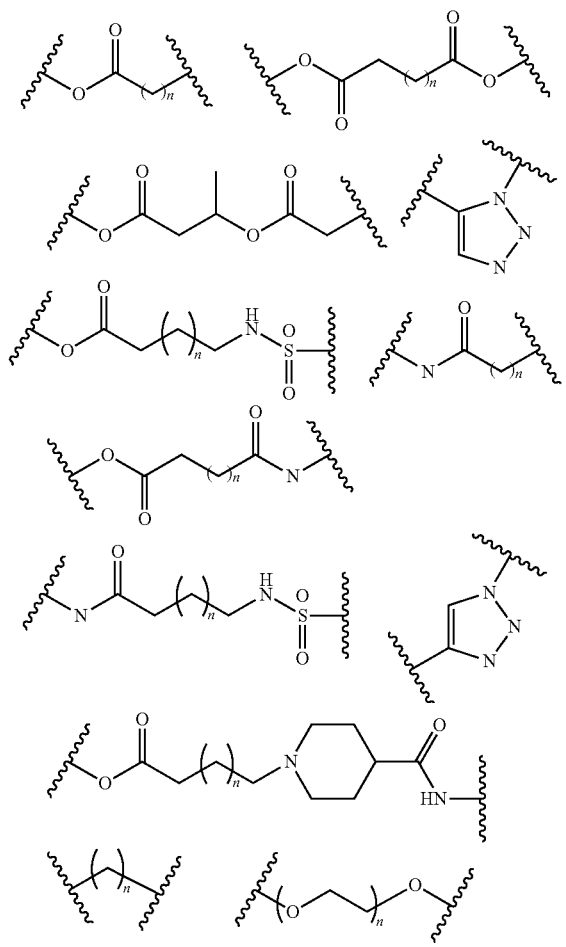

In the above image, n represents a number of repeating methylene units which can be varied such as to provide a desired length of the linker. Typically, n ranges from 1 to about 50. Some linkers will have an n of 1 to 40, 1 to 30, 1 to 20, 1 to 10, 1 to 5, 5 to 30, 5 to 20, or 5 to 15.

The terms "polynucleotides", "nucleic acids", "nucleotides", "probes" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. "Polynucleotide" may also be used to refer to peptide nucleic acids (PNA), locked nucleic acids (LNA), threofuranosyl nucleic acids (TNA) and other unnatural nucleic acids or nucleic acid mimics. Other base and backbone modifications known in the art are encompassed in this definition. See, e.g. De Mesmaeker et al (1997) Pure & Appl. Chem., 69, 3, pp 437-440.

The terms "polypeptide", "peptide" and "protein" are used interchangeably herein to refer to polymers of amino acids of any length. The polymer may be linear, cyclic, or branched, it may comprise modified amino acids, and it may be interrupted by non-amino acids. The terms also encompass amino acid polymers that have been modified, for example, via sulfonation, glycosylation, lipidation, acetylation, phosphorylation, iodination, methylation, oxidation, proteolytic processing, phosphorylation, prenylation, racemization, selenoylation, transfer-RNA mediated addition of amino acids to proteins such as arginylation, ubiquitination, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The term "antibody" as used herein refers to immunoglobulin molecules and immunologically active portions of immunoglobulin molecules, i.e., molecules that contain an antigen-binding site which specifically binds ("immunoreacts with") an antigen. Structurally, the simplest naturally occurring antibody (e.g., IgG) comprises four polypeptide chains, two heavy (H) chains and two light (L) chains interconnected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. It has been shown that the antigen binding function of an antibody can be performed by fragments of a naturally-occurring antibody. These fragments are collectively termed "antigen-binding units". Antigen binding units can be broadly divided into "single-chain" ("Sc") and "non-single-chain" ("Nsc") types based on their molecular structures.

Also encompassed within the terms "antibodies" are immunoglobulin molecules of a variety of species origins including invertebrates and vertebrates. The term "human" as applies to an antibody or an antigen binding unit refers to an immunoglobulin molecule expressed by a human gene or fragment thereof. The term "humanized" as applies to a non-human (e.g. rodent or primate) antibodies are hybrid immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance and minimize immunogenicity when introduced into a human body. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin.

The term "stable" refers to compositions and compounds which have sufficient chemical stability to survive isolation from a reaction mixture to a useful degree of purity for use in a desired application.

The terms "fluorescent group", "fluorophore", "dye" or "fluorescent group" refer interchangeably to molecules, groups or radicals which are fluorescent. The term "fluorescent" as applied to a molecule of compound is used to refer to the property of the compound of absorbing energy (such as UV, visible or IR radiation) and re-emitting at least a fraction of that energy as light over time. Fluorescent groups, compounds or fluorophores include, but are not limited to discrete compounds, molecules, proteins and macromolecular complexes. Fluorophores also include compounds that exhibit long-lived fluorescence decay such as lanthanide ions and lanthanide complexes with organic ligand sensitizers.

A "subject" as used herein refers to a biological entity containing expressed genetic materials. The biological entity is in various embodiments, a vertebrate. In some embodiment, the biological entity is a mammal. In other embodiments, the subject is a biological entity which comprises a human.

A "control" is an alternative subject or sample used in an experiment for comparison purposes. A control can be "positive" or "negative". For example, where the purpose of the experiment is to detect a differentially expressed transcript or polypeptide in cell or tissue affected by a disease of concern, it is generally preferable to use a positive control (a subject or a sample from a subject, exhibiting such differential expression and syndromes characteristic of that disease), and a negative control (a subject or a sample from a subject lacking the differential expression and clinical syndrome of that disease.

The term "FRET" refers to fluorescence resonance energy transfer. In the present invention, FRET refers to energy transfer processes occurring between at least two fluorescent compounds, between a fluorescent compound and a non-fluorescent component or between a fluorescent component and a non-fluorescent component.

A "binding agent" is a molecule that exhibits binding selectivity towards a binding partner or a target molecule to which it binds. A binding agent may be a biomolecule such as a polypeptide such as an antibody or protein, polypeptide-based toxin, amino acid, nucleotide, polynucleotides including DNA and RNA, lipids, and carbohydrates, or a combination thereof. A binding agent may also be a hapten, drug, ion-complexing agent such as metal chelators, microparticles, synthetic or natural polymers, cells, viruses, or other fluorescent molecules including the dye molecule according to the invention.

A "targeting moiety" is the portion of the binding agent that binds to a binding partner. A targeting moiety may be, without limitation, a nucleotide sequence within a polynucleotide that selectively binds to another polynucleotide or polypeptide. Another nonlimiting example of a targeting moiety may be a polypeptide sequence within a larger polypeptide sequence which binds specifically to a polynucleotide sequence or a second polypeptide sequence. A targeting moiety may be a small molecule or structural motif which will bind to a protein receptor, another small molecule motif, or complexing agent, without limitation. The selective binding may be a specific binding event.

A "binding partner" is a molecule or particle which is bound by the targeting moiety. It can be a cell, virus, fragment of a cell, antibody, fragment of an antibody, peptide, protein, polynucleotide, antigen, small molecule, or a combination thereof. It may be bound selectively or specifically by the binding agent.

The term "signal to noise ratio" of fluorescence as referred to herein in the context of a polypeptide-antibody complex, is the ratio of (fluorescent signal from a complex comprising a polypeptide bound by a primary antibody which in turn is bound to a binding agent labeled with a compound of the invention)/(fluorescent signal from a mixture of the polypeptide, an isotype control primary antibody, and the labeled binding agent).

"Degree of labeling" or "DOL" as used herein refers to the number of dye molecules which are attached per target molecule (including but not limited to polypeptide and polynucleotide). For example, a single dye molecule per a polypeptide such as an antibody represents a 1.0 degree of labeling (DOL). If more than one dye molecule, on average, reacts with and is crosslinked to a polypeptide such as an antibody, the degree of labeling is greater than 1 and may further be a number other than a whole integer. The higher the number of DOL, the greater extent of labeling.

"Intracellular" as used herein refers to the presence of a given molecule in a cell. An intracellular molecule can be present within the cytoplasm, attached to the cell membrane, on the surface of an organelle, or within an organelle of a cell.

"Substrate" or "solid substrate" when used in the context of a reaction surface refers to the material that certain interaction is assayed. For example, a substrate in this context can be a surface of an array or a surface of microwell. It may also be a solid such as a polymer which does not form a specific shape but has attachment points on its surface. In some cases, "substrate" may refer to an enzyme substrate, which is a molecule or biomolecule capable of being chemically transformed by an enzyme.

The terms "wavelength of maximum excitation" and "maximal fluorescence excitation wavelength" are used herein interchangeably. These terms refer to the wavelength at which a fluorescent compound is excited to emit maximal fluorescence. The term "absorption maximal wavelength" as applied to a dye refers to the wavelength at which a fluorescent dye or nonfluorescent dye has maximal absorption. A fluorescent dye has a "maximal fluorescence emission wavelength" which is the wavelength at which the dye most intensely fluoresces. When a single wavelength is referred to for any dye, it refers to the maximal wavelength of excitation, absorption, or emission, according to the context of the term, for example, an absorption wavelength refers to the wavelength at which the compound has maximal absorption, and an emission wavelength refers to the wavelength at which the dye most intensely fluoresces.

Compounds of the Invention:

Provided herein, in some embodiments, are compounds of Formula Ia and Ib:

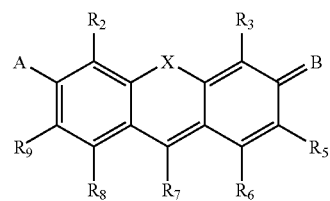

Formula Ia

-continued

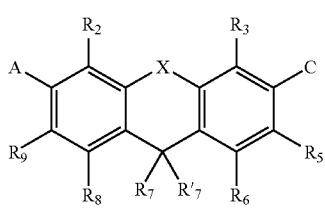

Formula Ib wherein:

X is O, S, or —C(CH$_3$)$_2$—;

A is —OR$_1$ or —NR$_1$R$_{1a}$;

B is =O or =N$^+$R$_4$R$_{4a}$;

C is —OR$_4$ or —NR$_4$R$_{4a}$;

R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^+$, -L-PO$_3^{2-}$ and -L-R$_x$; or at least one of R$_1$, R$_{1a}$, R$_4$, or R$_{4a}$ is an enzyme substrate or a protecting group;

R$_2$, R$_3$, R$_5$, R$_6$, R$_7$, R$_8$, and R$_9$ are each independently H, halogen, CN, alkyl, alkenyl, alkoxy, alkylthio, alkylamino, dialkylamino, alkylaminocarbonyl, dialkylaminocarbonyl, aryl, heteroaryl, -L-PO$_3^{2-}$, L-SO$_3^-$, -L-R$_x$, or a reactive sulfonamide; or one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, heteroalkyl, alkenyl, alkoxy, alkylthio, alkylamino, dialkylamino, alkylaminocarbonyl, dialkylaminocarbonyl, aryl, heteroaryl, -L-PO$_3^{2-}$, L-SO$_3^-$, -L-R$_x$, or a reactive sulfonamide;

R$_7$' is H, OH, CN, or C$_1$-C$_6$ alkoxy; or R$_7$' in combination with R$_7$ forms a 5- or 6-membered spirolactone or spirosultone ring;

R$_x$ is a reactive group;

L is a bond or (Q)$_n$;

each Q is independently NR$_d$, S(O)$_t$, O, C(=X'), (C=X'), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two 0 are adjacent;

each X' is independently NR$_d$, S or O;

n is 1-20;

each R$_d$ is H, substituted or unsubstituted alkyl; provided that the compound comprises at least one reactive sulfonamide.

In some embodiments, X is O. In other embodiments, A is —NR$_1$R$_{1a}$ and B is =N$^+$R$_4$R$_{4a}$. In still other embodiments, one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, heteroalkyl, alkenyl, alkoxy, alkylthio, alkylamino, dialkylamino, alkylaminocarbonyl, dialkylaminocarbonyl, aryl, heteroaryl, -L-PO$_3^{2-}$, -L-SO$_3^-$, -L-R$_x$, or a reactive sulfonamide.

In some embodiments of Formula Ia or Ib, the reactive sulfonamide moiety has a structure of Formula IIa:

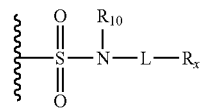

Formula IIa wherein:

R$_{10}$ is H or a substituted or unsubstituted C$_1$-C$_{12}$ alkyl; or R$_{10}$ and L together with the nitrogen to which they are attached form a saturated or unsaturated ring.

In some embodiments, R$_{10}$ is H, sulfopropyl or sulfobutyl. In other embodiments, R$_x$ is an isothiocyanate, an isocyanate, a monochlorotriazine, a dichlorotriazine, a halogen-substituted pyridine, a halogen-substituted diazine, a phosphoramidite, a maleimide, an aziridine, a sulfonyl halide, an acid halide, a hydroxysuccinimidyl ester, a hydroxysulfosuccinimidyl ester, a pyrrole-2,5-dione, a tetrafluorophenol ester, an imido ester, a hydrazine, an azidonitrophenyl, an azide, an alkyne, a 3-(2-pyridyl dithio)-propionamide, a glyoxal or an aldehyde. For example, R$_x$ forms a covalent bond with an amino, a sulfhydryl or a hydroxy nucleophile. In some embodiments, R$_x$ is an activated carboxylic acid ester group. In other embodiments, the activated carboxylic acid ester group is an N-hydroxysuccinimide ester group.

In other embodiments, R$_2$, R$_3$, R$_5$ and R$_9$ is independently selected from the group consisting of H, halogen, —PO$_3^{2-}$, —SO$_3^-$ or unreactive sulfonamide, or

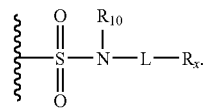

In some embodiments, R$_7$ is H, substituted or unsubstituted alkyl, or substituted or unsubstituted aryl. In some embodiments, R$_7$ is a phenyl substituted with —CO$_2$, carboxamide, —SO$_3^-$, chloro, fluoro or R$_x$.

In some embodiments, the compound of the invention has the structure of Formula IIIa:

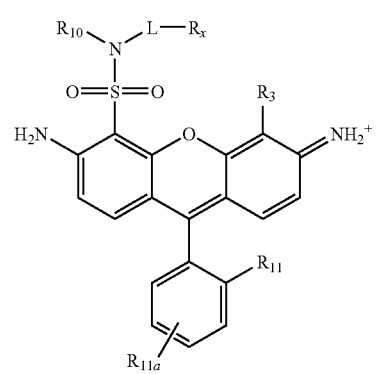

Formula IIIa wherein:

R$_3$ is H, —SO$_3^-$, or an unreactive sulfonamide;

R$_{11}$ is —CO$_2$ or —SO$_3^-$; and

R$_{11a}$ is H, —SO$_3^-$, or an unreactive sulfonamide.

In some embodiments a compound of the invention has the structure of Formula IV:

Formula IV wherein:
$R_3$ is H, —$SO_3^-$, or unreactive sulfonamide;
$R_{10}$ is H, sulfopropyl or sulfobutyl;
$R_{11}$ is —$CO_2$ or —$SO_3^-$;
$R_{11a}$ is H, —$SO_3^-$, or an unreactive sulfonamide; and
$R_{12}$, $R_{13}$, $R_{14}$, $R_{15}$, $R_{16}$ and $R_{17}$ are each independently H or methyl.

In other embodiments, a compound of the invention has a structure of Formula V:

Formula V wherein:
$R_3$ is H, —$SO_3^-$, or unreactive sulfonamide;
$R_{10}$ is H, sulfopropyl or sulfobutyl;
$R_{11}$ is —$CO_2$ or —$SO_3^-$;
$R_{11a}$ is H, —$SO_3^-$, or an unreactive sulfonamide;
$R_{12}$, $R_{13}$, $R_{14}$, $R_{15}$, $R_{16}$ and $R_{17}$ are each independently H or methyl, and In other embodiments a compound of the invention has the structure of Formula VI:

Formula VI wherein:
$R_{11}$ and $R_{11a}$ are each independently H, —$SO_3^-$, or unreactive sulfonamide;
$R_{10}$ is H, sulfopropyl or sulfobutyl;
L is a bond, or $Q_n$; wherein at least one Q is —($CH_2CH_2O$)—; and
$R_x$ is a reactive group.

The invention further provides a compound of Formula Ia or Ib:

Formula Ia

Formula Ib wherein:
X is O, S, or —$C(CH_3)_2$—;
A is —$OR_1$ or —$NR_1R_{1a}$;
B is =O or =$N^+R_4R_{4a}$;
C is —$OR_4$ or —$NR_4R_{4a}$;
$R_1$, $R_{1a}$, $R_4$, and $R_{4a}$ are each independently H or alkyl, unsubstituted or substituted with -L-$SO_3^-$, -L-$PO_3^{2-}$, a water-soluble polymer, or with -L-$R_x$; or one or more pair of $R_1$ and $R_{1a}$ or $R_4$ and $R_{4a}$ together with the nitrogen to which they are attached form a saturated or unsaturated ring optionally substituted by any of -L-$SO_3^-$, -L-$PO_3^2$ and -L-$R_x$; or at least one of $R_1$, $R_{1a}$, $R_4$, or $R_{4a}$ is an enzyme substrate or a protecting group;
$R_2$, $R_3$, $R_5$, $R_6$, $R_7$, $R_8$ and $R_9$ are each independently H, halogen, CN, alkyl, alkenyl, alkoxy, alkylthio, alkylamino, dialkylamino, alkylaminocarbonyl, dialkylaminocarbonyl, aryl, heteroaryl, -L-$PO_3^{2-}$, -L-$SO_3^-$, -L-$R_x$, a reactive sulfonamide, or a neutral or positively charged unreactive sulfonamide; or one or more pair of $R_2$ and $R_{1a}$, $R_3$ and $R_{4a}$, $R_4$ and $R_5$, $R_5$ and $R_6$, $R_8$ and $R_9$, or $R_9$ and $R_1$, together with the atoms to which they are attached form one or more fused saturated or unsaturated rings that are optionally substituted by at least one halogen, CN, alkyl, heteroalkyl, alkenyl, alkoxy, alkylthio, alkylamino, dialkylamino, alkylaminocarbonyl, dialkylaminocarbonyl, aryl, heteroaryl, -L-PO$_3^{2-}$, L-SO$_3^-$, -L-R$_x$, a reactive sulfonamide, or a neutral or positively charged unreactive sulfonamide;

$R_7'$ is H, OH, CN, or $C_1$-$C_6$ alkoxy; or $R_7'$ in combination with $R_7$ forms a 5- or 6-membered spirolactone or spirosultone ring;

$R_x$ is a reactive group;

L is a bond or $(Q)_n$;

each Q is independently NR$_d$, S(O)$_t$, O, C(=X'), (C=X'), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two 0 are adjacent;

each X' is independently NR$_d$, S or O;

n is 1-20;

each R$_d$ is H, substituted or unsubstituted alkyl;

provided that the compound comprises at least one neutral or positively charged unreactive sulfonamide.

In one embodiment, the unreactive sulfonamide has a molecular weight of less than about 350. In another embodiment, the unreactive sulfonamide moiety has a structure of Formula IIb:

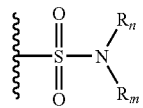

Formula IIb wherein R$_m$ and R$_n$ are each independently H, alkyl, or heteroalkyl; wherein the unreactive sulfonamide moiety carries a zero or positive charge.

In some embodiments, R$_m$ and R$_n$ are each independently H or a $C_1$-$C_{12}$ alkyl. In other embodiments, the compound of the invention has a structure of Formula IIIb:

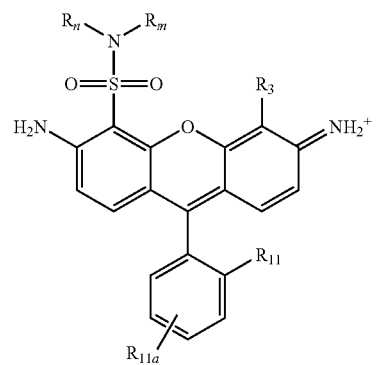

Formula IIIb wherein:
R$_3$ is —SO$_3^-$;
R$_m$ and R$_n$ are each independently H, alkyl, or heteroalkyl;
R$_{11}$ is —CO$_2$ or —SO$_3^-$; and
R$_{11a}$ is H, —CO$_2$—, —SO$_3^-$, or -L-R$_x$.

Also provided herein is a method of preparing a labeled biomolecule comprising reacting a biomolecule with a compound having a structure of Formula VIIIa or VIIIb:

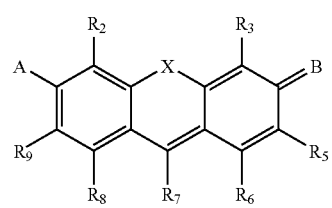

Formula VIIIa

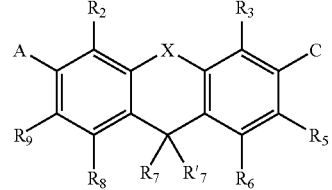

Formula VIIIb wherein:
X is O, S, or —C(CH$_3$)$_2$—;
A is —OR$_1$ or —NR$_1$R$_{1a}$;
B is =O or =N$^+$R$_4$R$_{4a}$;
C is —OR$_4$ or —NR$_4$R$_{4a}$;
R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;

R$_2$, R$_3$, R$_5$, R$_6$, R$_7$, R$_8$, and R$_9$ are each independently H, halogen, CN, alkyl, alkenyl, alkoxy, alkylthio, alkylamino, dialkylamino, alkylaminocarbonyl, dialkylaminocarbonyl, aryl, heteroaryl, -L-PO$_3^{2-}$, L-SO$_3^-$, -L-R$_x$, a reactive sulfonamide or an unreactive sulfonamide; or one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, heteroalkyl, alkenyl, alkoxy, alkylthio, alkylamino, dialkylamino, alkylaminocarbonyl, dialkylaminocarbonyl, aryl, heteroaryl, -L-PO$_3^{2-}$, L-SO$_3^-$, -L-R$_x$, a reactive sulfonamide or an unreactive sulfonamide;

R$_7'$ is H, OH, CN, or $C_1$-$C_6$ alkoxy; or R$_7'$ in combination with R$_7$ forms a 5- or 6-membered spirolactone or spirosultone ring;

R$_x$ is a reactive group;

L is a bond or $(Q)_n$;

each Q is independently NR$_d$, S(O)$_t$, O, C(=X'), (C=X'), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two 0 are adjacent;

each X' is independently NR$_d$, S or O;

n is 1-20;

each R$_d$ is H, substituted or unsubstituted alkyl;

provided that the compound comprises at least one reactive group.

In some embodiments of the compounds of the invention, X is O. In other embodiments, X is S. In still other embodiments, X is —C(CH$_3$)$_2$—.

In some embodiments of the compounds of the invention, A is —OR$_1$. In other embodiments, A is —NR$_1$R$_{1a}$.

R$_1$ and R$_{1a}$ include, for example, H and -L-alkyl, unsubstituted or substituted with -L-SO$_3^-$, -L-PO$_3^{2-}$, a water-soluble polymer, or with -L-R$_x$. In one embodiment, A is —OH. In another embodiment, A is —OR$_1$ and R$_1$ is (C=O)C$_1$-C$_{10}$ alkyl.

In another embodiment, R$_1$ and R$_{1a}$ together with the nitrogen to which they are attached form a saturated or unsaturated ring optionally substituted by any of -L-SO$_3^-$, -L-PO$_3^{2-}$ and -L-R$_x$.

In one embodiment, at least one of R$_1$ and R$_{1a}$ is an enzyme substrate or a protecting group. For example, R$_1$ or R$_{1a}$ is a peptide which is an enzyme substrate. Alternatively, R$_1$ or R$_{1a}$ is a carbohydrate which is an enzyme substrate. In another embodiment, R$_1$ or R$_{1a}$ is a compound comprising an ester linkage which is an enzyme substrate.

In some embodiments of the compounds of the invention, B is =O. In other embodiments, B is =N$^+$R$_4$R$_{4a}$.

R$_4$ and R$_{4a}$ include, for example, H and -L-alkyl, unsubstituted or substituted with -L-SO$_3^-$, -L-PO$_3^{2-}$, a water-soluble polymer, or with -L-R$_x$. In one embodiment, B is =NH$_2^+$. In another embodiment, R$_4$ and R$_{4a}$ together with the nitrogen to which they are attached form a saturated or unsaturated ring optionally substituted by any of -L-SO$_3^-$, -L-PO$_3^{2-}$ and -L-R$_x$. For example, R$_4$ and R$_{4a}$ together with the nitrogen to which they are attached form a saturated 6-membered ring.

In some embodiments, R$_2$, R$_3$, R$_5$, R$_6$, R$_8$, and R$_9$ are each independently H, halogen, CN, alkyl, alkenyl, alkoxy, aryl, heteroaryl, -L-PO$_3^{2-}$, -L-SO$_3^-$, or -L-R$_x$; or one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$.

In some embodiments, R$_1$ and R$_9$ taken together with the atoms to which they are attached form one or more fused rings. For example, R$_1$ and R$_9$ taken together form one of the rings shown below:

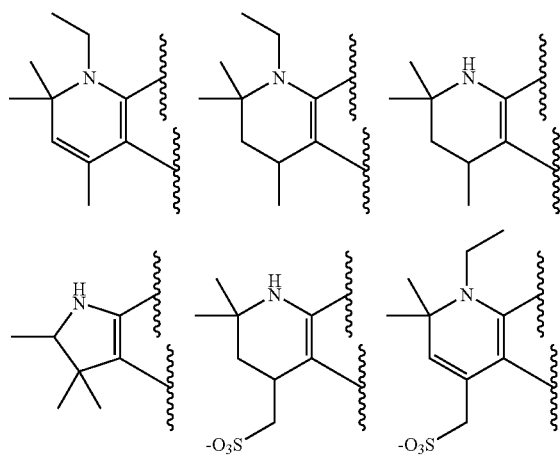

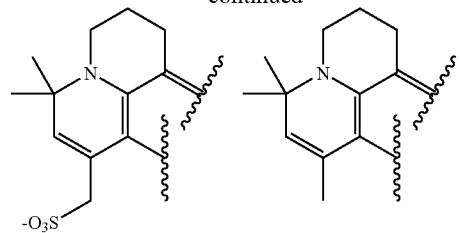

In some embodiments, R$_4$ and R$_5$ taken together with the atoms to which they are attached form one or more fused rings. For example, R$_4$ and R$_5$ taken together form one of the rings shown below:

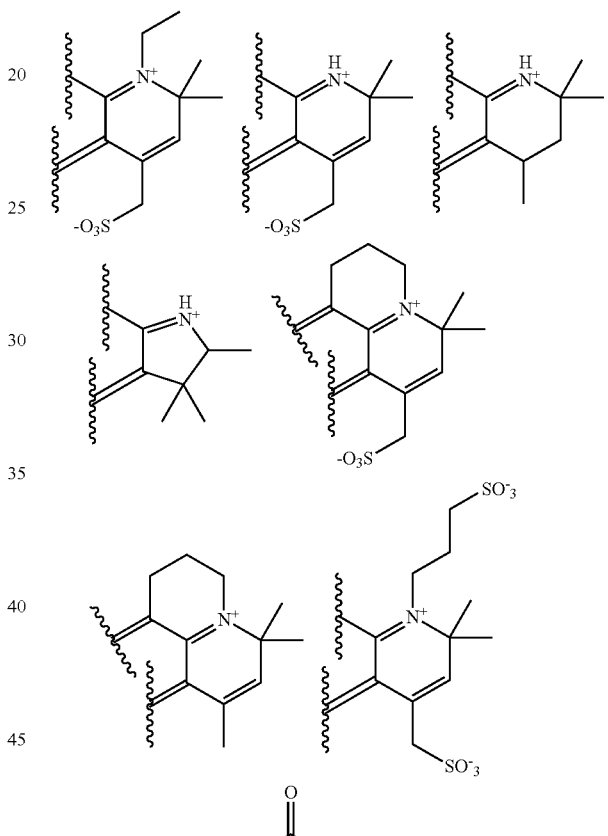

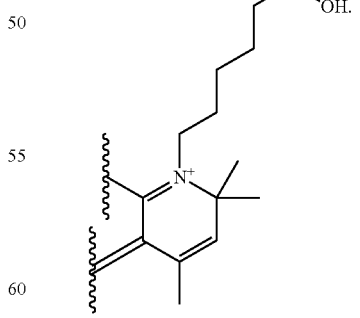

When the compound of the invention is of formula Ib, R'$_7$ is H or a substituent of the group R$_7$, wherein R'$_7$ together with R$_7$ and the carbon atom they are attached to in the xanthenes ring form a 5- or 6-membered spirolactone or spirosultone ring.

In some embodiments of Formula VI, a maximal fluorescence excitation wavelength of the compound is about 633 nm.

In a further aspect, the invention provides a kit comprising: i) a compound of the invention ii) a buffer; iii) materials or devices for purifying conjugation products; and iv) instructions instructing the use of the compound.

In another aspect, the invention provides a biomolecule comprising a label having a structure of the invention has undergone a reaction which attaches the label to the biomolecule. In some embodiments, the biomolecule comprises a polynucleotide. In some embodiments, the biomolecule comprises a polypeptide. In some embodiments, the polypeptide further comprises an antigen binding site. In some embodiments, the polypeptide is a whole immunoglobulin. In some embodiments, the polypeptide is a Fab fragment.

In another aspect, the invention provides an immunoglobin comprising a label having a structure of the invention, wherein at least one reactive moiety of the compound has undergone a reaction which attaches the label to the immunoglobin, wherein the immunoglobin is an antibody that binds specifically to an antigen on a cancer cell. In some embodiments, the antibody binds to erb2.

In some embodiments, the substrate biomolecule to be labeled is a polypeptide, a polynucleotide, a carbohydrate, a lipid or a combination thereof. In other embodiments, the substrate biomolecule is a polynucleotide.

In yet another aspect, the invention provides a method for labeling a cell within a population of cells whereby the cell is differentially labeled relative to neighboring cells within the population, the method comprising contacting the cell with a biomolecule labeled according to the methods of the invention, wherein the biomolecule comprises a targeting moiety that binds to a binding partner that is indicative of the cell, and thereby differentially labeling the cell relative to neighboring cells within the population. In some embodiments, the method further comprises the step of imaging the cell, the imaging step comprising: i) directing exciting wavelength to the cell; and ii) detecting emitted fluorescence from the cell. In some embodiments, the labeling takes place in vitro. In other embodiments, the labeling takes place in vivo.

In some embodiments, L is a bond or has the formula $(Q)_n$, where each Q is independently $NR_d$, $S(O)_t$, O, C(=X'), (C=X'), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two $NR_d$ are adjacent and no two O are adjacent. In such embodiments, n is 1-20, and each $R_d$ is H or substituted or unsubstituted alkyl.

In some cases, the L of an -L-$R_x$ group is a polymethylene —$(CH_2)$—, where n is from 1 to about 6. In other cases, the L of an -L-$R_x$ group may comprise a water-soluble moiety, such as a polyethylene glycol (or PEG) unit, where the number of ethylene glycol unit may be from 1 to about 30, for example. More typically, the number of ethylene glycol unit is from 1 to about 24. In some cases, the L of -L-$R_x$ comprises a PEG moiety of 8 ethylene glycol units. In other cases, the PEG moiety comprises 12 ethylene units. The PEG moiety may be useful for increasing the water solubility of the dye and in some cases increases the fluorescence brightness of the dye when conjugated to a polymer, such as a protein or polynucleic acid.

Some but not all of compounds of the invention may comprise at least one reactive group $R_x$. A reactive group is a chemical moiety capable of reacting with a reaction partner on a substrate or substrate molecule to form a covalent bond.

A compound of the invention can be used to label a wide variety of molecules or substrates that contain a suitable reaction partner or are derivatized to contain a suitable reaction partner. "Reactive group" and "reaction partner" may refer to groups on a compound of the present invention, or to groups on a molecule to be labeled. Here, by way of convenience, but not limitation, a bond-forming group on a compound will generally be referred to as a reactive group and a bond-forming group on the substrate molecule will generally be referred to as a reaction partner.

In any of the structural formulas shown herein, "$R_x$" may be any reactive group that confers a desirable functional property to the compound of the invention. The reactive group and its reaction partner may be an electrophile and a nucleophile, respectively, that can form a covalent bond with or without a coupling agent or catalyst. According to one embodiment, the reactive group is a photoactivatable group capable of reacting with a hydrocarbon molecule upon ultraviolet photoactivation or photolysis. According to another embodiment, the reactive group is a dienophile capable of reacting with a conjugated diene via a Diels-Alder reaction. According to yet another embodiment, the reactive group is a 1,3-diene capable of reacting with a dienophile. According to still another embodiment, the reactive group is an alkyne capable of reacting with an azido functional group to form a 1,2,3-triazole linkage. According to still another embodiment, the reactive group is a 2-(diphenylphosphino)benzoic acid methyl ester capable of reacting with an azido functional group to form an amide linkage via so-called Staudinger reaction. Merely by way of example, examples of useful reactive groups, functional groups, and corresponding linkages according to the present invention are listed below in Table 1.

TABLE 1

Examples of Reactive Groups, Functional Groups, and Covalent Linkages

| Reactive Group | Reaction Partner/ Substrate | Resulting Covalent Linkage |
|---|---|---|
| activated esters * | amines/anilines | Carboxamides |
| acrylamides | Thiols | Thioethers |
| acyl azides ** | amines/anilines | Carboxamides |
| acyl halides | amines/anilines | Carboxamides |
| acyl halides | Alcohols/phenols | Esters |
| acyl nitriles | Alcohols/phenols | Esters |
| acyl nitriles | amines/anilines | Carboxamides |
| aldehydes | amines/anilines | Imines |
| aldehydes or ketones | Hydrazines | Hydrazones |
| aldehydes or ketones | Hydroxylamines | Oximes |
| alkyl halides | amines/anilines | alkyl amines |
| alkyl halides | Thiols | Thioethers |
| alkyl halides | alcohols/phenols | Esters |
| alkyl sulfonates | Thiols | Thioethers |
| alkyl sulfonates | carboxylic acids | Esters |
| alkyl sulfonates | alcohols/phenols | Esters |
| anhydrides | alcohols/phenols | Esters |
| anhydrides | amines/anilines | Carboxamides |
| aryl halides | Thiols | Thiophenols |
| aryl halides | Amines | aryl amines |
| aziridines | Thiols | Thioethers |
| boronates | Glycols | boronate esters |
| epoxides | Thiols | Thioethers |
| haloacetamides | Thiols | Thioethers |
| halotriazines | amines/anilines | Aminotrizaines |
| halotriazines | alcohols/phenols | triazinyl ethers |
| imido esters | amines/anilines | Amidines |
| isocyanates | amines/anilines | Ureas |
| isocyanates | alcohols/phenols | Urethanes |
| isothiocyanates | amines/anilines | Thioureas |
| maleimides | Thiols | Thioethers |

TABLE 1-continued

Examples of Reactive Groups, Functional Groups, and Covalent Linkages

| Reactive Group | Reaction Partner/ Substrate | Resulting Covalent Linkage |
|---|---|---|
| phosphoramidites | Alcohols | phosphite esters |
| silyl halides | Alcohols | silyl ethers |
| sulfonate esters | amines/anilines | alkyl amines |
| sulfonate esters | Thiols | Thioethers |
| sulfonate esters | Alcohols | Ethers |
| sulfonyl halides | amines/anilines | Sulfonamides |
| sulfonyl halides | phenols/alcohols | sulfonate esters |
| azide | alkyne | 1,2,3-triazole |
| Cis-platinum | guanosine | Platinum-guanosine complex |

\* Activated esters, as understood in the art, generally have the formula —COΩ, where Ω is a good leaving group, such as succinimidyloxy (—OC$_4$H$_4$O$_2$), sulfosuccinimidyloxy (—OC$_4$H$_3$O$_2$—SO$_3$H), or -1-oxybenzotriazolyl (—OC$_6$H$_4$N$_3$), for example; or an aryloxy group or aryloxy substituted one or more times by electron-withdrawing substituent(s), such as nitro, fluoro, chloro, cyano, trifluoromethyl, or combinations thereof, for example, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are independently C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl.
\*\* Acyl azides can also rearrange to isocyanates.

The reactive group may be one that will react with an amine, a thiol, a hydroxyl or an aldehyde. The reactive group may be an amine-reactive group, such as a succinimidyl ester (SE), for example, or a thiol-reactive group, such as a maleimide, a haloacetamide, or a methanethiosulfonate (MTS), for example, or an aldehyde-reactive group, such as an amine, an aminooxy, or a hydrazide, for example.

In some embodiments of the invention, a substituted xanthene dye is provided which comprises one or more reactive sulfonamide groups, wherein the xanthene dye has an absorption maximal wavelength of equal to or greater than about 488 nm. In some embodiments, the xanthene dye has an absorption maximal wavelength of equal to or greater than about 532 nm. In some embodiments of the invention, a substituted rhodamine dye is provided which comprises one or more reactive sulfonamide groups, wherein the rhodamine dye has an absorption maximal wavelength of equal to or greater than about 514 nm.

The invention also provides a compound of Formula VII:

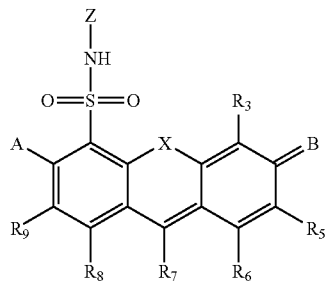

wherein:
Z is a metal chelator;
X is O, S, or —C(CH$_3$)$_2$—;
A is —OR$_1$ or —NR$_1$R$_{1a}$;
B is =O or =N$^+$R$_4$R$_{4a}$;
C is —OR$_4$ or —NR$_4$R$_{4a}$;
R$_1$, R$_{1a}$, R$_4$, and R$_{4a}$ are each independently H or alkyl, unsubstituted or substituted with -L-SO$_3^-$, -L-PO$_3^-$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;
R$_3$, R$_5$, R$_6$, R$_7$, R$_8$, and R$_9$ are each independently H, halogen, CN, alkyl, alkenyl, alkoxy, alkylthio, alkylamino, dialkylamino, alkylaminocarbonyl, dialkylaminocarbonyl, aryl, heteroaryl, -L-PO$_3^{2-}$, L-SO$_3^-$, -L-R$_x$, a reactive sulfonamide or a neutral or positively charged unreactive sulfonamide; or one or more pair of R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, heteroalkyl, alkenyl, alkoxy, alkylthio, alkylamino, dialkylamino, alkylaminocarbonyl, dialkylaminocarbonyl, aryl, heteroaryl, -L-PO$_3^{2-}$, L-SO$_3^-$, -L-R$_x$, a reactive sulfonamide or a neutral or positively charged unreactive sulfonamide;
R$_x$ is a reactive group;
L is a bond or (Q)$_n$;
each Q is independently NR$_d$, S(O)$_t$, O, C(=X'), (C=X'), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two 0 are adjacent;
each X' is independently NR$_d$, S or O;
n is 1-20; and
each R$_d$ is H, substituted or unsubstituted alkyl.

In some embodiments, Z is a chelator for a target ion selected from Ca$^{2+}$, Mg$^{2+}$, Zn$^{2+}$, Cu$^{2+}$, Ni$^{2+}$, Fe$^{3+}$, Na$^+$, K$^+$, Hg$^{2+}$, Pb$^{2+}$, Cd$^{2+}$ and As$^{3+}$. For example, Z is a BAPTA-based Ca$^{2+}$ chelator.

In other embodiments of the invention, the target ions to be detected are selected from Li+, Na+, K+, Cs+, Ca2+, Zn2+, Mg2+, Rb+, Tb3+ or Eu3+. In another embodiment of the invention, the target ions are selected from Li+, Na+, K+, Ca2+, Zn2+, and Mg2+. Additional target ions for selected embodiments of the present indicators also include Mn2+, Fe2+, Fe3+, Co2+, Ni2+, Cu2+, Cu+, Zn2+, Al3+, Cd2+, Ag+, Au+, Tl+, Pd2+, Hg+, Sn2+, Pb2+, Sr2+, Ba2+, Mo3+, Ga3+, In3+, La3+, Eu3+, Tb3+, Dy3+, Ru3+, Sc3+, As3+, Sb3+, Cr3+, Bi3+, Ce3+, Ce4+, Pd2+, Pt2+ and Pt4+ions. In yet another embodiment of the invention, the target ions of the instant indicators are Fe2+, Fe3+, Co2+, Ni2+, Cu2+, Cu+, Zn2+, Al3+, Cd2+, Hg2+, Pd2+, Ba2+, La3+, Tb3+ and Cr3+ ions. In yet another embodiment, the target ions are selected from the group consisting of Fe3+, Ni2+, Cu2+, Cu+, Hg2+, or Pb2+. For example, the target ion to be detected is calcium. Calcium acts as an intracellular messenger and regulator, and the detection and measurement of intracellular free calcium concentrations (Ca$^{2+}$) can be very useful. The compounds of the invention are, for example, used to measure calcium concentrations in aqueous solutions, such as biological fluids. For example, the compounds of the invention can be used to measure calcium concentrations within living cells. In some embodiments, the compound of the invention shows significant selectivity over other metal ions, such as Mg$^{2+}$.

Any chelator that binds an ion of interest and results in a change in fluorescence properties is suitable. For example, Z can be a crown ether, such as a diaryldiaza crown ethers (U.S. Pat. No. 5,405,975); a derivative of 1,2-bis-(2-aminophenoxyethane)-N,N,N',N'-tetraacetic acid (BAPTA) (U.S. Pat. No. 5,453,517; U.S. Pat. No. 5,049,673); a derivative of 2-carboxymethoxy-aniline-N,N-diacetic acid (APTRA) (Ragu et al. AM. J. PHYSIOL. 256, C540 (1989); or a pyridyl-based or phenanthroline target ion chelator; (U.S.

Pat. No. 5,648,270) (incorporated by reference). Other chelating compounds are described in U.S. Pat. No. 4,849,362; U.S. Pat. No. 5,501,980; U.S. Pat. No. 5,459,276; and U.S. Pat. No. 5,501,980. Some fluorescent indicators selective for Li+, Na+ and K+ in aqueous or organic solvents are also known, based on the chemical modification of crown ethers (U.S. Pat. Nos. 5,134,232; and 5,405,975; Gromov et al. Russian Chemical Bulletin (1999) 48:6 p. 1190-1192; Lockhart et al, J. C. S. Perkin I (1977) p 202-204).

Exemplary Structures of Compounds of the Invention are Shown Below in Table 3.

| Dye No. | Structure | Formula | $\lambda_{abs}/\lambda_{em}$ (nm) (in pH 7.4 PBS) |
|---|---|---|---|
| 1 | 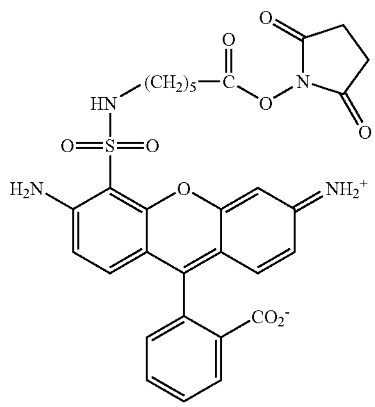 | Formula IIIa | 488/516 |
| 2 | 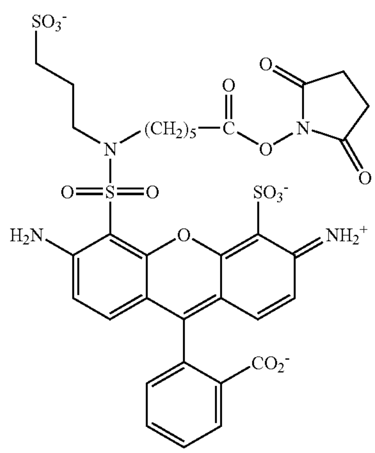 | Formula IIIa | 488/516 |
| 3 | 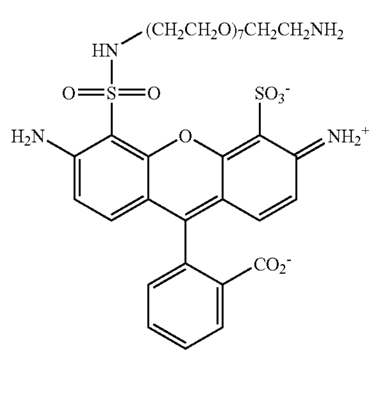 | Formula IIIa | 488/516 |

-continued

| Dye No. | Structure | Formula | $\lambda_{abs}/\lambda_{em}$ (nm) (in pH 7.4 PBS) |
|---|---|---|---|
| 4 | 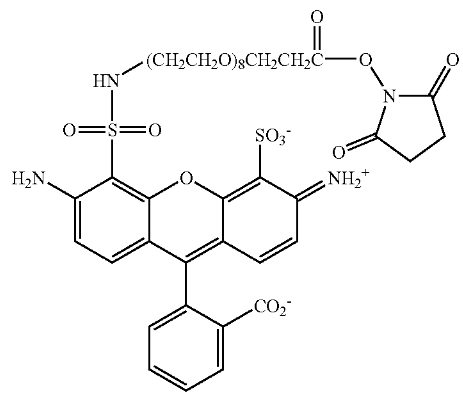 | Formula IIIa | 488/516 |
| 5 | 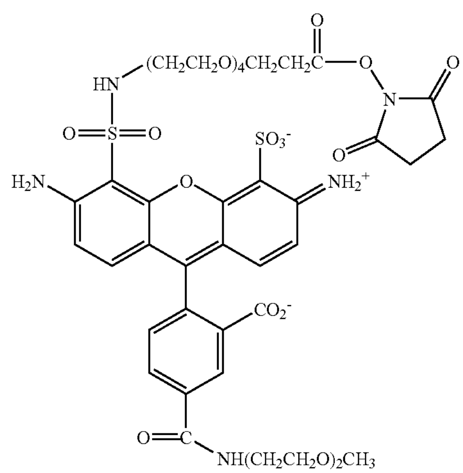 | Formula IIIa | 488/516 |
| 6 | 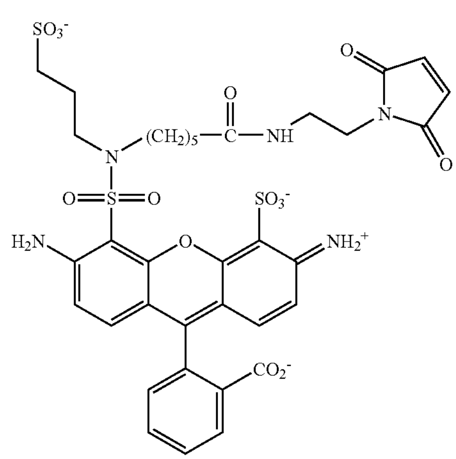 | Formula IIIa | 488/516 |

-continued

| Dye No. | Structure | Formula | $\lambda_{abs}/\lambda_{em}$ (nm) (in pH 7.4 PBS) |
|---|---|---|---|
| 7 | 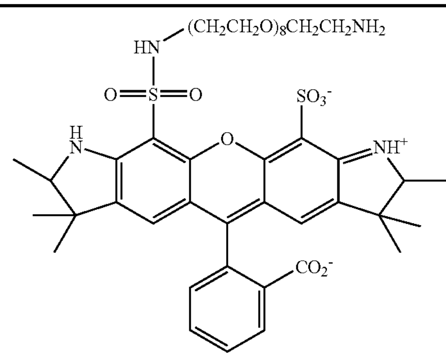 | Formula IV | |
| 8 | 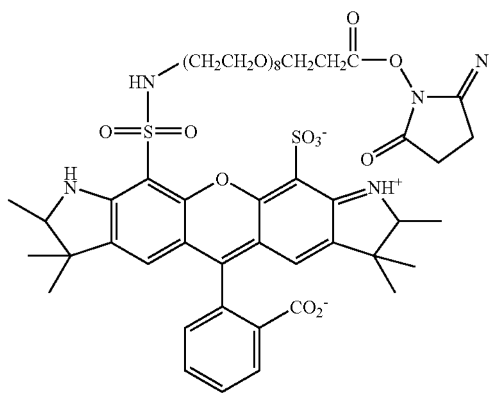 | Formula IV | |
| 9 | 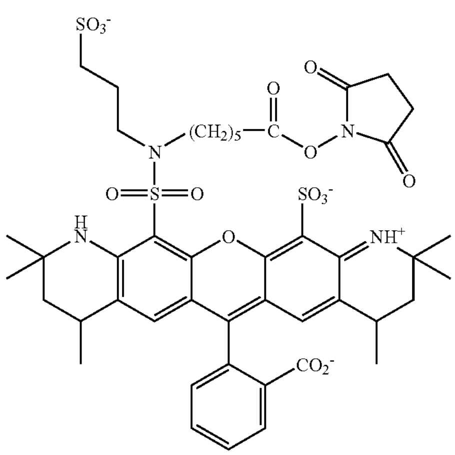 | Formula IV | 529/ |
| 10 | 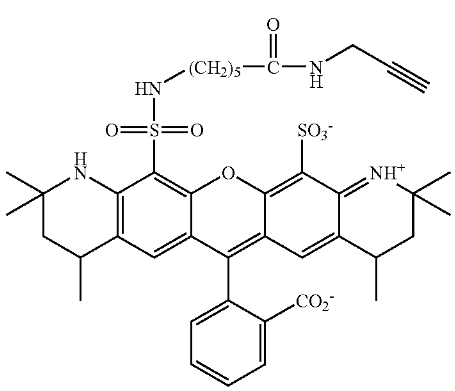 | Formula V | |

-continued
| Dye No. | Structure | Formula | $\lambda_{abs}/\lambda_{em}$ (nm) (in pH 7.4 PBS) |
|---|---|---|---|
| 11 | 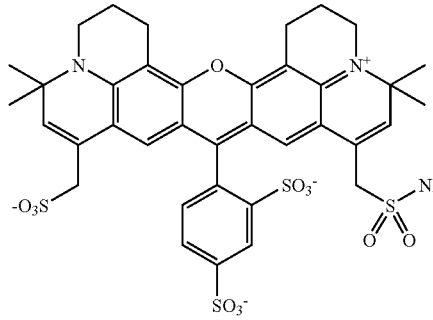 | Formula VI | |
| 12 | 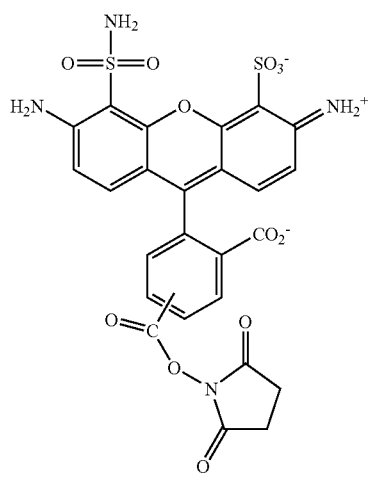 | Formula IIIb | 490/520 |
| 13 | 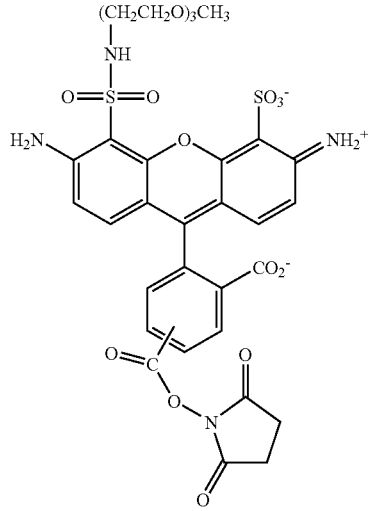 | Formula IIIb | 490/520 |

| Dye No. | Structure | Formula | $\lambda_{abs}/\lambda_{em}$ (nm) (in pH 7.4 PBS) |
|---|---|---|---|
| 14 | 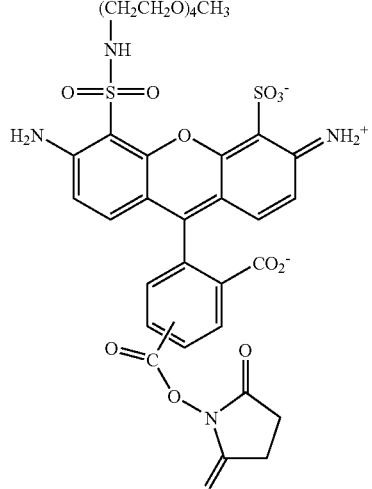 | Formula IIIb | 490/520 |

Uses of the Subject Compounds

The subject compounds find use in a variety of different applications. One application of interest is the use of the subject compounds as labeling agents which are capable of imparting a fluorescent property to a particular composition of matter.

Provided herein is a method of preparing a labeled biomolecule comprising reacting a biomolecule with a compound having a structure of Formula VIIIa or VIIIb:

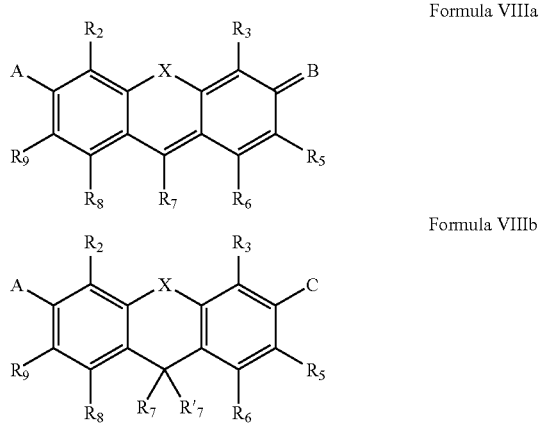

Formula VIIIa

Formula VIIIb wherein:

A is OH or $NR_1R_{1a}$; wherein $R_1$ and $R_{1a}$ are each independently H, $C_1$-$C_{12}$alkyl, or $R_1$ and $R_{1a}$ together with the nitrogen to which they are attached form a substituted or unsubstituted saturated or unsaturated ring;

B is =O or =$N^+R_4R_4$ or $NR_1R_{1a}$; wherein $R_4$ and $R_{4a}$ are each independently H, $C_1$-$C_{12}$alkyl, or $R_4$ and $R_{4a}$ together with the nitrogen to which they are attached form a substituted or unsubstituted saturated or unsaturated ring; and $R_2$, $R_3$, $R_5$, $R_6$, $R_7$, $R_8$ and $R_9$ are each independently H, halogen, CN, substituted or unsubstituted alkyl, substituted or unsubstituted heteroalkyl, substituted or unsubstituted alkoxy, substituted or unsubstituted aryl, substituted or unsubstituted heteroaryl, a reactive group selected from a sulfonyl chloride and a reactive sulfonamide, a methyl group substituted with a reactive group selected from a sulfonyl chloride and a reactive sulfonamide, an unreactive sulfonamide, —$PO_3^{2-}$, or —$SO_3^-$; or one or more of $R_2$ and $R_{1a}$, $R_3$ and $R_{4a}$, $R_4$ and $R_5$, $R_5$ and $R_6$, or $R_9$ and $R_1$ together with the atoms to which they are attached form a 5 or 6-membered ring that is optionally substituted with a reactive sulfonamide or a methyl group substituted with a reactive group selected from a sulfonyl chloride and a reactive sulfonamide; provided that a compound of Formula VIIIa or VIIIb comprises at least one reactive group.

In some embodiments of Formula VIIIa or VIIIb, the 5 or 6-membered ring formed by $R_2$ and $R_{1a}$, $R_3$ and $R_{4a}$, $R_4$ and $R_5$, $R_5$ and $R_6$, or $R_9$ and $R_1$ together with the atoms to which they are attached is a substituted or unsubstituted or saturated or unsaturated ring.

In some embodiments, the reactive sulfonamide has the following formula:

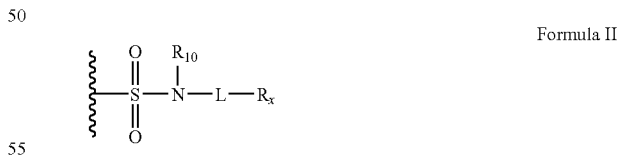

Formula II wherein $R_{10}$, L and $R_x$ are as defined herein.

The method of labeling a substrate biomolecule, comprises the steps of:

1) providing: a reactive dye of the invention; 2) incubating said dye and said substrate biomolecule in a suitable solvent or buffer in the presence or absence of a coupling agent or a catalyst for a time sufficient to form a covalent linkage between dye and the substrate biomolecule.

In some instances a substrate biomolecule further comprises a partner reactive group, where the substrate biomolecule is selected from the list consisting of proteins, peptides, amino acids, DNA, RNA, oligonucleotides, nucleotides, nucleosides, carbohydrates, polymers, lipids, drugs, biological ligands, fluorescent dyes and metal chelators;

The need for a coupling agent or a catalyst for the labeling reaction depends on the nature of the reactants and is generally well known to one skilled in the art. For example, for a coupling reaction between a carboxylic acid and an aliphatic amine, a carbodimide, such as DCC or EDAC, is typically used. In some cases, a catalyst may be helpful to facilitate a labeling reaction. For example, DMAP (4-dimethylaminopyridine) may be used to catalyze a reaction between a dye having a succinimidyl ester and a substrate molecule having an aromatic amine.

The compounds of the present invention can be used to react with any of a broad range of molecules, including but not limited to, biomolecules such as polypeptides, polypeptide-based toxins, amino acids, nucleotides, polynucleotides including DNA and RNA, lipids, and carbohydrates, and any combinations thereof. Additionally, the compounds of the invention can be used to react with haptens, drugs, ion-complexing agents such as metal chelators, microparticles, synthetic or natural polymers, cells, viruses, other fluorescent molecules including the dye molecule according to the invention, or surfaces. The substrate molecules typically comprise one or more functional groups, which react with the reactive group of the subject compounds to form covalent or non-covalent linkage. In one aspect, the reactive group of a compound of the invention is an activated ester (such as a succinimidyl ester, or SE), a maleimide, a hydrazide or an aminooxy group. Accordingly, in some aspects, functional group from a substrate molecule (or reaction substrate) is an amine, a thiol, an aldehyde or ketone. The resulting fluorescently labeled substrate molecules may be referred to as conjugates or labeled substrate molecules. Any methods practiced in the art (e.g., Brinkley, Bioconjugate Chem. 3, 2 (1992), incorporated herein by reference) for preparing fluorescent group-substrate conjugates are applicable for practicing the subject invention.

Conjugates of biomolecules and compounds of the invention usually have high fluorescence quantum yield while typically retaining the critical parameters of unlabeled biomolecules, such as solubility, selective binding to a receptor or nucleic acid, activation or inhibition of a particular enzyme or the ability to incorporate into a biological membrane. Nevertheless, conjugates with the highest degree of labeling may still precipitate or bind nonspecifically. As necessary, a less-than-maximal degree of labeling may be acceptable in order to preserve function or binding specificity. Preparing the conjugates of the invention may involve experimentation to optimize properties. Following conjugation, unconjugated labeling reagent may be removed by techniques known in the art such as by gel filtration, dialysis, conjugate precipitation and resolubilization, HPLC or a combination of these techniques. The presence of free dye, particularly if it remains chemically reactive, may complicate subsequent experiments with the bioconjugate.

Nucleic Acids

In another embodiment, the subject compounds can be used to conjugate with a nucleoside, a nucleotide, or a polynucleotide, wherein any of such molecules may be natural or synthetic, modified or unmodified. The compound of the invention used for labeling may comprise a reactive group which is a phosphoramidite, an activated ester (such as a succinimidyl ester), an alkylating group or a reactive platinum complex. Such molecules may contain or are derivatized to contain one or more reaction partners for the reactive groups on the compounds of the invention. A reactive group of a compound of the invention may react with a suitable reaction partner on said molecule to form a covalent linkage. For example, a phosphoramidite group may react with a hydroxyl group to form a phosphate linkage after deprotection; a succinimidyl ester or the like may react with an amine group to form an amide linkage; and a reactive platinum complex may react with a guanosine base to form a platinum complex linkage. In one embodiment, a reactive compound of the invention comprising an activated ester is reacted with a nucleotide triphosphate comprising a base comprising an aminoalkynyl group, an aminoallyl group or an aminoalkyl group to form a fluorescently labeled nucleotide triphosphate. Such a labeled nucleotide triphosphate is often used to prepare a fluorescently labeled nucleic acid polymer via enzymatic incorporation.

In some embodiments, the fluorescent compound of the invention is reacted with a group or linker attached to the C-5 position of a uridine or cytidine residue. This position is not involved in Watson-Crick base-pairing and interferes little with hybridization to complementary sequences. An aminoalkynyl linker may be introduced between a fluorescent moiety and the nucleotide in order to reduce fluorophore interaction with enzymes or target binding sites. In addition to this four-atom bridge, seven- to 10-atom spacers may be introduced that further separate the fluorophore from the base. The use of longer spacers may result in brighter conjugates and increased hapten accessibility for secondary detection reagents.

Alternatively, deoxycytidine triphosphates may be prepared which are modified at the N-4 position of cytosine using a 2-aminoethoxyethyl (OBEA) linker. Possible steric interference caused by the presence of the fluorescent fluorophore may be reduced by the use of additional spacers.

Fluorescently labeled DNA may be prepared from a fluorescently labeled nucleotide triphosphate by PCR reaction, terminal transferase-catalyzed addition or nick translation. Various polymerases may be used in such reactions. Such polymerases include Taq polymerase (useful e.g. in polymerase chain reaction (PCR) assays), DNA polymerase I (useful e.g. in nick-translation and primer-extension assays), Klenow polymerase (useful e.g. in random-primer labeling), Terminal deoxynucleotidyl transferase (TdT) (useful e.g. for 3'-end labeling), Reverse transcriptase (e.g. for synthesizing DNA from RNA templates) or other polymerases such as SP6 RNA polymerase, T3 RNA polymerase and T7 RNA polymerase for in vitro transcription.

Alternatively, a fluorescently labeled nucleic acid polymer may be prepared by first enzymatically incorporating an amine-labeled nucleotide into a nucleic acid polymer to result in an amine-labeled nucleic acid polymer, followed by the labeling of said amine-labeled polymer with a compound of the invention. More information on the preparation and use of fluorescently labeled nucleotide triphosphates can be found in U.S. Pat. Nos. 4,711,955 and 5,047,519. Still alternatively, a nucleic acid polymer, such as a DNA, may be directly labeled with a compound of the invention comprising a reactive platinum complex as the reactive group, wherein the platinum complex form a coordinative bond with a nitrogen atom of a guanosine base such as described in U.S. Pat. No. 5,714,327.

Aminoacids and Polypeptides

In another embodiment, the subject compounds can be used to conjugate with an amino acid, amino acid analog or a polypeptide. Labeled aminoacids, amino acid analogs and polypeptides may be labeled by reacting the compounds of the invention with amino acids, amino acid analogs and polypeptides comprising reaction partners for the reactive groups on said compounds. Such reaction partners may be natural or unnatural groups present in said polypeptides. By way of example, reaction partners may be the natural residues such as amino groups, which are part of natural lysine residues, or thiol groups, which are part of natural cysteine groups.

Figure 2:
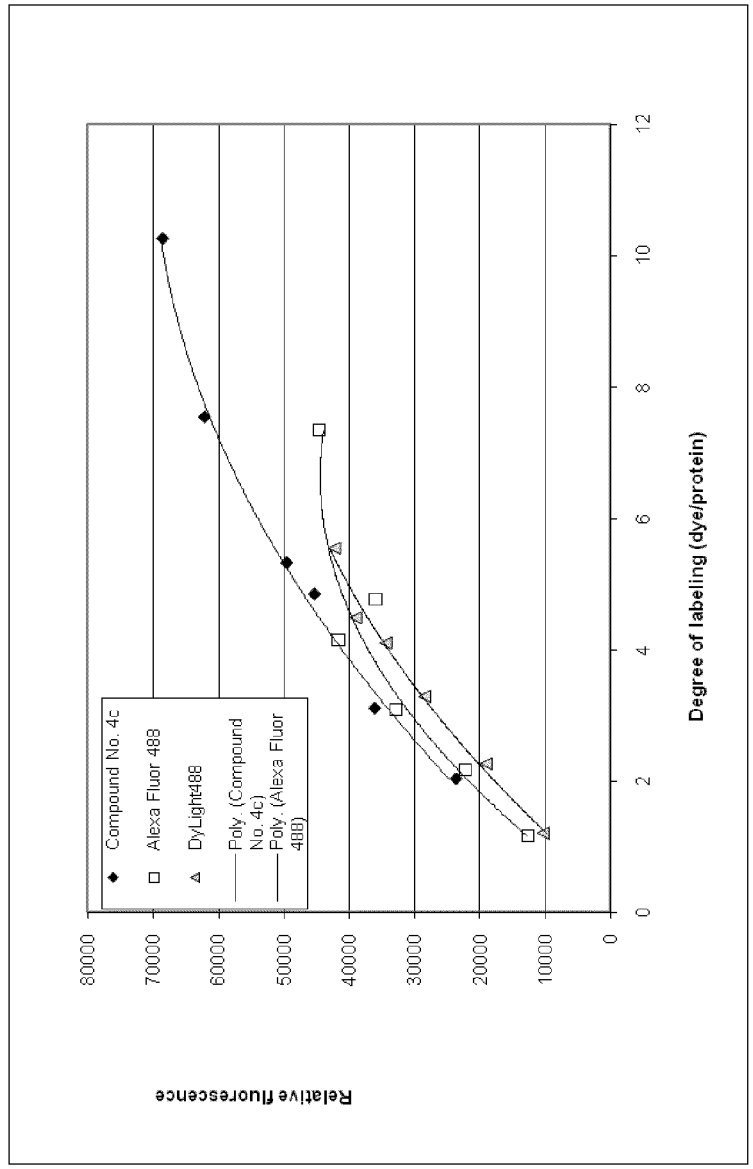
FIG. 2 is a plot of total fluorescence vs. degree of labeling (DOL) for goat anti-rabbit IgG conjugates of Compound No. 4c (Example 6), Alexa Fluor 488 and DyLight 488 at identical protein concentrations in an aqueous buffer, when excited at 488 nm. The data shows that the fluorescent group of the invention has excellent fluorescence quantum yield over a wide range of degree of labeling. See Example 26.
Figure 4:
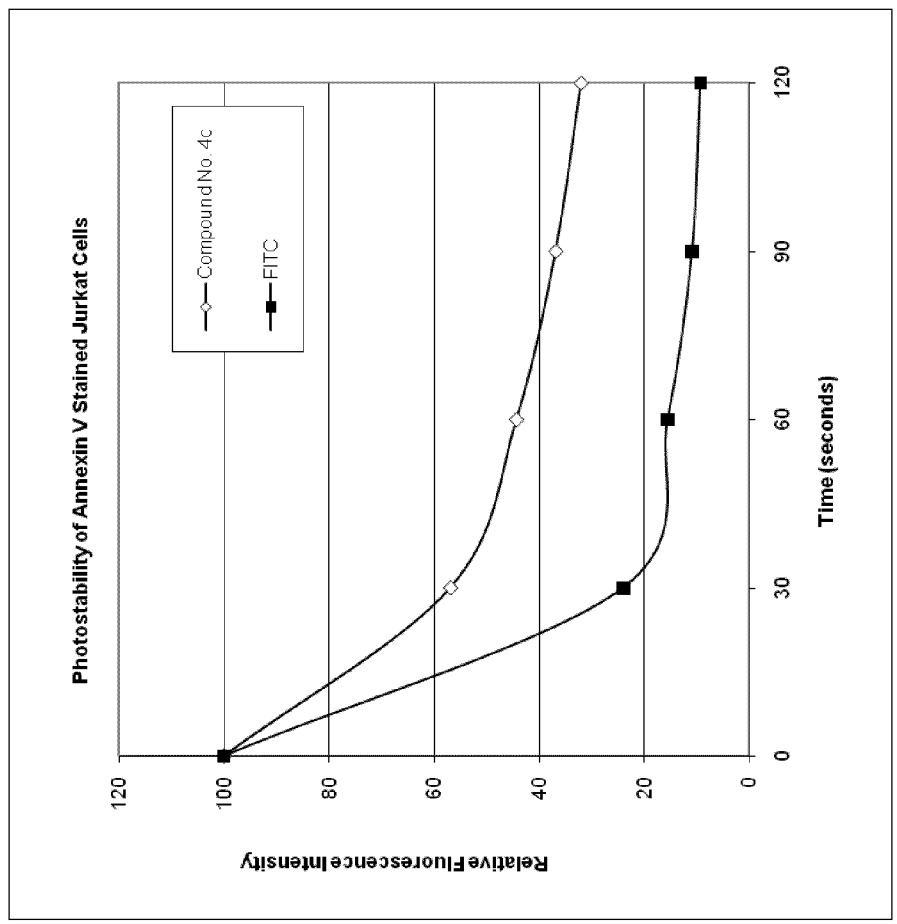
FIG. 4 shows a comparison of the photostability between compound No. 4c (Example 6) and FITC in cellular staining under microscopic illumination. See Example 32.
Figure 5:
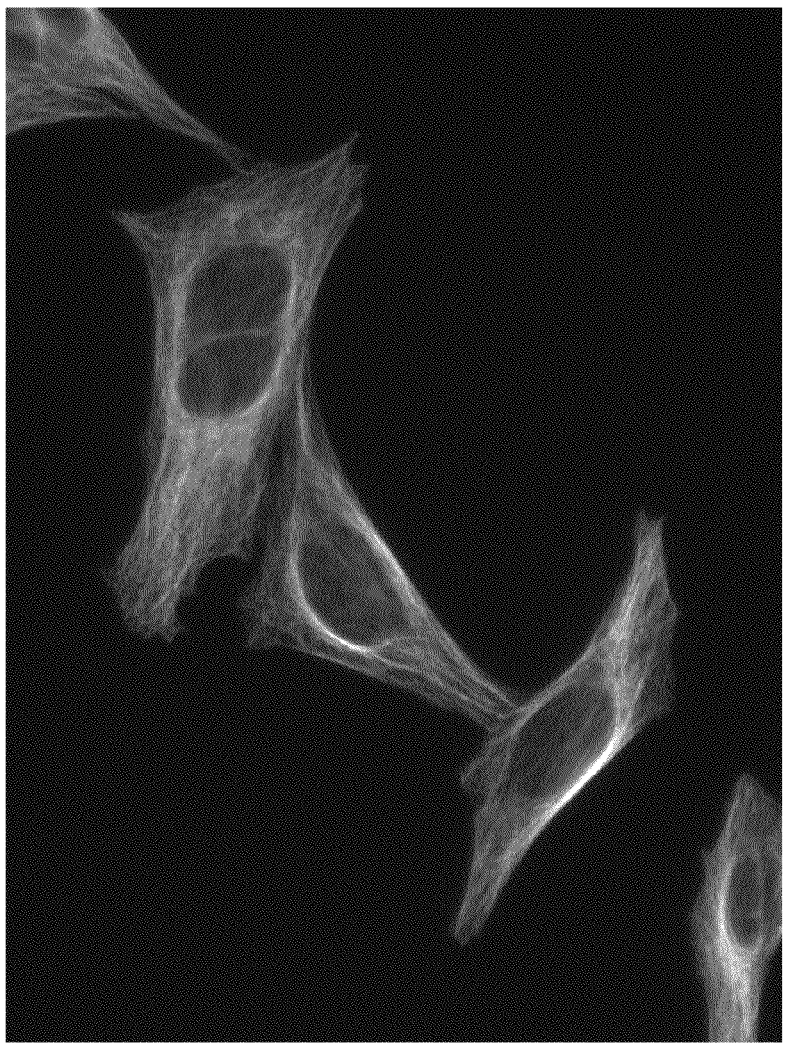
FIG. 5 shows cellular microtubule staining using an alpha-tubulin primary antibody and a secondary antibody labeled with compound No. 4c (DOL-4.8). See Example 33.

In order to achieve the maximal fluorescence possible, a protein may be labeled with as many molecules of the same fluorescent group as possible, to the degree that the biological activity of the protein is minimally affected by the labeling. In other cases it may be desirable to avoid fluorescence quenching resulting from multiple fluorescent group molecules on the protein interacting with each other. Dye-dye interactions may be physical, such as dye aggregation, or may be a spectral, such as FRET-based energy transfer, or a combination of both. Either type of interaction may lead to fluorescence quenching, which can be characterized by a slow rise and then a rapid drop of the total fluorescence of the labeled protein as the degree of labeling increases. FIG. 2 shows that a fluorescent group of the invention that is less likely to quench its fluorescence on an antibody than a similar fluorescent group of prior art. A primary reason for fluorescence quenching of a labeling fluorescent group on protein is believed to be due to formation of dye aggregates such as dye dimer. When dye dimer formation occurs, the absorption spectrum of the fluorescent group-protein conjugate typically shows a doublet peak. As shown in FIG. 1, a fluorescent group of the invention is free of dimer formation on protein as evidenced by lack of double peak appearance in the absorption spectrum. As a result, antibodies labeled with a fluorescent group of the invention over a wide range of DOL all produced excellent signal during intracellular staining (FIG. 2). Another advantage for antibodies labeled with a fluorescent group of the invention is their consistently excellent staining specificity relative to other fluorescently labeled antibodies (FIGS. 4 and 6) over a wide range of DOL, e.g., antibodies labeled with a fluorescent group of the invention retain high binding specificity with their antigen. Still another advantage for an antibody labeled with a dye of the invention is their significantly improved photostability over an antibody labeled with FITC, a commonly used 488 nm-excitable green fluorescent dye (FIG. 5).

(2) Uses of the Labeled Biomolecules of the Invention

The subject compounds provide an effective tool for labeling biomolecules for a wide variety of applications. Labeling allows one to discern interactions involving biomolecules such as proteins, glycoproteins, nucleic acids, and lipids, as well as inorganic chemicals, or any combinations thereof. The interactions may be between nucleic acid molecules, between nucleic acid and protein, and between protein and small molecules. The interactions may be discerned in a cell-free biological system, in a cellular system (including intracellular and extracellular systems), or in vivo, which encompasses which encompasses activities within a cell that is within a tissue or organ or a subject Delineating the various interactions is often a significant step in scientific research and development, drug design, screening and optimization, phylogenetic classification, genotyping individuals, parental and forensic identification, environmental studies, diagnosis, prognosis, and/or treatment of disease conditions.

Biomolecules labeled according to the methods of the invention may be used as binding agents to detect their binding partners, the targets of their biological interaction, as described above. For example, a protein can be labeled with a dye of the invention and used to bind to a cell surface receptor. A binding agent so labeled is contacted with its binding partner, and the fluorescent label is detected. In other embodiments, a binding agent is reacted with a compound of structure of the invention under conditions effective to crosslink the compound with the binding agent Labeled molecules of the invention may be used as part of FRET pairs in a variety of biological assays and methods, whether as donor or acceptor molecules. A person skilled in the art will know to select a suitable FRET partner based on the specific application. Such applications include, but are not limited to, assays involving molecular beacons, FRET protease assays, flow cytometry, nucleic acid hybridization and any other applications where the relative spatial localization of two or more moieties must be probed. FRET is generally useful on scales of 10 to 100 Å. In one embodiment, both the donor and the acceptor of a FRET pair are labeled molecules of the invention. In another embodiment, one member of a FRET pair is a labeled oligonucleotide of the invention which is capable of annealing to a complementary oligonucleotide labeled with a second member of the FRET pair, such that annealing leads to an increase in the efficiency of energy transfer. In this example, the second member of the FRET pair may be a fluorophore of the invention or may be a different fluorophore.

In some applications, it is desirable to quench the labeled molecules of the invention. A variety of quenchers known in the art may be used. Non-limiting examples include Black Hole Quencher™ moieties, DABCYL, Reactive Red 4 (Cibacron Brilliant Red 3B-A), Malachite Green, 4-Dimethylaminophenylazophenyl-4'-isothiocyanate (DABITC), and 4,4'-Diisothiocyanaitodihydro-stilbene-2,2'-disulfonic acid. By way of example, a molecular beacon may be labeled with a compound of the invention as well as with a suitable quencher. In the closed conformation of the beacon, the fluorophore is quenched. When the beacon opens as a result of a recognition or binding event, the fluorescence of the fluorophore increases significantly.

In still another embodiment, the invention provides an energy transfer fluorescent group comprising a first donor fluorescent group and second acceptor fluorescent group wherein: the donor fluorescent group and acceptor fluorescent group are covalently linked to form a FRET pair; at least one of the donor fluorescent group and acceptor fluorescent group is a fluorescent group of the invention; and the energy transfer fluorescent group optionally comprises a reactive group. Methods for preparing energy transfer fluorescent groups and uses thereof have been previously described. See U.S. Pat. No. 6,479,303 and WO 00/13026.

In one embodiment, a fluorescent group of the invention is used to label a fluorescent protein to form a so-called tandem dye, wherein the fluorescent group of the invention and the fluorophore of the fluorescent protein form an energy transfer pair (i.e., FRET pair). In such a FRET pair, the fluorescent group of the invention is either the donor fluorescent group or the acceptor fluorescent group and, likewise, the fluorophore of the protein is either the acceptor fluorescent group or the donor fluorescent group, such that the FRET pair can be excited at or near the absorption maxima of the donor fluorescent group and the fluorescence collected at the emission maxima of the acceptor fluorescent group, resulting in a large Stokes shift. Suitable fluorescent proteins for preparing tandem dyes include, but are not limited to, various phycobiliproteins such as Allophycocyanin B, Allophycocyanin (APC), C-Phycocyanin, R-Phycocyanin, Phycoerythrocyanin, C-Phycoerythrin, b-Phycoerythrin, B-Phycoerythrin, R-Phycoerythrin (R-PE), and the likes. Phycobiliproteins are proteins comprising bilin as prosthetic groups, which are also the fluorophores of the proteins. Preferably, the phycobiliproteins are R-PE or APC. To achieve suitable FRET efficiency, one may choose a fluorescent group of proper wavelengths so that the emission of the donor fluorescent group and the absorption of the acceptor fluorescent group have sufficient spectral overlap. Detailed methods for fluorescent group selection and for preparing tandem dyes are disclosed in U.S. Pat. Nos. 4,520,110 and 5,714,386. Because of their large Stokes shift, tandem dyes of the invention may be useful for multi-color detections where only a limited number of excitation light sources may be available. In particular, tandem dyes of the invention may be useful for fluorescence-activated cell sorting (FACS) or flow cytometry studies. Commercial flow cytometers are typically equipped with 1 to 3 excitation light sources, more commonly 1 to 2 excitation light sources. For example, some of the commercial flow cytometers are equipped with a 488 nm argon laser and a 633 nm He—Ne laser or a 635 nm red diode laser, and a significant number of flow cytometers have only the 488 nm argon laser. Thus, in order to detect multiple targets, each target may be stained with a different fluorescent group having a different emission and the different fluorescent groups all need to be efficiently excited by a common excitation source. Tandem dyes of the invention can fill this need as different tandem dyes having the same excitation maxima but different emission maxima can be readily prepared in one embodiment, a compound of the invention is applied to a biological sample comprising a plurality of polypeptides and optionally other biological molecules under a condition facilitating the covalent labeling of said polypeptides. In some embodiments, the reactive group of the compound is an activated ester, a maleimide, an iodoacetamide, a bromoacetamide, a hydrazide, an amine or an aminooxy group. The biological sample may be a cell lysate or a tissue lysate. The resulting labeled polypeptides or cellular components may be analyzed and/or purified by any of a variety of known tools or techniques, including, but not limited to, protein microarrays, chromatography and gel electrophoresis.

The present invention also provides kits comprising compounds of the invention and/or fluorescent group-substrate conjugates of the invention for various assays as selectively described above. A kit of the invention may comprise one or more compounds of the invention and instructions instructing the use of said compound. For example, a kit may comprise one or more compounds of the invention for labeling a substrate, one or more buffers for the labeling reaction and product purification, a chromatography column for purifying the resulting fluorescent group-substrate conjugate, a protocol for carrying out the procedure, optionally any additional reagents and optionally any reference standard. In another embodiment, a kit comprises one or more fluorescent group-substrate conjugates of the invention, one or more buffers, a protocol for the use of said conjugate(s), optionally any other reagents for an assay, and optionally any calibration standard(s). The kit may further contain other materials or devices of use in purifying the conjugation products.

The signals produced by the fluorescent groups of the invention may be detected in a variety of ways. Generally, a change of signal intensity can be detected by any methods known in the art and is generally dependent on the choice of fluorescent group used. It can be performed with the aid of an optical system. Such system typically comprises at least two elements, namely an excitation source and a photon detector. Numerous examples of these elements are available in the art. An exemplary excitation source is a laser, such as a polarized laser. The choice of laser light will depend on the fluorescent group attached to the probe. For most of the fluorescent groups, the required excitation light is within the range of about 300 nm to about 800 nm, or more commonly from about 350 nm to about 650 nm. Alternatively, compounds of the invention may be excited using an excitation wavelength of about 300 to about 350 nm, 350 to 400 nm, 450 to 500 nm, 500 to 550 nm, 550 to 600 nm, 600 to 650 nm, merely by way of example. Those skilled in the art can readily ascertain the appropriate excitation wavelength to excite a given fluorophore by routine experimentation (see e.g., The Handbook—'A Guide to Fluorescent Probes and Labeling Technologies, Tenth Edition' (2005) (available from Invitrogen, Inc./Molecular Probes) previously incorporated herein by reference). Where desired, one can employ other optical systems. These optical systems may comprise elements such as optical reader, high-efficiency photon detection system, photo multiplier tube, gate sensitive FET's, nano-tube FET's, photodiode (e.g. avalanche photo diodes (APD)), camera, charge couple device (CCD), electron-multiplying charge-coupled device (EMCCD), intensified charge coupled device (ICCD), and confocal microscope. These optical systems may also comprise optical transmission elements such as optic fibers, optical switches, mirrors, lenses (including microlens and nanolens), collimators. Other examples include optical attenuators, polarization filters (e.g., dichroic filter), wavelength filters (low-pass, band-pass, or high-pass), waveplates, and delay lines. In some embodiments, the optical transmission element can be planar waveguides in optical communication with the arrayed optical confinements. See, e.g., U.S. Pat. Nos. 7,292,742, 7,181,122, 7,013,054, 6,917,726, 7,267,673, and 7,170,050. These and other optical components known in the art can be combined and assembled in a variety of ways to effect detection of distinguishable signals.

Fluorescently labeled polynucleotides of the invention find use in a variety of applications. Such applications can involve interactions between nucleic acids, e.g., interactions between DNA and DNA, DNA and RNA, and RNA and RNA, or any other non-naturally occurring nucleic acids PNA, LNA, and/or TNA. Various applications can also involve interactions between nucleic acids and proteins, lipids or combinations thereof. Non-limiting examples of specific nucleic acid assays include nucleic acid amplification, both quantitative or end-point amplification, hybridization in solution or on a substrate (e.g., array hybridization), gel shifts, and nucleic acid sequencing. The fluorescently labeled polynucleotides can be used in solution phase or immobilized on a substrate.

In one embodiment, the labeled polynucleotides are used as hybridization probes. One application of hybridization probes is fluorescent in situ hybridization (FISH). In this technique, a labeled polynucleotide complementary to a sequence of interest is annealed to fixed chromosomes preparations, and the presence of the sequence of interest as well as the chromosomal localization is detected by microscopy. FISH can be performed by immobilizing the nucleic acids of interest on a substrate including without limitation glass, silicon, or fiber. FISH may also be used quantitatively (Q-FISH) to detect the presence and length of repetitive sequences such as telomeres. This may be done by quantitating the intensity of emitted fluorescence as measured by microscopy. FISH assays utilizing the subject fluorescent compounds can be performed for detecting a specific segment of a DNA molecule or a chromosome. These features can be used in genetic counseling (e.g., prenatal-screens), medicine, and species identification.

In some embodiments, labeled polynucleotides can be used as primers in amplification reactions such as PCR. In yet another embodiment, a compound of the invention may be used to label a polynucleotide which is subsequently used as a probe may be a hybridization probe or a real-time PCR probe. Such a probe may be labeled with a second fluorescent group to form a FRET pair with the first fluorescent group of the invention. Methods for the preparation and use of PCR probes are well known to one skilled in the art.

In one embodiment of the invention, a method is provided for detecting or quantifying a target nucleic acid, the method comprising the steps of: a) providing a labeled polynucleotide ("probe") of the present invention; b) contacting said labeled polynucleotide with the nucleic acid target so as to allow for hybridization of the probe with the nucleic acid target; and c) detecting or quantifying said nucleic acid target by measuring a change in the fluorescence of the probe upon the hybridization of the nucleic acid probe with the nucleic acid target.

As used herein, hybridization occurs when the probe form a complex with the target nucleic acid. In general, the complex is stabilized, at least in part, via hydrogen bonding between the bases of the nucleotide residues. The hydrogen bonding may occur by Watson-Crick base pairing, Hoogstein binding, or in any other sequence-specific manner. Hybridization may constitute a step in a more extensive process, such as the initiation of a PCR reaction, or the enzymatic cleavage of a polynucleotide by a ribozyme.

After hybridization between the probe and the target has occurred, a change in the intensity of the fluorescence of the probe may be measured. Such change before and after hybridization can yield a positive gain or negative reduction in the detected signal intensity. Depending on the specific hybridization assay that is run, more than one event after hybridization may contribute to the generation of a change in signal intensity. For example, an increase in reporter signal may result by way of spatial extension or separation of the reporter fluorescent group from the quencher group while both are still attached to the probe. In addition, either the reporter or the quencher of the probe can be separated by way of cleavage via an enzyme (e.g., a polymerase having a 5' to 3' exonuclease), thereby generating a reporter signal that is detected. As noted above, both the reporter and the quencher are defined in functional terms, such that these groups can be identical though serving, relative to each other, a different function when used in a hybridization reaction. For example, a group attached to a probe is a quencher because it reduces the emission of an optical signal when the probe is not hybridized with the target nucleic acid (typically when the probe assumes a random state). The same group can become a reporter fluorescent group upon being cleaved by an enzyme after hybridization with the target nucleic acid as the signal of the fluorescent group is now detected during the assay.

The signal detection methods described previously can be applied to nucleic acid amplification in which the target nucleic acid is increased in copy number. Such increase may occur in a linear or in an exponential manner. Amplification may be carried out by natural or recombinant DNA polymerases such as Taq polymerase, Pfu polymerase, T7 DNA polymerase, Klenow fragment of E. coli DNA polymerase, Tma DNA polymerase, exo-Tli DNA polymerase, exo-KOD DNA polymerase, exo-JDF-3 DNA polymerase, exo-PGB-D DNA polymerase, UITma (N-truncated) Thermatoga martima DNA polymerase, Sequenase, and/or RNA polymerases such as reverse transcriptase.

A preferred amplification method is polymerase chain reaction (PCR). General procedures for PCR are taught in U.S. Pat. Nos. 4,683,195 (Mullis) and 4,683,202 (Mullis et al.). Briefly, amplification of nucleic acids by PCR involves repeated cycles of heat-denaturing the DNA, annealing two primers to sequences that flank the target nucleic acid segment to be amplified, and extending the annealed primers with a polymerase. The primers hybridize to opposite strands of the target nucleic acid and are oriented so that the synthesis by the polymerase proceeds across the segment between the primers, effectively doubling the amount of the target segment. Moreover, because the extension products are also complementary to and capable of binding primers, each successive cycle essentially doubles the amount of target nucleic acids synthesized in the previous cycle. This results in exponential accumulation of the specific target nucleic acids at approximately a rate of $2^n$, where n is the number of cycles.

A typical conventional PCR thermal cycling protocol comprises 30 cycles of (a) denaturation at a range of 90° C. to 95° C. for 0.5 to 1 minute, (b) annealing at a temperature ranging from 50° C. to 65° C. for 1 to 2 minutes, and (c) extension at 68° C. to 75° C. for at least 1 minute. Other protocols including but not limited to universal protocol as well as fast cycling protocol can be performed the subject probes as well.

A variant of the conventional PCR is a reaction termed "Hot Start PCR". Hot Start PCR techniques focus on the inhibition of polymerase activity during reaction preparation. By limiting polymerase activity prior to PCR cycling, non-specific amplification is reduced and the target yield is increased. Common methods for Hot Start PCR include chemical modifications to the polymerase (see, e.g., U.S. Pat. No. 5,773,258), inhibition of the polymerase by a polymerase-specific antibody (see, e.g., U.S. Pat. No. 5,338,671), and introduction of physical barriers in the reaction site to sequester the polymerase before the thermal cycling takes place (e.g., wax-barrier methods). The reagents necessary for performing Hot Start PCR are conveniently packaged in kits that are commercially available (see, e.g., Sigma's JumpStart Kit).

Another variation of the conventional PCR that can be performed with the subject probes is "nested PCR" using nested primers. The method is preferred when the amount of target nucleic acid in a sample is extremely limited for example, where archival, forensic samples are used. In performing nested PCR, the nucleic acid is first amplified with an outer set of primers capable of hybridizing to the sequences flanking a larger segment of the target nucleic acid. This amplification reaction is followed by a second round of amplification cycles using an inner set of primers that hybridizes to target sequences within the large segment.

The subject probes can be employed in reverse transcription PCR reaction (RT-PCR), in which a reverse transcriptase first coverts RNA molecules to double stranded cDNA molecules, which are then employed as the template for subsequent amplification in the polymerase chain reaction. In carrying out RT-PCR, the reverse transcriptase is generally added to the reaction sample after the target nucleic acids are heat denatured. The reaction is then maintained at a suitable temperature (e.g., 30° C.-45° C.) for a sufficient amount of time (e.g., 5-60 minutes) to generate the cDNA template before the scheduled cycles of amplification take place. Such reaction is particularly useful for detecting the biological entity whose genetic information is stored in RNA molecules. Non-limiting examples of this category of biological entities include RNA viruses such as HIV and hepatitis-causing viruses. Another important application of RT-PCR embodied by the present invention is the simultaneous quantification of biological entities based on the mRNA level detected in the test sample.

The subject probes can also be employed to perform ligase chain polymerase chain reaction (LCR-PCR). The method involves ligating the target nucleic acids to a set of primer pairs, each having a target-specific portion and a short anchor sequence unrelated to the target sequences. A second set of primers containing the anchor sequence is then used to amplify the target sequences linked with the first set of primers. Procedures for conducting LCR-PCR are well known to artisans in the field, and hence are not detailed herein (see, e.g., U.S. Pat. No. 5,494,810).

The subject probes are particularly suited for use in a homogeneous assay. In such an assay, a target nucleic acid is detected and/or quantified without the requirement of post-assay processing to record the result of the assay. For example, a homogeneous PCR reaction can be carried out in a closed sample holder (e.g., a tube, a sample capillary or thermalchip), and no further addition or removal of reagents is necessary to record the result once the assay is started. Homogeneous assays allow recordation of the result of the assay in real time. Where desired, in practicing the subject methods, the result of the assay can be continuously recorded as the assay progresses in time or recorded intermittently at one or more point during the assay or upon completion of the assay.

Where desired, homogeneous assays can be multiplexed, i.e., more than one target nucleic acid can be detected in one assay. In a multiplex assay, two or more specific nucleic acid probes, which differ in the nature of their covalently attached fluorescent groups, are added to the mixture to be assayed. The fluorescent groups are chosen to produce distinguishable fluorescent signals from each specific nucleic acid probe. The signals of the different fluorescent group combinations of the nucleic acid probes can be recorded simultaneously to detect and/or quantify the corresponding target nucleic acids. Multiplexing greatly reduces the cost of analysis and can tremendously increase throughput in high volume settings.

The subject probes can be used to detect single mutations. Accordingly, methods are provided to use the probes of the invention to detect as few as a single mismatch between the probe sequence and a target sequence. Such high specificity in nucleic acid detection by PCR is highly valuable in clinical diagnosis and genetic research. For example, many diseases are associated with single mutations at different sites in the human genome. Although in theory this type of genetic variations, also called single nucleotide polymorphism or SNP, may be detected by sequencing, such sequencing method is not expected to be practical on a large scale due to high cost and low efficiency. Detection of SNP by an amplification reaction is feasible with the use of the subject probes.

The subject probes are also particularly suited for monitoring nucleic acid amplification reactions. In a related embodiment, the present invention provides a method of monitoring the increase in a target nucleic acid during amplification of said target. The method typically involves a) providing an amplification reaction mixture that comprises said target nucleic acid, at least one primer that hybridizes to the target nucleic acid, a labeled oligonucleotide probe of the present invention that provides a detectable signal, the intensity of which is proportional to the increase in the target nucleic acid in the amplification; (b) treating said mixture under conditions for amplifying said target nucleic acid; and (c) measuring the amount of said signal produced by said mixture during said treating step (c). Where desired, the amount of signal is determined continuously throughout the amplification reaction or determined intermittently during the amplification reaction. The amplification can be exponentially with the use of a primer pair or linearly with the use of one primer of the pair.

The increase in signal intensity during the amplification reaction may due to the step of hybridization of the probe to the target nucleic acid and also the step of cleavage via the action of the polymerase utilized in the amplification reaction.

In one aspect, the subject methods exploit the 5' to 3' nuclease activity of a polymerase when used in conjunction with PCR. When the subject probe is added concomitantly with the primer at the start of PCR, and the signal generated from hydrolysis of the labeled nucleotide(s) of the probe provides a means for detection of the target sequence during its amplification. Numerous polymerases are suited to catalyze primer and template-dependent nucleic acid synthesis and possess the 5' to 3' nuclease activity. Non-limiting examples include DNA polymerases such as $E.$ $coli$ DNA polymerase I, $Thermus$ $thermophilus$ (Tth) DNA polymerase, $Bacillus$ $stearothermophilus$ DNA polymerase, $Thermococcus$ $littoralis$ DNA polymerase, and $Thermus$ $aquaticus$ (Taq) DNA polymerase. Where desired, temperature stable polymerases can be employed in a nucleic acid amplification reaction. See, e.g., U.S. Pat. No. 4,889,818 that discloses a representative thermostable enzyme isolated from $Thermus$ $aquaticus$. Additional representative temperature stable polymerases include without limitation, e.g., polymerases extracted from the thermostable bacteria $Thermus$ $flavus,$ $Thermus$ $tuber,$ $Thermus$ $thermophilus,$ $Bacillus$ $stearothermophilus$ (which has a somewhat lower temperature optimum than the others listed), $Thermus$ $lacteus,$ $Thermus$ $rubens,$ $Thermotoga$ $maritima,$ $Thermococcus$ $littoralis$, and $Methanothermus$ $fervidus.$ In another embodiment, nucleic acid amplification can be performed with polymerases that exhibit strand-displacement activity (also known as rolling circle polymerization). Strand displacement can result in the synthesis of tandem copies of a circular DNA template, and is particularly useful in isothermal PCR reaction. Non-limiting examples of rolling circle polymerases suitable for the present invention include but are not limited to T5 DNA polymerase (Chatterjee et al., Gene 97:13-19 (1991)), and T4 DNA polymerase holoenzyme (Kaboord and Benkovic, Curr. Biol. 5:149-157 (1995)), phage M2 DNA polymerase (Matsumoto et al., Gene 84:247 (1989)), phage PRD1 DNA polymerase (Jung et al., Proc. Natl. Aced. Sci. USA 84:8287 (1987), and Zhu and Ito, Biochim. Biophys. Acta. 1219:267-276 (1994)), Klenow fragment of DNA polymerase I (Jacobsen et al., Eur. J. Biochem. 45:623-627 (1974)).

A preferred class of rolling circle polymerases utilizes protein priming as a way of initiating replication. Exemplary polymerases of this class are modified and unmodified DNA polymerase, chosen or derived from the phages (Φ29, PRD1, Cp-1, Cp-5, Cp-7, Φ15, Φ1, Φ21, Φ25, BS 32 L17, PZE, PZA, Nf, M2Y (or M2), PR4, PR5, PR722, B103, SF5, GA-1, and related members of the Podoviridae family. Specifically, the wildtype bacteriophage Φ29 genome consists of a linear double-stranded DNA (dsDNA) of 19,285 base pairs, having a terminal protein (TP) covalently linked to each 5' end. To initiate replication, a histone-like viral protein forms a nucleoprotein complex with the origins of replication that likely contributes to the unwinding of the double helix at both DNA ends (Serrano et al., The EMBO Journal 16(9): 2519-2527 (1997)). The DNA polymerase catalyses the addition of the first dAMP to the hydroxyl group provided by the TP. This protein-primed event occurs opposite to the second 3' nucleotide of the template, and the initiation product (TP-dAMP) slides back one position in the DNA to recover the terminal nucleotide After initiation, the same DNA polymerase replicates one of the DNA strands while displacing the other. The high processivity and strand displacement ability of Φ29 DNA polymerase makes it possible to complete replication of the Φ29 TP-containing genome (TP-DNA) in the absence of any helicase or accessory processivity factors (reviewed by Serrano et al., The EMBO Journal 16(9): 2519-2527 (1997)).

Strand displacement can be enhanced through the use of a variety of accessory proteins. They include but are not limited to helicases (Siegel et al., J. Biol. Chem. 267:13629-13635 (1992)), herpes simplex viral protein ICP8 (Skaliter and Lehman, Proc. Natl, Acad. Sci. USA 91(22):10665-10669 (1994)), single-stranded DNA binding proteins (Rigler and Romano, J. Biol. Chem. 270:8910-8919 (1995)), adenovirus DNA-binding protein (Zijderveld and van der Vliet, J. Virology 68(2):1158-1164 (1994)), and BMRF1 polymerase accessory subunit (Tsurumi et al., J. Virology 67(12):7648-7653 (1993)).

The subject probes can be utilized in an isothermal amplification reaction. Such amplification reaction does not rely solely upon thermal cycling. The procedure can be applied at a wide range of ambient temperatures. In particular, denaturation of the double-stranded template sequence is not accomplished solely through an increase in temperature above the melting temperature of the double stranded sequence. Rather, the denaturation process involves physical or mechanical force that separates the strand to allow primer annealing and extension. Various mechanisms for conducting isothermal amplification reaction including isothermal PCR are described in US. Patent Publication No 20060019274 and U.S. Pat. Nos. 5,824,477 and 6,033,850, which are incorporated herein by reference.

Nucleic acid amplification is generally performed with the use of amplification reagents. Amplification reagents typically include enzymes, aqueous buffers, salts, primers, target nucleic acid, and nucleoside triphosphates. Depending upon the context, amplification reagents can be either a complete or incomplete amplification reaction mixture.

The choice of primers for use in nucleic acid amplification will depend on the target nucleic acid sequence. Primers used in the present invention are generally oligonucleotides, e.g., 10 to 100 or 10 to 25 bases in length, that can be extended in a template-specific manner via the action of a polymerase. In general, the following factors are considered in primer design: a) each individual primer of a pair preferably does not self-hybridize in an amplification reaction; b) the individual pairs preferably do not cross-hybridize in an amplification reaction; and c) the selected pair must have the appropriate length and sequence homology in order to anneal to two distinct regions flanking the nucleic acid segment to be amplified. However, not every nucleotide of the primer must anneal to the template for extension to occur. The primer sequence need not reflect the exact sequence of the target nucleic acid. For example, a non-complementary nucleotide fragment may be attached to the 5' end of the primer with the remainder of the primer sequence being complementary to the target. Alternatively, non-complementary bases can be interspersed into the primer, provided that the primer sequence has sufficient complementarily with the target for annealing to occur and allow synthesis of a complementary nucleic acid strand.

A nucleic acid amplification reaction typically comprises a target nucleic acid in a buffer compatible with the enzymes used to amplify the target. The buffer typically contains nucleotides or nucleotide analogs (ATP, TTP, CTP, GTP, or analogs thereof including without limitation pentaphosphates having the respective base unit) that are capable of being incorporated into a replica strand of the template sequence.

Where desired, amplification reaction is carried out as an automated process. Numerous thermocyclers are available in the art that are capable of holding 48, 96 or more samples. A suitable optical system moves the excitation light from the source to the reaction sites and measures the emission light from each sample. For example, multiple fiber optic leads simultaneously read all PCR tubes undergoing thermocycling. However, only a single fluorometer may be needed to read fluorescence from the reaction sites. An analogous detection scheme is suitable in a 96-well microtiter format. This type of format is frequently desirable in clinical laboratories for large scale sample screening, for example, for genetic analysis such as screening for AIDS virus in blood bank screening procedures.

Accordingly, the present invention also provides an apparatus for detecting the signal generated by the subject probe, which can be used to detect, measure, and quantify the signal before, during, and after amplification. The apparatus comprises a thermal unit (e.g., a thermocycler) capable of holding an amplification reaction mixture comprising the subject probes and effecting an amplification of the target sequence, and a detector that detects the signal generated from the subject probes.

In another embodiment of the present invention, the subject probes are employed in assays that are conducted on nucleic acid microarrays to detect or quantify nucleic acid targets. In such assays, a fluorescent signal is generated on a nucleic acid microarray upon the presence of a complementary target nucleic acid.

Nucleic acid microarrays including gene chips comprise ordered arrays of nucleic acids that are covalently attached to a solid surface, see e.g., U.S. Pat. Nos. 5,871,928, 6,040,193, 6,262,776, 6,403,320, and 6,576,424. The fluorescent signal that is generated in the assay can be monitored and quantified with optical detectors including but not limited to fluorescence imagers, e.g. commercial instruments supplied by Hitachi Corp., San Bruno, Calif. or confocal laser microscopes (confocal fluorescence scanners), e.g. commercial instruments from General Scanning, Inc., Watertown, Mass.

In assays that are conducted on nucleic acid microarrays, the target nucleic acids may be provided as a mixture of nucleic acid sequences derived from any suitable biological sources. They can be derived from body fluid, solid tissue samples, tissue cultures or cells derived therefrom and the progeny thereof, and sections or smears prepared from any of these sources, or any other samples that contain nucleic acids.

Where expression pattern is assayed, the mRNA sequences are first typically amplified by reverse transcription PCR with universal primers prior to their use as the target sequences in the assay. In one embodiment, all nucleic acid sequences present in the test sample are simultaneously applied to the microarray for analysis, thus allowing the interaction of all target nucleic acid sequences with all nucleic acids that are present on the array. In another embodiment, the target nucleic acids applied to the array are pre-selected to yield a subset for refined hybridization analysis utilizing a microarray. For example, a limited number of target sequences can contain more than one stretch of specific nucleotide sequence to be analyzed, e.g. more than one single nucleotide polymorphism. The nucleic acid sequences of this setting may be amplified by PCR with the aid of specific primers prior to their analysis on the microarray.

In assaying for expression of multiples genes of a subject, target polynucleotides are allowed to form stable complexes with probes on the aforementioned arrays in a hybridization reaction. It will be appreciated by one of skill in the art that where antisense RNA is used as the target nucleic acid, the sequence immobilized on the array are chosen to be complementary to sequences of the antisense nucleic acids. Conversely, where the target nucleic acid pool is a pool of sense nucleic acids, the sequence immobilized on the array are selected to be complementary to sequences of the sense nucleic acids. Finally, where the nucleic acid pool is double stranded, the probes may be of either sense and/or antisense as the target nucleic acids include both sense and antisense strands.

In one embodiment, labeled probes are utilized to perform a competitive hybridization on a microarray. In this assay format, a target nucleic acid from a test sample competes with a probe of the present invention for binding of a known sequence immobilized on the microarray. The amount of labeled probes that will bind to the immobilized known sequences is inversely proportional to the concentration of corresponding target nucleic acids in the test sample.

A variant hybridization assay involves the use of polymerases on a microarray to enhance the signals of the probes by performing cleavage of the reporters. For example, a mixture of target sequences are first allowed to hybridize with known sequences immobilized on the array. Unhybridized sequences are then washed away. Thereafter, probes corresponding to the target sequences are allowed to hybridize to different regions on the targets. Upon washing of the excessive unbound probes, the reporter fluorescent groups on the hybridized probes are cleaved via the action of polymerases, thereby generating a detectable signal that is indicative of the presence and/or quantity of a target sequence initially present in the test sample.

Suitable hybridization conditions for use of the labeled probes of the invention are such that the recognition interaction between the sequence on the array and target is both sufficiently specific and sufficiently stable. As noted above, hybridization reactions can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art. See, for example, (Sambrook, et al., (1989), supra).

In general, there is a tradeoff between hybridization specificity (stringency) and signal intensity. In a preferred embodiment, washing the hybridized array prior to detecting the target-probe complexes is performed to enhance the signal to noise ratio. Typically, the hybridized array is washed at successively higher stringency solutions and signals are read between each wash. Analysis of the data sets thus produced will reveal a wash stringency above which the hybridization pattern is not appreciably altered and which provides adequate signal for the particular polynucleotide probes of interest. Parameters governing the wash stringency are generally the same as those of hybridization stringency. Other measures such as inclusion of blocking reagents (e.g. sperm DNA, detergent or other organic or inorganic substances) during hybridization can also reduce non-specific binding.

Imaging specific hybridization event on a microarray is typically performed with the aid of an optical system. Non-limiting examples of suitable systems include camera, charge couple device (CCD), electron-multiplying charge-coupled device (EMCCD), intensified charge coupled device (ICCD), and confocal microscope.

The microarray provides a positional localization of the sequence where hybridization has taken place. The position of the hybridized region correlates to the specific sequence, and hence the identity of the target expressed in the test sample. The detection methods also yield quantitative measurement of the level of hybridization intensity at each hybridized region, and thus a direct measurement of the level of expression of a given gene transcript. A collection of the data indicating the regions of hybridization present on an array and their respective intensities constitutes a hybridization pattern that is representative of a multiplicity of expressed gene transcripts of a subject. Any discrepancies detected in the hybridization patterns generated by hybridizing target polynucleotides derived from different subjects are indicative of differential expression of a multiplicity of gene transcripts of these subjects.

In one aspect, the hybridization patterns to be compared can be generated on the same array. In such case, different patterns are distinguished by the distinct types of detectable labels. In a separate aspect, the hybridization patterns employed for the comparison are generated on different arrays, where discrepancies are indicative of a differential expression of a particular gene in the subjects being compared.

The test nucleic acids for a comparative hybridization analysis can be derived from (a) cells from different organisms of the same species (e.g. cells derived from different humans); (b) cells derived from the same organism but from different tissue types including normal or disease tissues, embryonic or adult tissues; (c) cells at different points in the cell-cycle; (d) cells treated with or without external or internal stimuli. Thus, the comparative hybridization analysis using the arrays of the present invention can be employed to monitor gene expression in a wide variety of contexts. Such analysis may be extended to detecting differential expression of genes between diseased and normal tissues, among different types of tissues and cells, amongst cells at different cell-cycle points or at different developmental stages, and amongst cells that are subjected to various environmental stimuli or lead drugs. Therefore, the expression detecting methods of this invention may be used in a wide variety of circumstances including detection of disease, identification and quantification of differential gene expression between at least two samples, linking the differentially expressed genes to a specific chromosomal location, and/or screening for compositions that upregulate or downregulate the expression or alter the pattern of expression of particular genes.

The subject amplification and any other hybridization assays described herein can be used to detect any target nucleic acids from any sources suspected to contain the target. It is not intended to be limited as regards to the source of the sample or the manner in which it is made. Generally, the test sample can be biological and/or environmental samples. Biological samples may be derived from human or other animals, body fluid, solid tissue samples, tissue cultures or cells derived therefrom and the progeny thereof, sections or smears prepared from any of these sources, or any other samples that contain nucleic acids. Preferred biological samples are body fluids including but not limited to urine, blood, cerebrospinal fluid, spinal fluid, sinovial fluid, semen, ammoniac fluid, cerebrospinal fluid (CSF), and saliva. Other types of biological sample may include food products and ingredients such as dairy items, vegetables, meat and meat by-products, and waste. Environmental samples are derived from environmental material including but not limited to soil, water, sewage, cosmetic, agricultural and industrial samples, as well as samples obtained from food and dairy processing instruments, apparatus, equipment, disposable, and non-disposable items.

Polynucleotides labeled according to the invention may also be used in gel shift assays. Such an assay, also known as electrophoretic mobility shift assay (EMSA), gel mobility shift assay, band shift assay, or gel retardation assay, is a common technique used to study protein-DNA or protein-RNA interactions. This procedure can determine if a protein or mixture of proteins is capable of binding to a given DNA or RNA sequence, and can sometimes indicate if more than one protein molecule is involved in the binding complex. Labeled oligonucleotides may be used in gel shift assays by peforming electrophoresis and subsequently determining the extent of migration of the labeled oligonucleotides in the gel by visualizing the emission of the fluorescent label. Gel shift assays may be performed in vitro concurrently with DNase footprinting, primer extension, and promoter-probe experiments when studying transcription initiation, DNA replication, DNA repair or RNA processing and maturation. Methods of performing gel shift assays are known. See, e.g. Garner, M. M. and Revzin, A. (1981) "A gel electrophoresis method for quantifying the binding of proteins to specific DNA regions: application to components of the Escherichia coli lactose operon regulatory system." Nucleic Acids Res. 9:3047-3060 or Fried, M. and Crothers, D. M. (1981) "Equilibria and kinetics of lac repressor-operator interactions by polyacrylamide gel electrophoresis." Nucleic Acids Res., 9:6505-6525.

Fluorescently labeled polypeptides of the invention are useful in a wide variety of assays. Such assays can be performed to discern specific protein-protein interactions, protein-nucleic acid interaction, interactions between a protein of interest and candidate inhibitors or activators. Candidate inhibitors or activators include but are not limited to antisense oligonucleotides, double stranded RNAs, ribozymes, a ribozyme derivatives, antibodies, liposomes, small molecules, inorganic or organic compounds. The subject assays can also be performed to study enzymatic kinetics, for e.g., drug design, screen and/or optimization and can be performed using the fluorescently labeled polypeptides in solution or immobilized on a solid substrate.

Of particular interest is a specific interaction between a cell surface receptor and its corresponding ligand. Cell surface receptors are molecules anchored on or inserted into the cell plasma membrane. They constitute a large family of proteins, glycoproteins, polysaccharides and lipids, which serve not only as structural constituents of the plasma membrane, but also as regulatory elements governing a variety of biological functions. In another aspect, the specific protein-protein interaction involves a cell surface receptor and an immunoliposome or an immunotoxin. In yet another aspect, the specific protein-protein interaction may involve a cytosolic protein, a nuclear protein, a chaperon protein, or proteins anchored on other intracellular membranous structures. In yet another aspect, the specific protein-protein interaction is between a target protein (e.g., an antigen) and an antibody specific for that antigen.

A specific interaction between a labeled polypeptide and an interacting entity is assayed by mixing the two entities under conditions such interaction is suspected to occur. Typically, the interaction is visualized with the aid of an optical device. Where desired, these entities can be placed within an optical confinement (see, e.g., U.S. Pat. Nos. 7,267,673, and 7,170,050). Where single molecule is to be detected, each optical confinement contains only one target that is being investigated. This can be achieved by diluting a minute amount of target in a large volume of solution, such that deposition over an array of confinements results in a primary distribution, or a majority of confinements will have a single target molecule disposed there. The labeled polypeptide and the interacting entity can be immobilized onto the inner surface of the optical confinement by any of the methods available in the art. Such methods encompass the uses of covalent and noncovalent attachments effected by a variety of binding moieties. The choice of the binding moieties will depend on the nature of the labeled polypeptide and/or the interacting entity. One way to immobilize the labeled polypeptide or the proteinaceous probe involves the use of the streptavidin or avidin/biotin binding pair.

In one embodiment, the polypeptide to be reacted with a compound of the invention comprises 3 to about 80 amino acids. Examples of such polypeptides include, but are not limited to, neuropeptides, cytokines, toxins and peptidase or protease substrates. Fluorescently labeled-neuropeptides, -cytokines and -toxins may be used to map or visualize the distribution of the receptors specific to the respective peptides. As an example, when labeled with a compound of the invention, phalloidin, which is a toxin with a cyclic peptide structure, can be used to stain F-actin filaments in cells. As another example, when labeled with a fluorescent group of the invention, α-bungarotoxin, a peptide-based snake toxin, can be used to detect acetylcholine receptor. Peptidase or protease substrates labeled with a fluorescent group of the invention may be used to assay the activities of the peptidases or proteases, and used in screening drugs designed as inhibitors of the peptidases or proteases. For example, a peptide comprising a peptide sequence cleavable by a peptidase may be labeled at one end of the peptide sequence with a first fluorescent group, a fluorescence donor fluorescent group, selected from a fluorescent group of the invention and at the other end of the peptide sequence with a second fluorescent group, a fluorescence acceptor fluorescent group (such as another fluorescent group from the invention or a quencher), where the first dye and second dye form a fluorescence resonance energy transfer (FRET) pair. By detecting the fluorescence difference of either the donor fluorescent group or the acceptor fluorescent group of the FRET pair before and after the peptide is cleaved by said peptidase, the level of enzyme activity can be assessed.

Other polypeptide conjugates that can be prepared according to the invention include those of antibodies, lectins, enzymes, lipoproteins, albumins, avidin, streptavidin, annexins; protein A, protein G, transferrin, apotransferrin, phycobiliproteins and other fluorescent proteins, toxins, growth factors, tubulins, hormones, various receptors and ion channels.

In one embodiment, compounds of the invention may be reacted with antibodies. Such antibodies may be primary or secondary depending on the desired application. If the antigen to be detected is present in very small amounts, a secondary antibody may be used in order to provide signal amplification. Various secondary antibody isotypes may be labeled. Non-limiting examples of secondary antibody isotypes are Anti-mouse IgG, Anti-mouse IgM, Anti-rabbit IgG, Anti-rat IgG, Anti-rat IgM, Anti-guinea pig IgG, Anti-chicken IgG, Anti-hamster IgG, Anti-human IgG, Anti-human IgM, Anti-goat IgG, Anti-mouse IgG, Anti-rabbit IgG, Anti-rat IgG, Anti-sheep IgG, Anti-goat IgG, Anti-mouse IgG, Anti-human IgG, Anti-rat IgG, Anti-mouse IgG, Anti-human IgG, Anti-rat IgG, Anti-goat IgG, and Anti-rabbit IgG.

Alternatively, Fab fragments may be labeled with the compounds of the invention. Such fragments may be superior to whole antibody conjugates because they lack the Fc region, which would reduce nonspecific interactions with Fc receptor-bearing cell membranes and would allow better penetration into tissues.

Labeled secondary antibodies of the invention may be used in signal amplification kits such as those commercialized by Molecular Probes, Inc. Such kits could each provide two labeled antibodies specific to a primary antibodies, such as a mouse antibody. In one embodiment, a rabbit anti-mouse IgG antibody conjugate of the invention is first used to bind to the mouse-derived primary antibody. The fluorescence is then dramatically enhanced by the addition of a second conjugate of a goat anti-rabbit IgG antibody.

In yet another embodiment, the compounds of the invention may be used to label protein A and/or protein G. Protein A and protein G are bacterial proteins that bind with high affinity to the Fc portion of various classes and subclasses of immunoglobulins from a variety of species, such as Bovine, Cat, Chicken, Dog, Goat, Guinea pig, Horse, Human IgG1, IgG2, IgG3, IgG4, Human IgM, IgA, IgE, Human IgD, Mouse IgG1 or others, Pig, Rabbit, Rat or Sheep, which may be used in the detection of immunoglobulins. Alternatively, immunoglobins can be labeled with a compound of the invention having a structure of Formula I, III, IV, V or VI and retains binding specificity to its target after such labeling. These labeled immunoglobins can be used for in-vitro or in-vivo detection of the target antigen. In various embodiments of the invention, such labeled immunoglobins bind to an antigen on a cancer cell. In some embodiments, the labeled immunoglobin binds to erb2.

Labeled antibodies prepared according to the invention may be primary antibodies for various applications. While secondary detection methods can provide significant signal amplification, a directly labeled primary antibody often produces lower background fluorescence and less nonspecific binding. Using primary antibodies also allows multiple primary antibodies of the same isotype or derived from the same species to be used in the same experiment when they are directly labeled.

Examples of such primary antibodies include polyclonal antibodies specific for reporter gene products. These include Anti-Green-Fluorescent Protein Antibodies, Anti-Glutathione S-Transferase Antibody, Anti-beta-Glucuronidase Antibody, Anti-beta-Galactosidase Antibody, Monoclonal Antibodies Specific for Epitope Tags, Penta•His Antibody, Anti-HA Antibody and Anti-c-myc Antibody.

Organelle-specific labeled antibodies may also be prepared to label various subcellular organelles and components such as the endoplasmic reticulum, peroxisomes, mitochondria, or cytochrome c. Labeled antibodies may also be specific for proteins in the oxidative phosphorylation system, such as antibodies against cytochrome oxidase (Complex IV) or antibodies against Complexes I, II, III and V, or other mitochondrial proteins such as anti-mitochondrial porin antibodies or anti-pyruvate dehydrogenase antibodies.

In other embodiments, labeled antibodies specific for proliferation markers and cell-cycle control proteins may be prepared. Such antibodies include Anti-Bromodeoxyuridine Antibody (Anti-BrdU Antibody), which may for example be used in TUNEL assays, Anti-Human mRNA-Binding Protein HuR Antibody (Anti-HuR Antibody), Anti-Human Neuronal Protein HuC/HuD Antibody (Anti-Hu Antibody), Anti-cdc6 Peptide Antibody, Anti-CD Antibodies, Antibodies against D Cyclins/Cyclin-Dependent Kinase Inhibitors, and Anti-Phosphoinositide Antibodies.

Some labeled antibodies may be specific for structural cellular proteins. Examples of such antibodies are Anti alpha-Tubulin Monoclonal Antibody, Anti-Glial Fibrillary Acidic Protein (GFAP) Antibody, Anti-Desmin Antibody, or Anti-Fibronectin Antibody. Additional antibodies suitable for use in the invention include antibodies specific for neuronal proteins such as Anti-Synapsin I Antibody or Anti-NMDA Receptor Antibodies. Other Polyclonal and Monoclonal Antibodies that may be labeled according to the invention include Anti-Human Golgin-97 Antibody, Anti-Human Transferrin Receptor Antibody, Antibodies against Matrix Metalloproteinases and Anti-Bovine Serum Albumin Antibody.

The specific interaction between an antigen and an antibody has been explored in the context of immunoassays utilizing the subject fluorescent compounds. The immunoassays can permit single-molecule detection or ensemble detection. The subject immunoassays can be performed to characterize biological entities, screen for antibody therapeutics, and determine the structural conformations of a target antigen. For instance, immunoassays involving antibodies that are specific for the biological entity or specific for a by-product produced by the biological entity have been routinely used to identify the entity by forming an antibody-entity complex. Immunoassays are also employed to screen for antibodies capable of activating or down-regulating the biological activity of a target antigen of therapeutic potential. Immunoassays are also useful for determining structural conformations by using anti-idiotypic antibodies capable of differentiating target proteins folded in different conformations.

According to one embodiment of the invention, biomolecules labeled with a fluorescent group of the invention such as proteins are suitable for in vivo imaging, including without limitation imaging a biomolecule present inside a cell, a cell, tissue, organ or a whole subject. Where desired, the labeled biomolecules can be used to perform "In Cell Western" in which given molecules (e.g., a specific cellular protein) present inside a cell are stained and imaged.

The fluorescent groups of the invention and/or the labeled biomolecules of the present invention can be administered to a subject in a variety of forms adapted to the chosen route of administration, i.e., orally, or parenterally. Parenteral administration in this respect includes, but is not limited to, administration by the following routes: intravenous, intramuscular, subcutaneous, parenteral, intraocular, intrasynovial, transepithelially including transdermal, opthalmic, sublingual, and buccal; topically including opthalmic, dermal, ocular, rectal and nasal inhalation via insufflation and aerosol and rectal systemic. In vivo imaging may provide means for early detection, screening, diagnosis, image-guided surgical intervention, and treatment of various diseases. For example, Near IR fluorescent group-labeled toxin (Veiseh, et al. *Cancer Res.* 67(14), 6882 (2007)) and antibody (Kulbersh, et al. *Arch Otolaryngol Head Neck Surg.* 133(5), 511 (2007) have been used to detect and guide the surgical removal of tumors. In in-vivo imaging, a fluorescent probe, such as an antibody labeled with a fluorescent group, is first administered to an animal (such as a mammal). The animal is then imaged by applying an excitation light with a wavelength appropriate for the absorption of the fluorescent group and collecting the fluorescence signal at another wavelength appropriate for the emission of the fluorescent group. Typically, for efficient tissue penetration of both the excitation and emission lights, the absorption and emission wavelengths of the fluorescent group may be greater than 470 nm, greater than 550 nm, greater than 600 nm, or greater than 640 nm.

In other embodiments of the invention, a method of in-vivo imaging of a subject is provided comprising the steps of administering to a subject in need thereof a biomolecule comprising a label having a structure of Formula I, III, IV, V, VI or VII wherein the at least one reactive moiety of label has undergone a reaction which attached the label to the biomolecule and wherein the biomolecule further comprises a targeting moiety that binds to a binding partner on a cell of the subject which is indicative of the cell; binding the binding partner on the cell with the targeting moiety of the biomolecule thereby differentially labeling the cell relative to neighboring cells; directing exciting wavelength to the cell; and detecting emitted fluorescence from the cell of the subject thereby detecting the differentially labeled cell of the subject. The biomolecule may be an antibody, fragment of an antibody, protein, peptide, lipid or carbohydrate.

The compounds of the invention may also be used to produce labeled biomolecules for use in immunohistochemistry and immunocytochemistry experiments. In immunohistochemistry (IHC), the presence and location of proteins is determined within a tissue section by exploiting the principle of an antibody binding specifically to an antigens present in a biological tissue. Such experiments may, for example, be used in the diagnosis and treatment of cancer. Specific molecular markers are characteristic of particular cancer types and are known to persons skilled in the art. IHC can also be used in basic research to determine the distribution and localization of biomarkers in different parts of a tissue. Visualization of antibody-antigen interactions can be accomplished by reacting an antibody with a reactive fluorescent compound of the invention and using the labeled antibody to stain tissue sections. In immunocytochemistry, the labeled antibody is used to stain populations of cultured cells. These techniques can be combined with confocal laser scanning microscopy, which is highly sensitive and can also be used to visualise interactions between multiple proteins. Subcellular localization of proteins may also be possible using confocal microscopy.

Of particular interest is the use of the labeled polypeptide for conducting immunocytochemistry. Fluorescence immunocytochemistry combined with fluorescence microscopy provides visualization of biomolecules such as proteins and nucleic acids within a cell. One method uses primary antibodies hybridized to the desired target. Then, secondary antibodies conjugated with the subject fluorescent dyes and targeted to the primary antibodies are used to tag the complex. The complex is visualized by exciting the dyes with a wavelength of light matched to the dye's excitation spectrum.

Immunocytochemistry can also be employed to discern subcellular localization of a given protein or nucleic acid. For instance, colocalization of biomolecules in a cell is performed using different sets of antibodies for each cellular target. For example, one cellular component can be targeted with a mouse monoclonal antibody and another component with a rabbit polyclonal antibody. These are designated as the primary antibody. Subsequently, secondary antibodies to the mouse antibody or the rabbit antibody, conjugated to different fluorescent dyes of the present invention having different emission wavelengths, are used to visualize the cellular target.

The compounds of the invention or the labeled biomolecules of the invention can also be used to label cells or particles for a variety of applications. Accordingly, the present invention provides a method of individually, labeling a cell within a population of cells whereby the cell is differentially labeled relative to neighboring cells within the population. The method typically comprises contacting the cell with a labeled biomolecule of the present invention, wherein said biomolecule comprises a targeting moiety that binds to a binding partner that is indicative of said cell, and thereby differentially labeling the cell relative to neighboring cells within the population. The targeting moiety can be any biomolecules that recognize a binding partner on the cell to be detected. The choice of the targeting moiety will vary depending on the cell that is to be labeled. For example, for detecting a cancer cell, a targeting moiety is selected such that its binding partner is differentially expressed on a cancer cell. A vast number of cancer markers are known in the art. They include without limitation cell surface receptors such as erb2, PDGF receptor, VEGF receptors, a host of intracellular proteins such as phosphatidylinositol 3-kinases, c-abl, raf, ras, as well as a host of nuclear proteins including transcription factors and other nucleic acid binding molecules. In some other embodiments, the cancer marker is Immunoglobulin epsilon Fc receptor II, Alk-1, CD20, EGF receptor, FGF receptor, NGF receptor, EpCam, CD3, CD4, CD11a, CD19, CD22, CD30, CD33, CD38, CD40, CD51, CD55, CD80, CD95, CCR2, CCR3, CCR4, CCR5, CTLA-4, Mucin 1, Mucin 16, Endoglin, Mesothelin receptor, Nogo receptor, folate receptor, CXCR4, insulin-like growth factor receptor, Ganglioside GD3, and alpha or beta Integrins. To differentially label various cell types, targeting moieties recognizing a cell-specific binding partner can be used. For example, there are a host of protein markers differentially expressed on T cells as opposed on B cells or other cells of different lineage. Neuronal markers, muscle cell markers, as well as markers indicative of cells of ectodermal, mesodermal or endodermal origins are also known in the art, all of which can be used depending on the intended applications. The targeting moieties can be antibodies, receptors, cytokines, growth factors, and any other moieties or combinations thereof that are recognized by a binding partner on the cell to be labeled. The cell which is labeled may be labeled intracellularly.

The differentially labeled cells can be imaged by directing exciting wavelength to the cell and detecting emitted fluorescence from the cell, in a number of in-vitro formats, either in solution or immobilized on a substrate.

The labeled cells and/or the intensity of the fluorescence may be detected or quantified by performing flow cytometry. Cells or particles labeled with the compounds of the invention or stained with labeled biomolecules of the invention may also be separated and isolated based on the specific properties of the label using fluorescence activated cell sorting (FACS). Such techniques are known in the art. Briefly, cells are labeled with a subject fluorescent dye and then passed, in a suspending medium, through a narrow dropping nozzle so that each cell is typically in a small droplet. A laser based detector system is used to excite fluorescence and droplets with positively fluorescent cells are given an electric charge. Charged and uncharged droplets are separated as they fall between charged plates and so collect in different tubes. The machine can be used either as an analytical tool, counting the number of labeled cells in a population or to separate the cells for subsequent growth of the selected population. Further sophistication can be built into the system by using a second laser system at right angles to the first to look at a second fluorescent label or to gauge cell size on the basis of light scatter.

Additional guidance for performing fluorescent cell sorting can be found in publications such as the following: Darzynkiewicz, Z., Crissman, H. A. and Robinson, J. P., Eds., Cytometry, Third Edition Parts A and B (Methods in Cell Biology, Volumes 63 and 64), Academic Press (2001); Davey, H. M. and Kell, D. B., "Flow cytometry and cell sorting of heterogeneous microbial populations: the importance of single-cell analyses," Microbiological Rev 60, 641-696 (1996); Givan, A. L., Flow Cytometry: First Principles, Second Edition, John Wiley and Sons (2001); Herzenberg, L. A., Parks, D., Sahaf, B., Perez, O., Roederer, M. and Herzenberg, L. A., "The history and future of the fluorescence activated cell sorter and flow cytometry: a view from Stanford," Clin Chem 48, 1819-1827 (2002); Jaroszeski, M. J. and Heller, R., Eds., Flow Cytometry Protocols (Methods in Molecular Biology, Volume 91), Humana Press (1997); Ormerod, M. G., Ed., Flow Cytometry: A Practical Approach, Third Edition, Oxford University Press (2000); Robinson, J. P., Ed., Current Protocols in Cytometry, John Wiley and Sons (1997); Shapiro, H. M., "Optical measurement in cytometry: light scattering, extinction, absorption and fluorescence," Meth Cell Biol 63, 107-129 (2001); Shapiro, H. M., Practical Flow Cytometry, Fourth Edition, Wiley-Liss (2003); Weaver, J. L., "Introduction to flow cytometry," Methods 21, 199-201 (2000).

Fluorescent compounds of the invention may also be used for fluorescence lifetime imaging (FLIM). FLIM is a useful technique for producing images based on the variation in the fluorescence decay characteristics of a fluorescent sample. It can be used as an imaging technique in confocal microscopy and other microscope systems. The lifetime of the fluorophore signal, rather than its intensity, is used to create the image in FLIM, which has the advantage of minimizing the effect of photon scattering in thick layers of sample. FLIM may be useful for biomedical tissue imaging, allowing to probe greater tissue depths than conventional fluorescence microscopy.

The compounds of the invention may be used in single molecule applications. Removal of ensemble averaging by observing individual molecules of fluorescent group may allow the determination of the mechanism of biological and chemical processes. Such processes may include the translocation of protein motors such as kinesin or myosin, formation, dissolution and translocation of cellular protein complexes and the mechanism of action of DNA or RNA polymerases. In such experiments, the present compounds may be used, for example, to label biomolecules which are attached to a surface such as a microscopy slide or flow chamber. Individual fluorophores may subsequently be observed using total internal reflection fluorescence microscopy.

The present compounds may also be used for the labeling of lipids. Lipids are involved in many biological processes, and the labeling of lipids and lipid rafts may is often a valuable method for studying their properties. Various lipid monolayers and bilayers may be labeled in live cells or artificial systems such as liposomes and micelles. For example, a live cell population may be labeled with a fluorescent conjugate prepared by reacting a compound of the invention and cholera toxin subunit B, which specifically interacts with lipid rafts. Such lipid rafts may then be crosslinked into distinct membrane patches by the use of an anti-cholera toxin antibody, which may be labeled with one of the present compounds.

The labeled polypeptides of the present invention find use as biosensors in prokaryotic and eukaryotic cells, e.g. as calcium ion indicators, as pH indicators, as phorphorylation indicators, as indicators of other ions including without limiting to magnesium, sodium, potassium, chloride and halides. For example, for detection of calcium ion, proteins containing an EF-hand motif are known to translocate from the cytosol to membranes upon binding to calcium ion. These proteins contain a myristoyl group that is buried within the molecule by hydrophobic interactions with other regions of the protein. Binding of calcium ion induces a conformational change exposing the myristoyl group which then is available for the insertion into the lipid bilayer. Labeling such an EF-hand containing protein with a subject fluorescent dye makes it an indicator of intracellular calcium ion concentration by monitoring the translocation from the cytosol to the plasma membrane. Such monitoring can be performed with the use of an optical detector, e.g., a confocal microscope. EF-hand proteins suitable for use in this system include, but are not limited to: recoverin (1-3), calcineurin B, troponin C, visinin, neurocalcin, calmodulin, parvalbumin, and the like.

For use as a pH indicator, a system based on hisactophilins may be employed. Hisactophilins are myristoylated histidine-rich proteins known to exist in Dictyostelium. Their binding to actin and acidic lipids is sharply pH-dependent within the range of cytoplasmic pH variations. In living cells membrane binding seems to override the interaction of hisactophilins with actin filaments. At pH of approximately 6.5 they typically locate to the plasma membrane and nucleus. In contrast, at pH 7.5 they evenly distribute throughout the cytoplasmic space. This change of distribution is reversible and is attributed to histidine clusters exposed in loops on the surface of the molecule. The reversion of intracellular distribution in the range of cytoplasmic pH variations is in accord with a pK of 6.5 of histidine residues. The cellular distribution is independent of myristoylation of the protein. By conjugating the subject fluorescent dye to hisactophilin, the intracellular distribution of the labeled hisactophilin can be followed by laser scanning, confocal microscopy or standard fluorescence microscopy. Quantitative fluorescence analysis can be done by performing line scans through cells (laser scanning confocal microscopy) or other electronic data analysis (e.g., using metamorph software (Universal Imaging Corp) and averaging of data collected in a population of cells.

The subject fluorescent proteins also find use in applications involving the automated screening of arrays of cells by using microscopic imaging and electronic analysis. Screening can be used for drug discovery and in the field of functional genomics: e.g., where the subject proteins are used as markers of whole cells to detect changes in multicellular reorganization and migration, e.g., formation of multicellular tubules (blood vessel formation) by endothelial cells, migration of cells through Fluoroblok Insert System (Becton Dickinson Co.), wound healing, neurite outgrowth; where the proteins are used as markers fused to peptides (e.g., targeting sequences) and proteins that allow the detection of change of intracellular location as indicator for cellular activity, for example: signal transduction, such as kinase and transcription factor translocation upon stimuli, such as protein kinase C, protein kinase A, transcription factor NFkB, and NFAT; cell cycle proteins, such as cyclin A, cyclin B1 and cyclinE; protease cleavage with subsequent movement of cleaved substrate, phospholipids, with markers for intracellular structures such as endoplasmic reticulum, Golgi apparatus, mitochondria, peroxisomes, nucleus, nucleoli, plasma membrane, histones, endosomes, lysosomes, microtubules, actin.

The subject fluorescent proteins also find use in high through-put screening assays. The subject fluorescent proteins are typically more stable than proteins lacking the subject fluorescent dyes. In some aspects, the fluorescent proteins can exhibit a serum half-life of more than 1 hour, 2 hours, 5 hours, or 24 hours or more.

The subject fluorescent proteins can be used as second messenger detectors, e.g., by conjugating the subject fluorescent dyes to specific signaling domains, e.g., calcium binding SH2-, SH3-, PH-, PDZ-domain and etc.

Detection of Target Ions

In some embodiments, a compound of the invention is used to detect the presence or concentration of a target ion. The optical response of the compound is determined by changes in absorbance or fluorescence. In some embodiments, the compound of the invention comprising a chelator shows at least a two-fold change in net fluorescence emission intensity (higher or lower), or a 1 nanosecond difference in fluorescence lifetime (either shorter or longer). In other embodiments, the compound shows a five-fold or greater change in net fluorescence emission intensity or a 100% change in fluorescence lifetime in response to the target ion. Alternatively, a compound that exhibits a shift in excitation or emission wavelength of at least 10 nm (either to shorter or longer wavelength) is also useful, for example exhibiting a shift of 25 nm or greater. When the compound of the invention exhibits a wavelength shift upon exposure to target ions, the measurement of the target ion can be performed on an absolute scale. In other embodiments, when a measurement is performed in a biological fluid, the levels of target ion to be measured are, for example, near or below typical resting values. When the target ion is $Ca^{2+}$, a typical resting value is approximately $10^{-7}$ M.

To perform detection of a target ion, the compound of the invention is combined with a sample in a way that will facilitate detection of the target ion concentration in the sample. The sample is, for example, a cell population, fluid or liquid suspension that is known or suspected to contain the target ion. Other samples include intracellular fluids such as in blood cells, cultured cells, muscle tissue, neurons and the like; extracellular fluids in areas immediately outside of cells; in vesicles; in vascular tissue of plants and animals; in biological fluids such as blood, saliva, and urine; in biological fermentation media; in environmental samples such as water, soil, waste water and sea water, in industrial samples such as pharmaceuticals, foodstuffs and beverages; and in chemical reactors. Detection and quantitation of the target ion in a sample can help characterize the identity of an unknown sample, or facilitate quality control of a sample of known origin.

Measurement of target ion levels in samples is typically performed using the compounds of the invention in methods known in the art. For example, ratiometric measurement of ion concentrations is performed by treatment of the fluorescence data as the ratio of excitation or fluorescence intensities at two wavelengths, rather than the absolute intensity at a single wavelength. Using this method, a number of variables that may perturb the ion concentration measurements are eliminated. In particular, ion-dependent factors that affect the signal intensity, such as nonuniform intracellular dye concentrations, probe leakage, dye bleaching and cell thickness, are canceled in ratiometric measurements, since these parameters have a similar effect on intensities at both wavelengths. This method can be used to determine concentrations by observation of either the excitation spectra of the indicator, the emission spectra of the indicator, or both. Calibration is used to compensate for variance in the dissociation constant of the indicator due to ionic strength, viscosity, or other conditions within the sample. For instance, calibration may be achieved using ionophores such as A-23187, gramicidin, valinomycin, or ionomycin. Non-ratiometric analysis can also be accomplished by calibration with a second fluorescent dye present in the sample.

Any device known in the art and disclosed herein can be used to perform the optical detection and/or quantitation of target ions, for example by observation of absorbance or fluorescence changes with an instrument, visually, or by use of a fluorescence sensing device. Fluorescence sensing devices include fluorometers, fluorescence microscopes, laser scanners, flow cytometers, and microfluidic devices, as well as cameras and other imaging equipment.

The examples below are for the purpose of illustrating the practice of the invention. They shall not be construed as being a limitation on the scope of the invention or claims.

EXAMPLES

Example 1

Preparation of compound No. 1

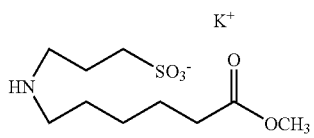

Compound No. 1

A mixture of methyl 6-aminohexanoate hydrochloride (10 g), 1,3-propanesulftone (7.4 g) and potassium carbonate (11.4 g) in $CH_3CN$ (200 mL) was stirred at room temperature for 2 days and then heated at 60° C. for 1 day. After cooling to room temperature, the mixture was suction filtered and the filtrate was concentrated to dryness in vacuo. To the residue was added EtOAc (200 mL) and the suspension was stirred at room temperature for 3 hrs. The precipitate was collected by suction filtration. The crude product was purified by a short silica gel column eluting with $H_2O/CH_3$ (20 g).

Example 2

Preparation of Compound No. 2

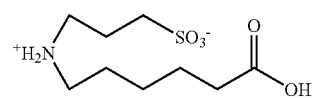

Compound No. 2

To compound No. 1 (5 g) in $H_2O$ (20 mL) was added a solution of NaOH (3.8 g) in $H_2O$ (20 mL). The mixture was stirred at room temperature for 2 hrs and the solution was neutralized to pH=7 with HCl (6 N) solution. The solution was concentrated to dryness in vacuo. The crude product was desalted though a short silica gel column using $H_2O/CH_3CN$ as the eluent. The collected product was dried to a constant weight (3.5 g) under high vacuum.

Example 3

Preparations of Compound No. 3a-6a

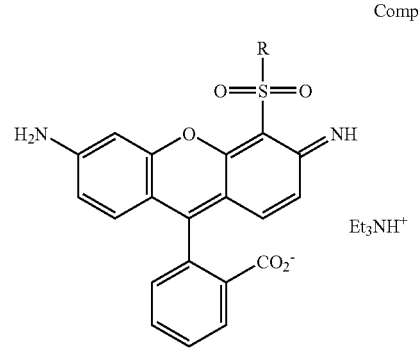

Compound Nos. 3a-6a

3a: R = —Cl
4a: R = —$HN(CH_2CH_2O)_8CH_2CH_2CO_2H$
5a: R = —$HNCH(CH_2SO_3^-)CO_2^-$
6a: R = —$N(CH_2CH_2CH_2SO_3^-)$
$(CH_2CH_2CH_2CH_2CH_2CO_2^-)2[Et_3NH]^+$

A mixture of rhodamine 110 (0.2 g) (Biotium cat. #80103) in chlorosulfonic acid (3 mL) was heated at 40° C. for 2 hr and then cooled to room temperature. The solution was added dropwise slowly to a vigorously stirred crushed ice (80 g). The precipitate was suction filtered off and washed with cold water (2×5 mL) to give crude compound No. 3a, which was sufficiently pure for most subsequent conjugation reactions but could be made more stable for storage by immediate lyophilization. The above precipitate was cooled to 0° C. and a solution of the corresponding aminoalkyl acid (1 equivalent of $H_2N(CH_2CH_2O)_8CH_2CH_2CO_2H$, cysteic acid, or compound No. 2) in a mixture of $CH_3CN$ (5 mL) and $H_2O$ (5 mL) containing $Et_3N$ (1 mL) was added. The mixture was stirred at 0° C. for 30 minutes and then at room temperature for 2 hrs. The solution was concentrated to dryness in vacuo and the crude product was purified by preparative HPLC using C18 reverse phase column to give compound No. 4a, 5a or 6a.

Example 4

Preparation of Compound No. 6b

To 30% fuming sulfuric acid (0.5 mL) at 0° C. was added compound No. 6a (10 mg) in one portion. The mixture was stirred at 0° C. for 1 hr and poured into ice-cold $Et_2O$ (20 mL) with $Et_3N$ (2 mL). The solution was concentrated to dryness in vacuo and the residue was purified by preparative HPLC using reverse phase C18 column to compound No. 6b (6 mg).

Example 5

Preparation of Compound No. 4b

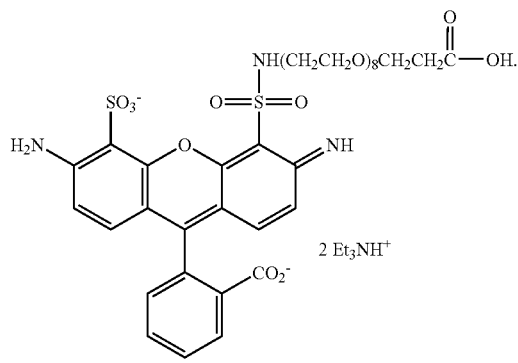

The synthesis of compound No. 4b was carried out by following the procedure for preparing compound No. 6b in Example 4 using compound No. 4a as the starting material.

Example 6

Preparation of Compound No. 4c

Compound No. 4c

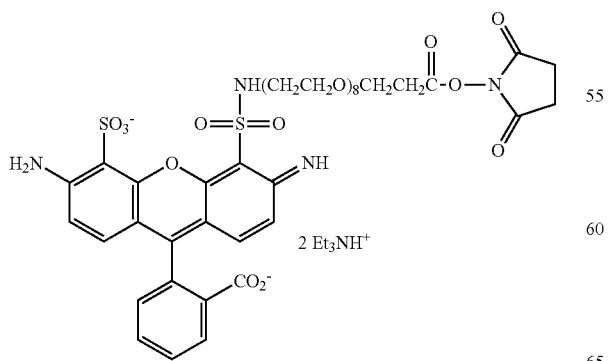

To a solution of compound No. 4b (34 mg) in DMF (500 μL) at 0° C. was added $Et_3N$ (26 μL) and TSTU (11 mg). The mixture was stirred at 0° C. for 30 minutes and then concentrated to dryness in vacuo. To the residue was added $Et_2O$ (1 mL) and the mixture was stirred at room temperature for 1 hr. The precipitate (30 mg) was collected by centrifugation and dried to a constant weight in vacuo.

Example 7

Preparation of Compound No. 6c

Compound No. 6c

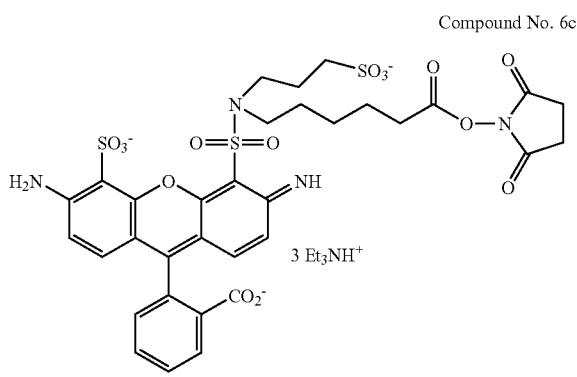

Compound No. 6c (5 mg) was prepared from compound No. 6b (8 mg) according to the synthesis of compound No. 4c.

Example 8

Preparation of Compound No. 7

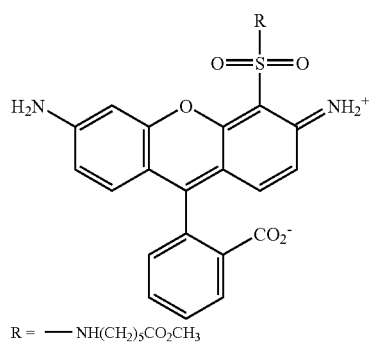

$R = \text{—NH}(CH_2)_5CO_2CH_3$

Compound No. 3a prepared from 0.2 g rhodamine 110 as described in Example 3 was cooled to 0° C. and a solution of methyl 6-aminohexanoate (1 equivalent) in a mixture of $CH_3CN$ (10 mL) containing $Et_3N$ (1 mL) was added. The mixture was stirred at 0° C. for 30 minutes and then at room temperature for 2 hrs. The solution was concentrated to dryness in vacuo and the crude product was purified by silica gel column chromatography to give compound No. 7.

Example 9

Preparation of Compound No. 8

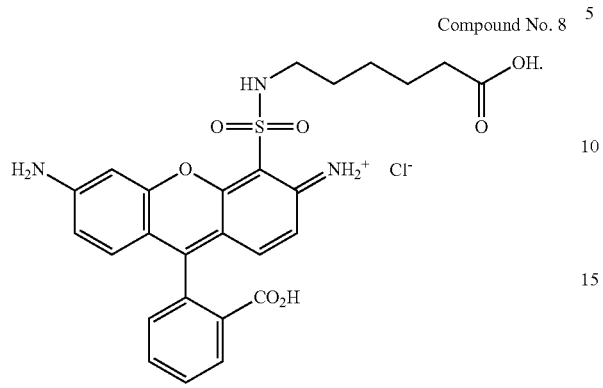

Compound No. 8

To a solution of compound No. 7 (100 mg) in CH₃OH (2 mL) was add 1N NaOH (2 mL). The mixture was stirred at room temperature overnight and then concentrated to dryness in vacuo. 1N HCl (3 mL) was added to the residue and the resulting suspension was stirred at room temperature for 3 hrs. The precipitate of compound No. 8 (60 mg) was collected by suction filtration.

Example 10

Preparation of Compound No. 9

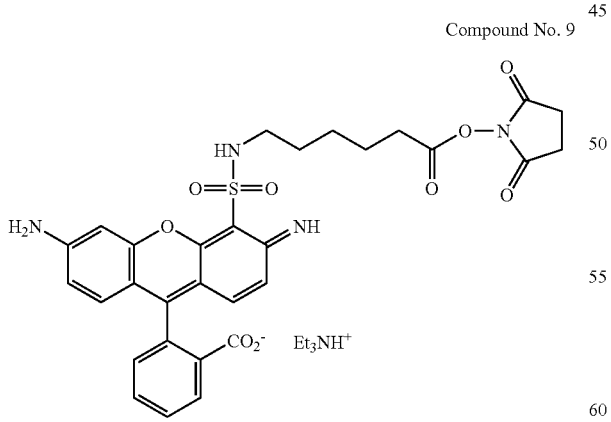

Compound No. 9

Compound No. 9 (20 mg) was prepared from compound No. 8 (22 mg) according to the synthesis of compound No. 4c.

Example 11

Preparation of Compound No. 10

Compound No. 10

Compound No. 10 was prepared by first reacting compound No. 3a with di-tert-butyl iminodiacetate (1 equivalent) to form a methyl ester intermediate (See Example 8). To a suspension of the intermediate (45 mg) in CH₂Cl₂ (1 mL) at 5° C. was added trifluoroacetic acid (0.5 mL). The mixture was stirred at 5° C. for 1 hr and then at room temperature overnight. The solution was concentrated to dryness in vacuo and Et₂O (2 mL) was added to the residue. The suspension was stirred at room temperature for 3 hrs and the precipitate (20 mg) was collected by centrifugation.

Example 12

Preparations of Compound Nos. 11 and 12

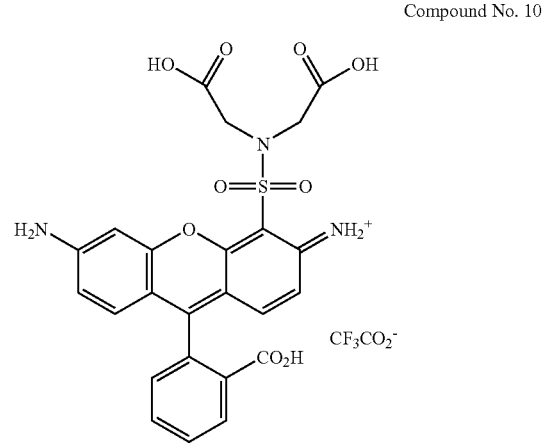

Compound No. 11: R = —NH(CH₂)₅CO₂CH₃
Compound No. 12: R = —N(CH₂CO₂-t-But)₂

A mixture of rhodamine 110 (0.2 g) in chlorosulfonic acid (3 mL) was heated at 80° C. for 1 hr and 20 minutes and then cooled to room temperature. The solution was added dropwise slowly to a vigorously stirred crushed ice (80 g). The resulting precipitate of the bis-sulfonylchloride dye intermediate was suction filtered and washed with cold water (2×5 mL). The crude product was cooled to 0° C. and a solution of either methyl 6-aminohexanoate or di-cert-butyl iminodiacetate (1 equivalent) in a mixture of CH₃CN (10 mL) containing Et₃N (1 mL) was added. The mixture was stirred at 0° C. for 30 minutes and then at room temperature for 2 hrs. The solution was concentrated to dryness in vacuo and the crude product was purified by silica gel column chromatography to give compound No. 11 or 12.

Example 13

Preparation of Compound No. 13

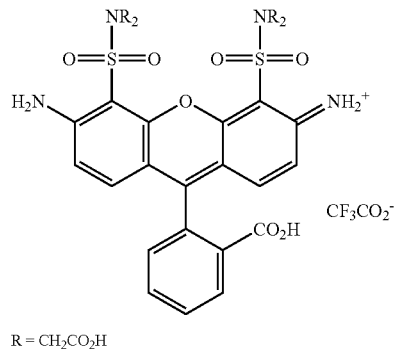

Compound No. 13

R = CH$_2$CO$_2$H

Compound No. 13 (25 mg) was prepared from compound No. 12 (100 mg) by deprotection using TFA according to the synthesis of compound No. 10 in Example 11.

Example 14

Preparation of Compound No. 14a and Compound No. 14b

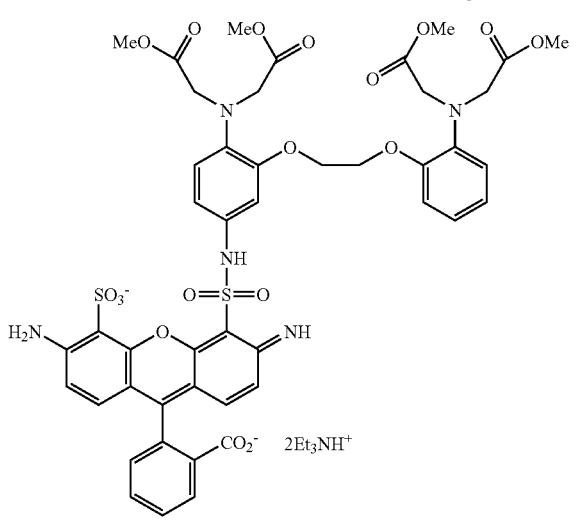

Compound No. 14a

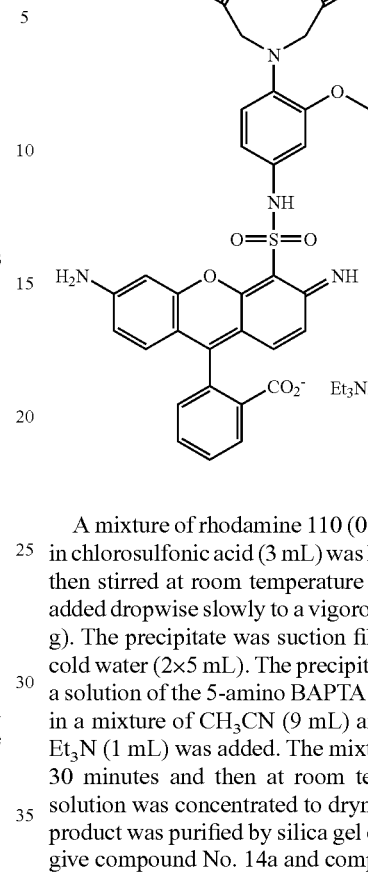

Compound No. 14b

A mixture of rhodamine 110 (0.2 g) (Biotium cat. #80103) in chlorosulfonic acid (3 mL) was heated at 80° C. for 1 hr and then stirred at room temperature for 1 hr. The solution was added dropwise slowly to a vigorously stirred crushed ice (80 g). The precipitate was suction filtered off and washed with cold water (2×5 mL). The precipitate was cooled to 0° C. and a solution of the 5-amino BAPTA methyl ester (1 equivalent) in a mixture of CH$_3$CN (9 mL) and H$_2$O (1 mL) containing Et$_3$N (1 mL) was added. The mixture was stirred at 0° C. for 30 minutes and then at room temperature for 2 hrs. The solution was concentrated to dryness in vacuo and the crude product was purified by silica gel column chromatography to give compound No. 14a and compound No. 14b.

Example 15

Preparation of Compound No. 15

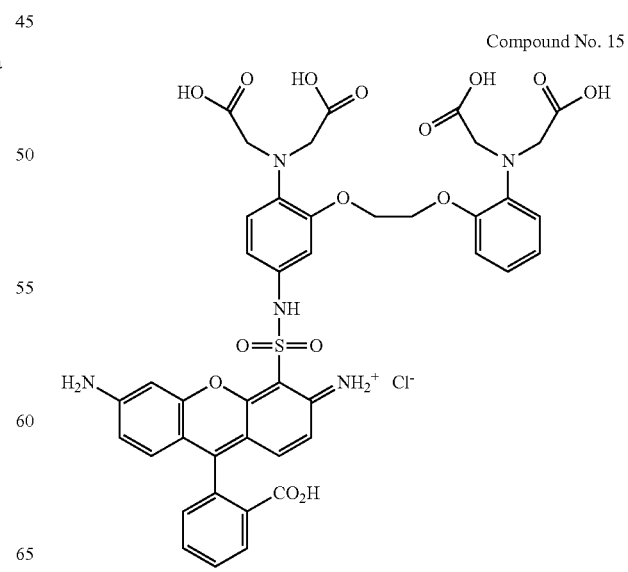

Compound No. 15

Compound No. 15 (4 mg) was prepared from compound No. 14b (13 mg) by base-catalyzed hydrolysis according to the synthesis of compound No. 8 in Example 9.

Example 16

Preparation of Compound No. 16

Compound No. 16

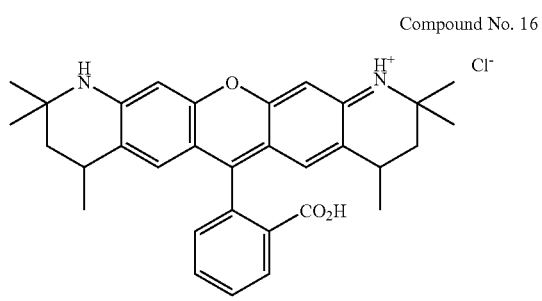

To a stirred mixture of 7-hydroxy-2,2,4-trimethyl-1,2,3,4-tetrahydroquinoline (510 mg) and phthalic anhydride (198 mg) in propionic acid (5 mL) was added p-toluenesulfonic acid (100 mg). The mixture was refluxed gently for 24 hrs. After cooling down to room temperature, the solvent was removed by vacuum distillation. The residue was purified by silica gel column chromatography to give compound No. 16 as an orange solid (100 mg).

Example 17

Preparation of Compound No. 17a and Compound No. 17b

Compound No. 17a

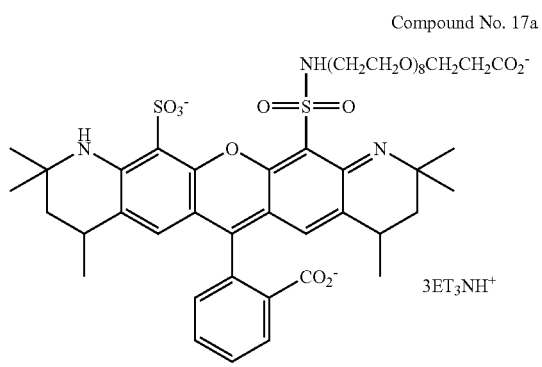

Compound No. 17b

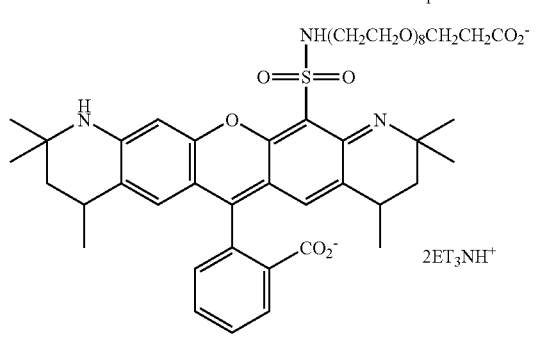

A mixture of compound No. 16 (0.1 g) in chlorosulfonic acid (2 mL) was heated at 80° C. for 1 hr and then stirred at room temperature for 1 hr. The solution was added dropwise slowly to a vigorously stirred crushed ice (50 g). The precipitate was suction filtered off and washed with cold water (2×3 mL). The precipitate was cooled to 0° C. and a solution of the amino dPEG8 acid (1 equivalent) in a mixture of $CH_3CN$ (95 mL) and $H_2O$ (0.5 mL) containing $Et_3N$ (0.5 mL) was added. The mixture was stirred at 0° C. for 30 minutes and then at room temperature for 2 hrs. The solution was concentrated to dryness in vacuo and the crude product was purified by preparative HPLC using C18 reverse phase column to give compound No. 17a and compound No. 17b.

Example 18

Preparation of Compound No. 18

Compound No. 18

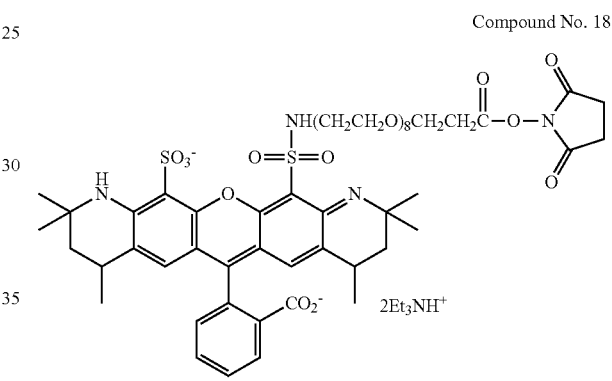

Compound No. 18 (4 mg) was prepared from compound No. 17a (7 mg) according to the synthesis of compound No. 4c.

Example 19

Preparation of Compound No. 19

Compound No. 19

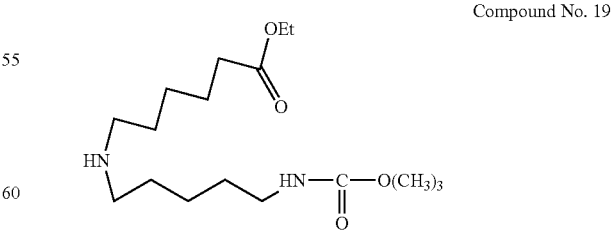

A mixture of N-t-BOC-cadaverine (0.5 g), ethyl 6-bromo-hexanoate (0.46 mL) and potassium carbonate (0.7 g) in $CH_3CN$ was stirred at room temperature for 2 days. The mixture was suction filtered and the filtrate was concentrated to dryness in vacuo. The residue was purified by silica gel column chromatography to give compound No. 19 as colorless oil (540 mg).

Example 20

Preparation of Compound No. 20

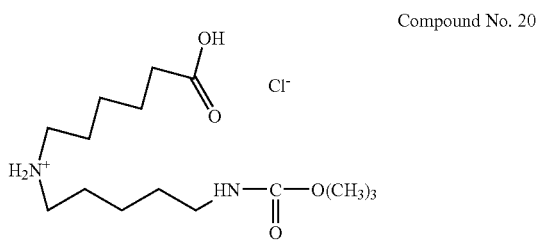

Compound No. 20

A mixture of compound No. 19 (500 mg) and NaOH (300 mg) in H$_2$O (10 mL) was stirred at room temperature for 3 hrs. The solution was acidified to pH=5 with 1N HCl and concentrated to dryness in vacuo to give a colorless solid (300 mg).

Example 21

Preparation of Compound No. 21a and Compound No. 21b

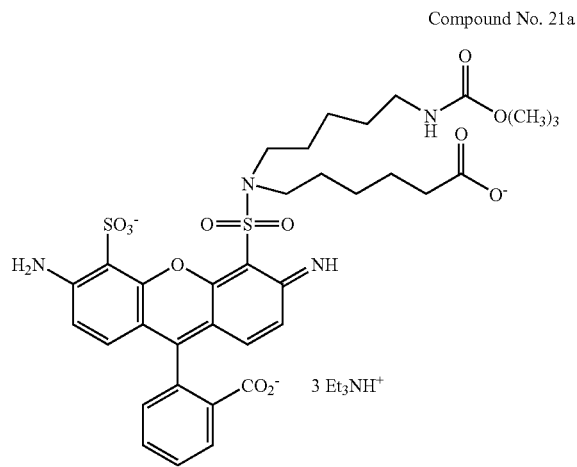

Compound No. 21a

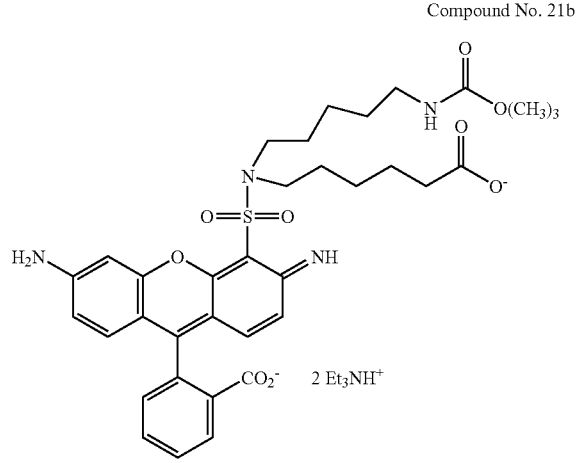

Compound No. 21b

A mixture of rhodamine 110 (0.2 g) (Biotium cat. #80103) in chlorosulfonic acid (5 mL) was heated at 80° C. for 1 hr and then stirred at room temperature for 1 hr. The solution was added dropwise slowly to a vigorously stirred crushed ice (80 g). The precipitate was suction filtered off and washed with cold water (2×5 mL). The precipitate was cooled to 0° C. and a solution of compound No. 20 (1 equivalent) in a mixture of CH$_3$CN (5 mL) and H$_2$O (5 mL) containing Et$_3$N (1 mL) was added. The mixture was stirred at 0° C. for 30 minutes and then at room temperature for 2 hrs. The solution was concentrated to dryness in vacuo and the crude product was purified by preparative HPLC using C18 reverse phase column to give compound No. 21a and compound No. 21b Example 22

Preparation of Compound No. 22

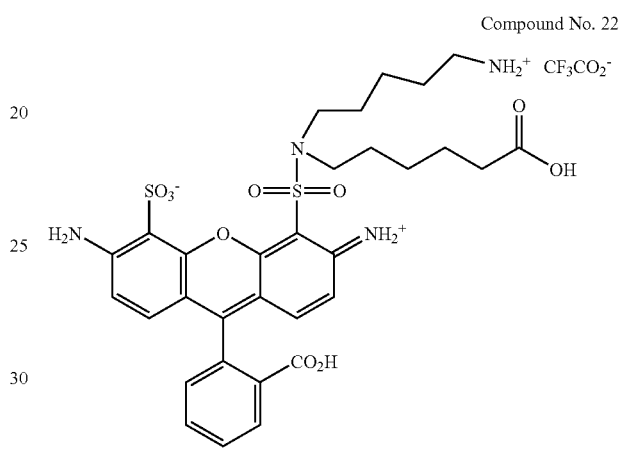

Compound No. 22

To a suspension of compound No. 21b (15 mg) in CH$_2$Cl$_2$ (1 mL) at 0° C. was added CF$_3$CO$_2$H (0.5 mL). The mixture was stirred at 0° C. for 1 hr and then concentrated to dryness in vacuo. Et$_2$O (2 mL) was added to the residue and the suspension was stirred at room temperature for 2 hr. The precipitate (7 mg) was collected by centrifugation.

Example 23

Preparation of Compound No. 23

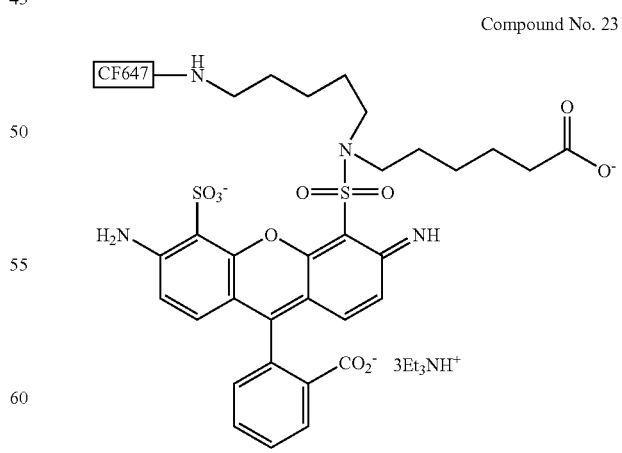

Compound No. 23

To CF647 SE (1 µmol (Biotium cat #. 92135) and Et$_3$N (10 µL) in DMF (100 µL) was added a solution of compound No. 22 (1 µM) in DMF (100 µL). The mixture was stirred at room temperature for 30 minutes and then concentrated to dryness in vacuo. The residue was purified by preparative HPLC using C18 reverse phase column to give compound No. 23 as blue solid (2 mg).

Example 24

Preparation of Compound No. 24

Compound No. 24

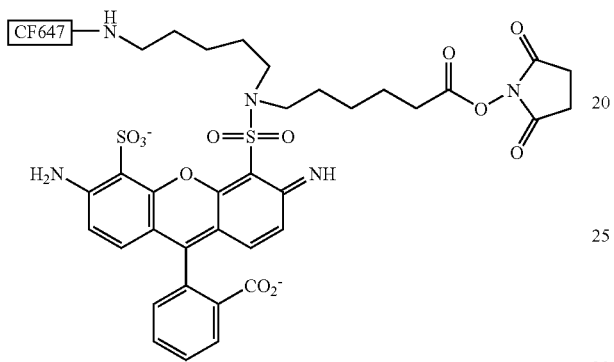

Compound No. 24 (2 mg) was prepared from compound No. 23 (2 mg) according to the synthesis of compound No. 4c.

Example 25

Preparations of Compound Nos. 25a, 26a, 25b and 26b

Compound Nos. 25a and 26a

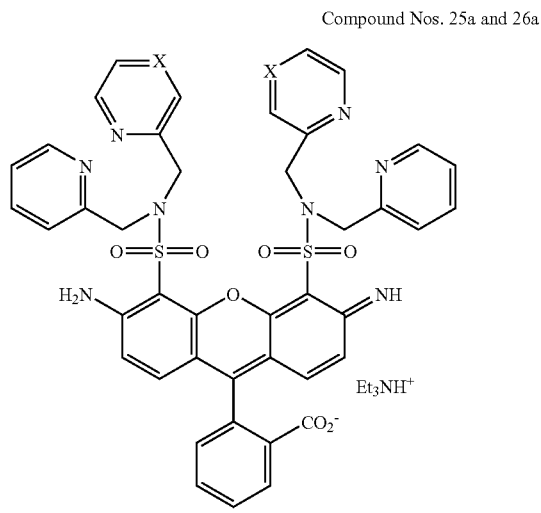

Compound Nos. 25b and 26b

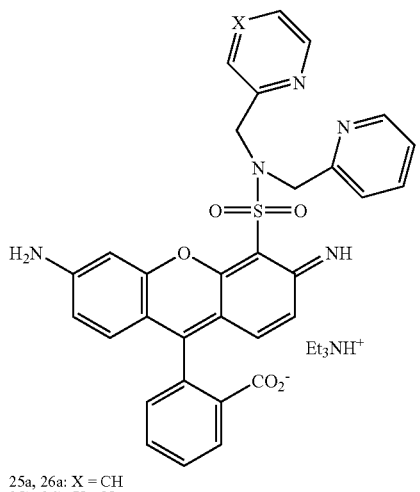

25a, 26a: X = CH
25b, 26b: X = N

A mixture of rhodamine 110 (0.2 g) (Biotium cat. #80103) in chlorosulfonic acid (3 mL) was heated at 80° C. for 1 hr and then stirred at room temperature for 1 hr. The solution was added dropwise slowly to a vigorously stirred crushed ice (80 g). The precipitate was suction filtered off and washed with cold water (2×5 mL). The precipitate was cooled to 0° C. and a solution of the corresponding di-(2-picolyl)amine (Aldrich, cat #385638) or (2-picolyl)(pyrazin-2-ylmethypamine (J. Amer. Chem. Soc., 2008, 130, 15788) (1 equivalent) in a mixture of $CH_3CN$ (10 mL) containing $Et_3N$ (1 mL) was added. The mixture was stirred at 0° C. for 30 minutes and then at room temperature for 2 hrs. The solution was concentrated to dryness in vacuo and the crude product was purified by silica gel column chromatography to give compound Nos. 25a, 26a, 25b or 26b.

Example 26

Preparation of Protein Dye-Conjugates

Fluorescent conjugates of goat anti-mouse IgG (GAM), goat anti-rabbit IgG (GAR), streptavidin and annexin V were prepared from the respective proteins and a reactive dye. Briefly, an antibody or streptavidin at 1 mg/mL in 0.1 mM pH 8.5 sodium bicarbonate buffer was mixed with one of the reactive dye at various ratio of dye molecules/protein molecule. After incubating for about an hour at room temperature, the reaction mixture was separated by gel filtration using Sephadex G-25 equilibrated with PBS (pH 7.4). The various dye molecules/protein ratios used in the labeling reactions produced protein conjugates with different degree of dye labeling (DOL) as listed in Table 2 below for each dye/protein pair.

TABLE 2

List of selected antibody and streptavidin conjugates prepared according to the invention

| Protein | Dye | Degree of Labeling (DOL) |
| --- | --- | --- |
| Goat anti-mouse IgG | Compound No. 4c | 1.5; 2.0; 3.1; 4.8; 5.3; 7.5; 10.3 |
| Goat anti-mouse IgG | Alexa Fluor ® 488 SE | 1.2; 2.2; 3.1; 4.1; 4.8; 7.3 |

TABLE 2-continued

List of selected antibody and streptavidin conjugates prepared according to the invention

| Protein | Dye | Degree of Labeling (DOL) |
|---|---|---|
| Goat anti-mouse IgG | DyLight ™ 488 SE | 1.2; 2.3; 3.3; 4.1; 4.5; 5.5 |
| Annexin V | Compound No. 4c | 1.7 |

The fluorescence of the antibody conjugates was measured using a JACSO fluorescence spectrophotometer and was then plotted against the DOL to give FIG. 2.

Example 27

Preparation of a Phalloidin Dye-Conjugate

To aminophalloidin (1 mg) and compound No. 18 (1.5 equivalents) in DMF (200 μL) was added N,N-diisopropylethylamine (3 equivalents) and the mixture was stirred at room temperature overnight. The solution was concentrated to dryness under vacuum and the residue was purified by column chromatography by LH-20 column (1.5 mg). The product is an effective stain for F-actin filaments in fixed-cell preparations.

Example 28

Preparation and Use of a Fluorescent α-Bungarotoxin Dye-Conjugate

To a solution of α-bungarotoxin (1 mg) in 0.1 M sodium bicarbonate (25 μL) was added compound No. 18 (1.5 equivalents) in one portion and the mixture was stirred at room temperature for 2 hours. The product was purified by G-25 size exclusion column and then by reverse-phase HPLC.

Example 29

Preparation of Nucleotide-Dye Conjugates

To a solution of 5-(3-aminoallyl)-2-deoxyuridine 5'-triphosphate (2 mg, Sigma Chemical) in $H_2O$ (100 μL) is added compound No. 4c in DMF and triethylamine (5 μL). The mixture is stirred at room temperature for 3 hours and then concentrated to dryness in vacuo. The residue is purified by preparative HPLC. The product fractions are lyophilized to give a yellow orange nucleotide conjugate.

Example 30

Preparation of an Oligonucleotide Dye-Conjugate

To a 5'-amine-modified, 18-base M13 primer sequence (100 μg) in $H_2O$ (4 μL) is added a solution of compound No. 7 (500 μg) in 0.1 M sodium borate pH=8.5 buffer (200 lit). The mixture is stirred at room temperature overnight and 3 volumes of cold ethanol are added. The mixture is cooled to −20° C., centrifuged, the supernatant is decanted, the pellet is rinsed with ethanol and then dissolved in $H_2O$ (100 μL). The labeled oligonucleotide is purified by preparative HPLC. The desired peak is collected and evaporated to give the fluorescent oligonucleotide.

Example 31

Figure 3A:
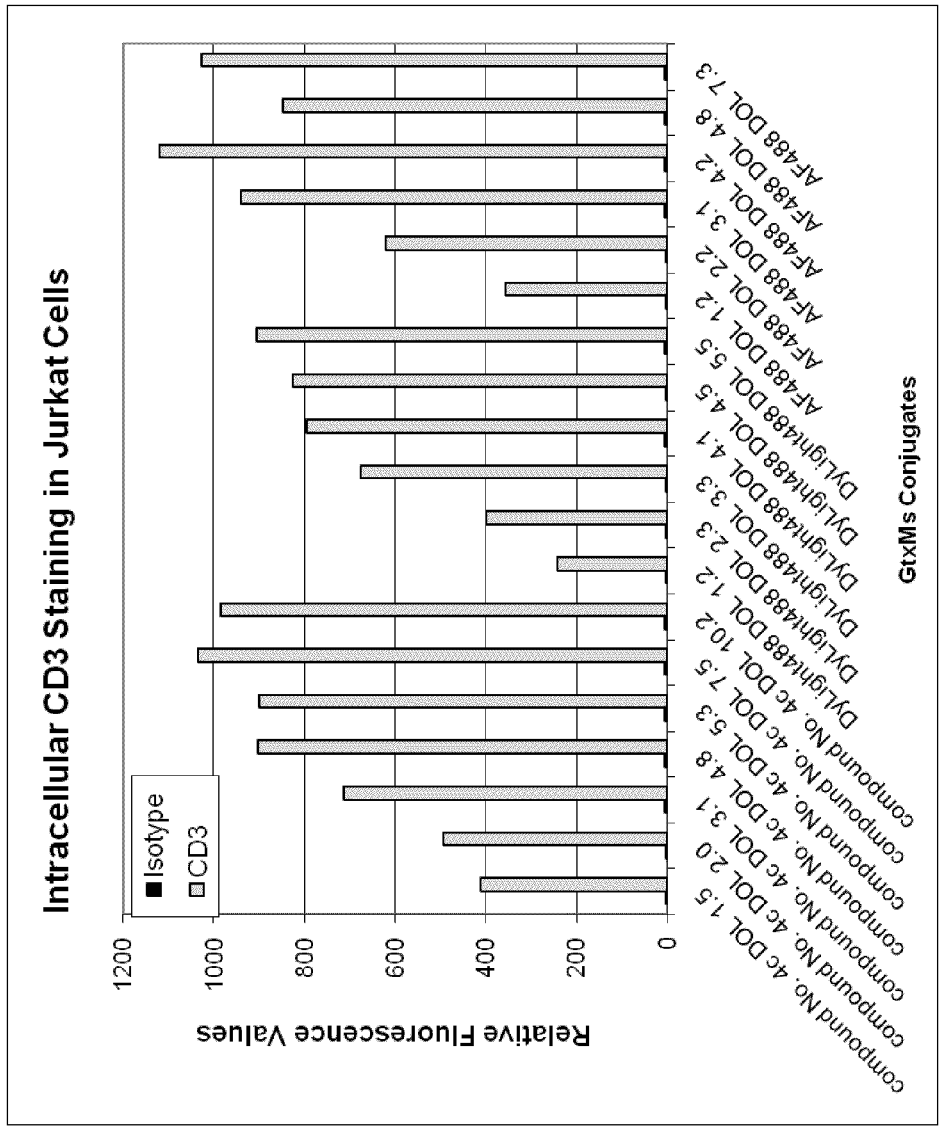
FIG. 3A is a flow cytometry histogram showing the relative fluorescence levels of Jurkat cells stained with various fluorescently labeled antibodies. The cells were first labeled with mouse anti-human CD3 antibody and then stained with goat anti-mouse IgG labeled with Compound No. 4c, Alexa Fluor 488 or DyLight 488 at an indicated degree of labeling (DOL) (light gray columns). To measure the background fluorescence from each labeled secondary antibody, the staining experiments were also carried out using an isotype primary antibody to replace the CD3 antibody (dark columns). The results show that cells stained with antibody conjugates of this invention have excellent signals.
Figure 3B:
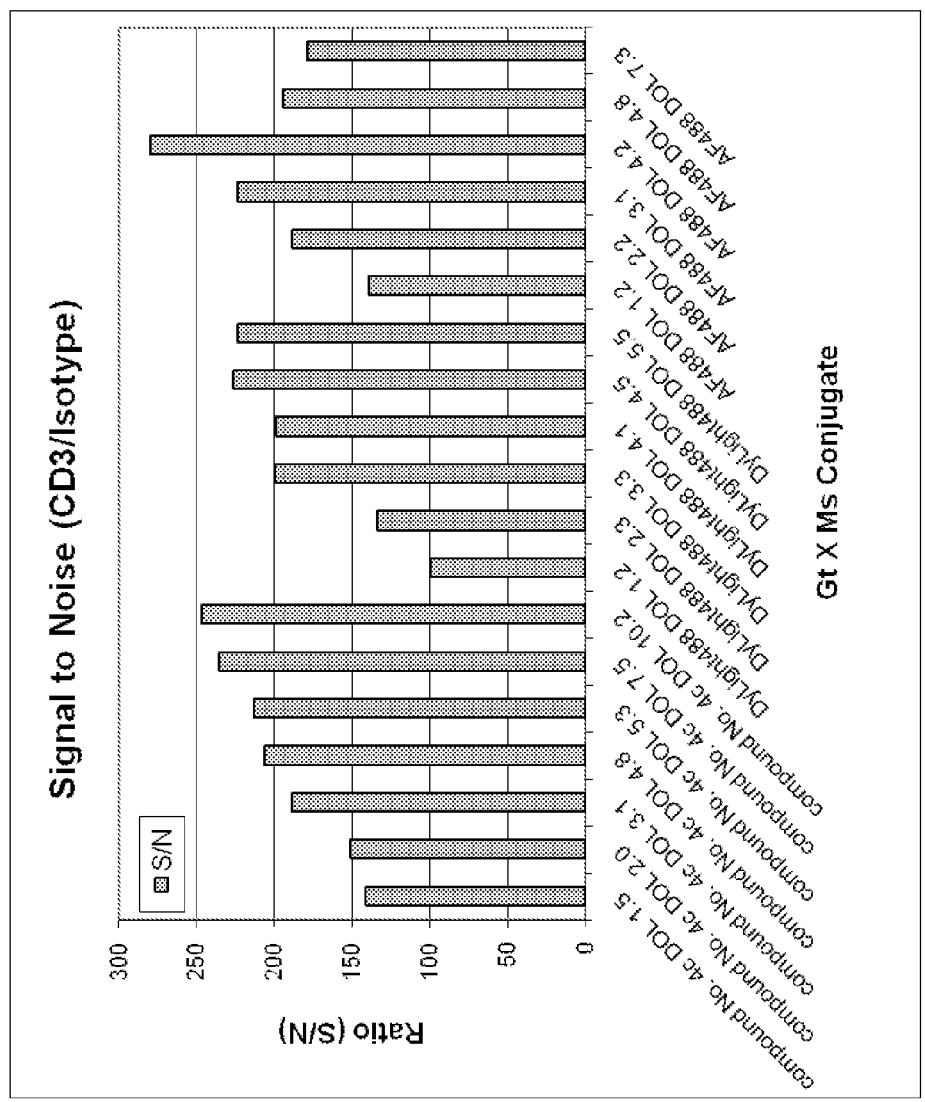
FIG. 3B is a graphical representation showing the signal-to-noise ratios of the stainings from FIG. 3A. The dye of the invention showed excellent signal-to-noise ratio even at very high DOL. See Example 31.

Flow Cytometry Analysis of Cells Intracellularly Stained with Dye-Antibody Conjugates One million Jurkat cells were fixed, permeabilized, and incubated with 0.25 μg mouse anti-human CD3 antibody (BD Biosciences). The CD3 antibody was followed by incubation with 1 μg goat anti-mouse IgG labeled with compound No. 4c, Alexa Fluor® 488 or DyLight™ 488 at an indicated DOL (Example 26). About 10,000 cells from each sample were analyzed on a BD FACS Calibur flow cytometer and fluorescence was detected in the FL1 channel. To compare the background staining of the labeled secondary antibodies, the staining experiments were also carried out with the primary antibody being replaced with an isotype primary antibody. The data is presented in FIGS. 3A and 3B.

Example 32

Photostability Comparison Between Compound No. 4c and FITC

Jurkat cells were treated with 1 uM staurosporine for 4 hrs to induce apoptosis. Live cells were stained with Annexin V labeled with either compound No. 4c or FITC. The annexin V labeled with compound No. 4c had a DOL of 1.7 and was prepared according to Example 26. The FITC-labeled annexin V was a commercial product from Biotium. Cells were mounted on glass slides and 2 random fields of view were chosen for photostability studies. Cells were continuously exposed on an Olympus mercury arc lamp microscope and images were captured at 30 second intervals for 2 min. Fluorescence was normalized to the first image set at 100%.

Example 33

Intracellular Staining of Jurkat Cells with Goat Anti-Mouse IgG Labeled with Compound No. 4c Image: HeLa cells were fixed, permeabilized and stained with mouse alpha-tubulin antibody followed by 5 ug/mL goat anti-mouse IgG labeled with compound No. 4c (DOL 4.8). Images were captured on an Olympus mercury arc lamp microscope at 60× using a CCD camera and ImagePro Express software.

What is claimed is:
1. A compound of Formula Ia or Ib:

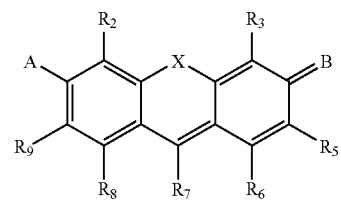

Formula Ia

-continued

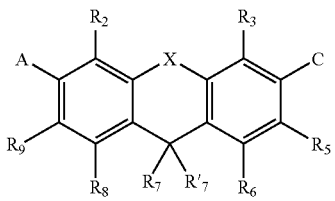

Formula Ib wherein:
X is O, S, or —C(CH$_3$)$_2$—;
A is —OR$_1$ or —NR$_1$R$_{1a}$;
B is =O or =N$^+$R$_4$R$_{4a}$;
C is —OR$_4$ or —NR$_4$R$_{4a}$;
R$_1$R$_{1a}$, R$_4$ and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;
R$_2$, R$_3$, R$_5$, R$_6$, R$_7$, R$_8$ and R$_9$ are each independently H, halogen, CN, alkyl, alkenyl, alkoxy, alkylthio, alkylamino, dialkylamino, alkylaminocarbonyl, dialkylaminocarbonyl, aryl, heteroaryl, -L-PO$_3^{2-}$, L-SO$_3^-$, -L-R$_x$, a reactive sulfonamide or an unreactive sulfonamide; or one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, heteroalkyl, alkenyl, alkoxy, alkylthio, alkylamino, dialkylamino, alkylaminocarbonyl, dialkylaminocarbonyl, aryl, heteroaryl, -L-PO$_3^{2-}$, L-SO$_3^-$, -L-R$_x$, a reactive sulfonamide or an unreactive sulfonamide;
R$_7$' is H, OH, CN, or C$_1$-C$_6$ alkoxy; or R$_7$' in combination with R$_7$ forms a 5- or 6-membered spirolactone or spirosultone ring;
R$_x$ is a reactive group;
L is a bond or (Q)$_n$;
each Q is independently NR$_d$, S(O)$_t$, O, C(=X'), (C=X'), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;
each X' is independently NR$_d$, S or O;
n is 1-20;
each R$_d$ is H, substituted or unsubstituted alkyl;
provided that at least one of R$_2$, R$_3$, R$_5$ and R$_9$ is a reactive sulfonamide,
wherein one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, heteroalkyl, alkenyl, alkoxy, alkylthio, alkylamino, dialkylamino, alkylaminocarbonyl, dialkylaminocarbonyl, aryl, heteroaryl, -L-PO$_3^{2-}$, -L-SO$_3^-$, -L-R$_x$, a reactive sulfonamide or an unreactive sulfonamide.

2. The compound of claim 1, wherein the compound comprises at least one reactive sulfonamide of Formula IIa:

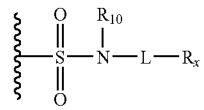

Formula IIa wherein:
R$_{10}$ is H or a substituted or unsubstituted C$_1$-C$_{12}$ alkyl; or R$_{10}$ and L together with the nitrogen to which they are attached form a saturated or unsaturated ring.
3. The compound of claim 2, wherein R$_{10}$ is H, sulfopropyl or sulfobutyl.
4. The compound of claim 2 having the structure of Formula IIIa:

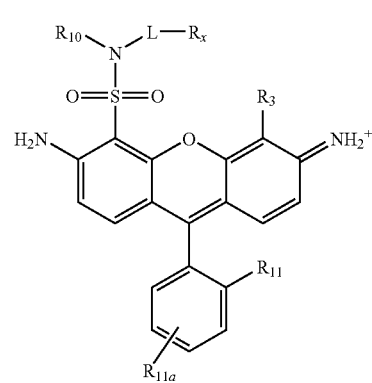

Formula IIIa wherein:
R$_3$ is H, —SO$_3^-$, or an unreactive sulfonamide;
R$_{11}$ is —CO$_2^-$ or —SO$_3^-$; and
R$_{11a}$ is H, —SO$_3^-$, or an unreactive sulfonamide.
5. The compound of claim 4 wherein:
R$_3$ is H or —SO$_3^-$; and
L is Q$_n$, wherein at least one, two, three or four Q are —(CH$_2$CH$_2$O)—.
6. The compound of claim 2 having the structure of Formula IV:

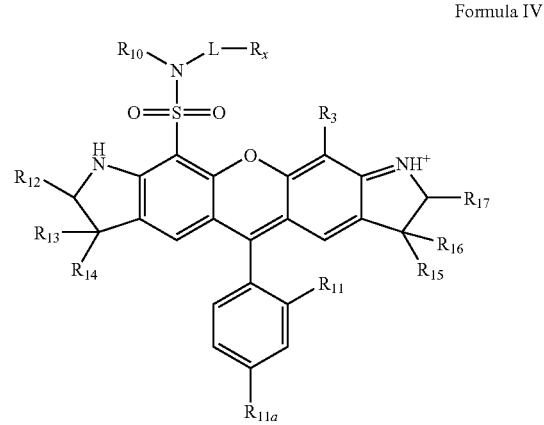

Formula IV wherein:

R$_3$ is H, —SO$_3^-$, or unreactive sulfonamide;

R$_{10}$ is H, sulfopropyl or sulfobutyl;

R$_{11}$ is —CO$_2^-$ or —SO$_3^-$;

R$_{11a}$ is H, —SO$_3^-$, or an unreactive sulfonamide; and

R$_{12}$, R$_{13}$, R$_{14}$, R$_{15}$, R$_{16}$ and R$_{17}$ are each independently H or methyl.

7. The compound of claim 2 having the structure of Formula V:

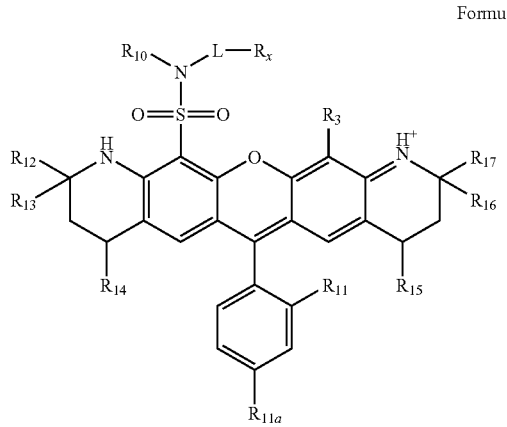

Formula V wherein:

R$_3$ is H, —SO$_3^-$, or an unreactive sulfonamide;

R$_{11}$ is —CO$_2^-$ or —SO$_3$;

R$_{11a}$ is H, —SO$_3^-$, or an unreactive sulfonamide; and

R$_{12}$, R$_{13}$, R$_{14}$, R$_{15}$, R$_{16}$ and R$_{17}$ are each independently H or methyl.

8. A compound having the structure of Formula VI:

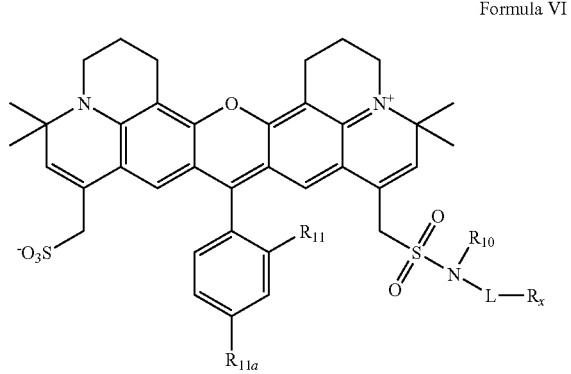

Formula VI wherein:

R$_{11}$ and R$_{11a}$ are each independently H, —SO$_3^-$, or unreactive sulfonamide;

R$_{10}$ is H, sulfopropyl or sulfobutyl;

L is a bond, or Q$_n$; wherein at least one Q is —(CH$_2$CH$_2$O)—; and

R$_x$ is a reactive group.

9. A compound of Formula Ia or Ib:

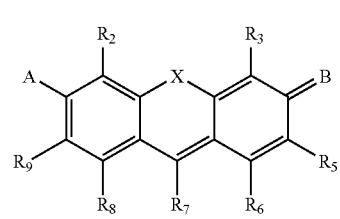

Formula Ia

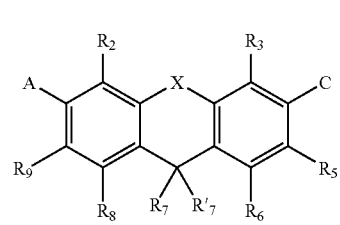

Formula Ib wherein:

X is O, S, or —C(CH$_3$)$_2$—;

A is —OR$_1$ or —NR$_1$R$_{1a}$;

B is =O or =N$^+$R$_4$R$_{4a}$;

C is —OR$_4$ or —NR$_4$R$_{4a}$;

R$_1$, R$_{1a}$, R$_4$ and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;

R$_2$, R$_3$, R$_5$, R$_6$, R$_7$, R$_8$ and R$_9$ are each independently H, halogen, CN, alkyl, alkenyl, alkoxy, alkylthio, alkylamino, dialkylamino, alkylaminocarbonyl, dialkylaminocarbonyl, aryl, heteroaryl, -L-PO$_3^{2-}$, L-SO$_3^-$, -L-R$_x$, a reactive sulfonamide, or a neutral or positively charged unreactive sulfonamide; or one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, heteroalkyl, alkenyl, alkoxy, alkylthio, alkylamino, dialkylamino, alkylaminocarbonyl, dialkylaminocarbonyl, aryl, heteroaryl, -L-PO$_3^{2-}$, L-SO$_3^-$, -L-R$_x$, a reactive sulfonamide, or a neutral or positively charged unreactive sulfonamide;

R$_7$' is H, OH, CN, or C$_1$-C$_6$ alkoxy; or R$_7$' in combination with R$_7$ forms a 5- or 6-membered spirolactone or spirosultone ring;

R$_x$ is a reactive group;

L is a bond or (Q)$_n$;

each Q is independently NR$_d$, S(O)$_p$, O, C(=X'), (C=X'), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two $NR_d$ are adjacent and no two O are adjacent;

each X' is independently $NR_d$, S or O;

n is 1-20;

each $R_d$ is H, substituted or unsubstituted alkyl;

provided that at least one of $R_2$, $R_3$, $R_5$ and $R_9$ is a neutral or positively charged unreactive sulfonamide, wherein the unreactive sulfonamide moiety has a structure of Formula IIb:

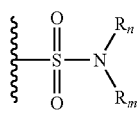

Formula IIb wherein $R_m$ and $R_n$ are each independently H, alkyl, or heteroalkyl.

10. The compound of claim 9, wherein $R_m$ and $R_n$ are each independently H or a $C_1$-$C_{12}$ alkyl.

11. The compound of claim 9, wherein the unreactive sulfonamide is positively charged.

12. The compound of claim 9 having the structure of Formula IIIb:

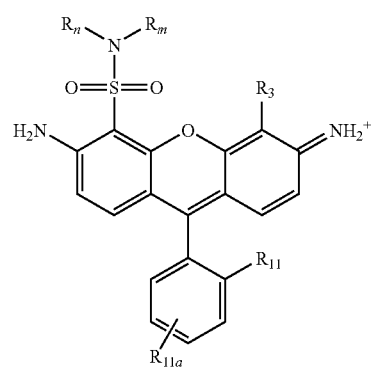

Formula IIIb wherein:
$R_3$ is —$SO_3^-$;
$R_m$ and $R_n$ are each independently H, alkyl, or heteroalkyl;
$R_{11}$ is —$CO_2^-$ or —$SO_3^-$; and
$R_{11a}$ is H, —CO2-, —$SO_3^-$, or -L-$R_x$.

* * * * *